United States Patent [19]

Gerald et al.

[11] Patent Number: 5,602,024
[45] Date of Patent: Feb. 11, 1997

[54] DNA ENCODING A HYPOTHALAMIC ATYPICAL NEUROPEPTIDE Y/PEPTIDE YY RECEPTOR (Y5) AND USES THEREOF

[75] Inventors: Christophe P. G. Gerald, Ridgewood; Mary W. Walker, Elmwood Park; Theresa Branchek, Teaneck, all of N.J.; Richard L. Weinshank, New York, N.Y.

[73] Assignee: Synaptic Pharmaceutical Corporation, Paramus, N.J.

[21] Appl. No.: 349,025

[22] Filed: Dec. 2, 1994

[51] Int. Cl.$^6$ .......................... C07H 21/00; C12N 15/12; C12N 15/63; C12N 5/10

[52] U.S. Cl. .................. 435/325; 435/252.3; 435/254.11; 435/320.1; 435/348; 435/365; 435/369; 536/23.5

[58] Field of Search .................. 536/23.5; 435/240.2, 435/252.3, 254.11, 320.1

Primary Examiner—Stephen G. Walsh
Assistant Examiner—Stephen Gucker
Attorney, Agent, or Firm—John P. White

[57] ABSTRACT

This invention provides an isolated nucleic acid molecule encoding a human Y5 receptor, an isolated protein which is a human Y5 receptor, vectors comprising an isolated nucleic acid molecule encoding a human Y5 receptor, mammalian cells comprising such vectors, antibodies directed to the human Y5 receptor, nucleic acid probes useful for detecting nucleic acid encoding human Y5 receptors, antisense oligonucleotides complementary to any sequences of a nucleic acid molecule which encodes a human Y5 receptor, pharmaceutical compounds related to human Y5 receptors, and nonhuman transgenic animals which express DNA a normal or a mutant human Y5 receptor. This invention further provides methods for determining ligand binding, detecting expression, drug screening, and treatment involving the human Y5 receptor.

30 Claims, 28 Drawing Sheets

FIGURE 3

```
    1  TTAGTTTGTTCTGAGAACGTTAGAGTTATAGTACCGTGCGATCGTTCTTCAAGCTGCTA        60
   61  ATGGACGTCCTCTTCTTCACCAGGATTCTAGTATGGAGTTTAAGCTTGAGGAGCATTTT       120
  121  AACAAGACATTGTCACAGAGAGCAGCGTAGACGATTACAATACAGCTGCTCGGAATGCAGCCTTCCCTGCC  180
  181  TGGGAGGACTACAGAGGCAGCGTAGACGATTACAATACTTTCTGATTGGCTGTTATACA       240
  241  TTCGTAAGTCTTCTTGGCTTTATGGCAATCTGAACTTTCTATTTTAATGGCCTTTCTGTGTTATGAAAAAG 300
  301  CGCAATCAGAAGACTACAGTGAACTGAACTTTCTCATAGCCAACCTGCTCTGTCTTCCGACATCTTG     360
  361  GTCGTCCTGTTTTGCTCCCCTTTCACCCTGACCTCTGTCTGTTGGATCAGTGATGTTT       420
  421  GGCAAAGCCATGTGCCATATCATGCCGTTCCTTCAATGTGTGTCAGTTCTGGTTTCAACT     480
  481  CTGATTTTAATATCAATTGCCATTGTCAGGTATCATATGACTACTGTCTGGACACTGTCTAAC       540
  541  AATTTAACGGCAAACCATGGCTACTTCCTGATAGCTCTTGTGGAACTTAAGGAGACCTTTGGCTCA     600
  601  ATCTGTCTCCCCTCCCAGTGTTTCACAGTCTTGTGGAACTTAAGGAGACCTTTGGCTCA       660
  661  GCACTGCTGAGTAGCAAATATCTCTGTGTTGAGTCATGGCCCTCTGATTCATACAGAATT     720
  721  GCTTTCACAATCTCTTTATTGCTAGTGCAGTATATCCTGCCTCTAGTATGTTTAACGGTA     780
  781  AGTCATACCAGCGTCTGCCGAAGCATAAGCTGTGGATTGTTCCCACAAAGAAAACAGACTC    840
  841  GAAGAAAATGAGATGATCAACTTAACCTACACTACTCATTCATTCAGAAGAGCAGGAACCAGGCA      900
  901  AAAACCCCCAGCACTGCCCTGTGTCTTACCCGCCCAGCAGACCTTCCCAGGGAAGCACCTA     960
  961  AGCAAGAAGACGGCCTGTGTCTTACCCGCCCAGCAGACCTGTCGCCATCCAGTAAGGTCATT  1020
 1021  GCCGTTCCAGAAAATCCAGCCCTCTTTGAGGTGAAATAAAAAAGATCTGAAGTGTTTCTACAGACTG   1080
 1081  CCAGGGTCCCAATCTGTCTTTGAGGTGAAATAAAAAAGATCTGAAGTGTTTCTACAGACTG    1140
 1141  AGAGTCAAGCGTTCCATCACTAGAATAAAAAAGATCTGAAGTGTTTCTACAGACTG     1200
 1201  ACCATACTGATATCGTGTTCGCCGTTAGCTGGATGCCACTCCACGTCTTCCACGTGGTG     1260
 1261  ACTGACTTCAATGATAACTTGATTTCCAATAGGCATTTCAAGCTGGTATACTGCATCTGT    1320
 1321  CACTTGTTAGGCATGATGTCCTGTTGTCTAAATCCGATCCTATATGTTTCCTTAATAAT     1380
 1381  GGTATCAAAGAGAGAGAAACTTGAGAGACCCTTATCCACATGTCATGATTCTCTCTG   1440
 1441  TGCACCAAAGAGAGAGAAACGTGGTAATTGACACATAATTTATACAGAAGTATTCTGGAT    1501
```

```
   1 GTTCCCTCTGAATAGATTAATTAAAGTAGTCATGTAATGTTTTTGGTTGCTGACAA      60
  61 ATGTCTTTTATTCCAAGCAGGACTATAATATGGATTTAGAGCTCGACGAGTATTAAAC    120
 121 AAGACACTTGCCACAGAGAATAATACTGCTGCCACTCGGAATTCTGATTCTCCCAGTCTGG 180
 181 GATGACTATAAAAGCAGTGTAGATACTTACAGTATATTTCTGATTGGGCTCTATACATTT   240
 241 GTAAGTCTTCTGGCTTTATGGGGAATCTACTTATTTTAATGGCTCTCATGAAAAAGCGT   300
 301 AATCAGAAGACTACGGTAAACTTCCTCATAGCAATCTCGGCCTTTTCTGATATCTTGGTT  360
 361 GTGCTGTTTGCTCACCTTTCACACTGACGTCTGTCTTGCTGATCAGTGGATGTTTGGC    420
 421 AAAGTCATGTGCCATATTATGCCTTTTCTCAGTGTGTGATAAAACATCCCATATCTAATAAT 480
 481 ATTTAATATCAATTGCCATTGCTACTTTCTGATAGCTACTGTCTGGACACTAGGTTTTGCCATC 540
 541 TTAACAGCAAACCATGGCTACTTTCTGTTTCACAGTCTTGTGGAACTTCAAGAAACATTTGGTTCAGCA 600
 601 TGTTCTCCCCTTCCCAGTGTTCACAGTGTATTTATGTCTAGTTGTGAGTCATGGCCATCTGATTCATACAGAATTGCC 660
 661 TTGCTGAGCAGCAGGTATTTATGCTAGTTGTTGAGTCATGGCCATCTGATTCATACAGAATTGCC 720
 721 TTTACTATCTCTTTATTGTCTGCAGAAGTATAACTTAACTCTCTTCAGTTGTCTTACTGTAAGT 780
 781 CATACAAGTGTCTGCAGAAGTCAACTAAATGGAGTTATTCATCCTGCTCCAACAAAAGAGTGGGCCCTCAGGTGAAA 840
 841 GAAAATGAGAGACAGCATGTGTTGATTGTCCAACAAAAGACCTTGTCCAACAAAAGAGAAAACAGAAGATATAGC 900
 901 CTCTCTGGCAGCAGCATGTGTTACCTGCTCCAAGAAGAGTCAGCTCTCTTCATCCAGTAAGTTCATA 960
 961 AAGAAGACAGCATGTGTTACCTGCTCCAAGAAGACCAGCTCTCTTCATCCAGTAAGTTCATA 1020
1021 ATACTTCCAGATCCCCACTGTTCTGTTTGAGATAAAACCTGAAGATAAAATCAGATGTTCATGAATTG 1080
1081 CCAGGGGTCCCCACTGTTCTGTTTGAGATAAAACCTGAAGATAAAATCAGATGTTCATGAATTG 1140
1141 AGAGTAAAACGTTCTGTTACAAGATATTGCTGTGTTAGTTGCTGTGATGCCACTACACCTTTCTACAGACTG 1200
1201 ACCATACTGATATTAGTATTGCTGTGTTAGTTGCTGTGATGCCACTACACCTTTCCATGTGGTA 1260
1261 ACTGATTTTAATGACAATCTTATTTCAAATAGGCATTTCAAGTTGGTATGCATTTGT 1320
1321 CATTTGTTGGGCATGATGTCCTGTTGTCTTAATCAATTCTATTGGGTTTCTTAATAT 1380
1381 GGGATTAAAGCTGATTTAGTGTCCCTTATACACTGTCTTCATATGTAATAATTCTCACTG 1440
1441 TTTACCAAGGAAAGAAC                                              1457
```

| FIGURE 7A |
|-----------|
| FIGURE 7B |
| FIGURE 7C |
| FIGURE 7D |
| FIGURE 7E |

```
  1  ATGGACGTCCTCTTCTTCC.ACCAGGATTCTAGTATGGAGTTTAAGCTTG    50
  1  .....ATGTCTTTTTATTCCAAGCAGGACTATATATGGATTTAGAGCTCG    46

51  AGGAGCATTTTAACAAGACATTTGTCACAGAGAACAATACAGCTGCTGCT   100
 47  ACGAGTATTATAACAAGACACTTGCCACAGAGAATAATACTGCTGCCACT    96

101  CGGAATGCAGCCCTTCCCCTGCCTGGGAGGACTACAGAGAGGCAGCGTAGACGA   150
 97  CGGAATTCTGATTTCCCAGTCTGGGATGACTATGGGACTATAAAAGCAGTGTAGATGA  146

151  TTTACAATACTTTCTGATTGGGCTCTATACATTCGTAAGTCTTCTTGGCT   200
147  CTTACAGTATTTTCTGATTGGGCTCTATACATTTGTAAGTCTTCTTGGCT   196

201  TTATGGGCAATCTACTTATTTTAATGGCTGTGTTATGAAAAAGCGCAATCAG   250
197  TTATGGGGAATCTACTTATTTTAATGGCTCTCATGAAAAAGCGTAATCAG   246
```

FIGURE 7B

```
251 AAGACTACAGTGAACTTTCTCATAGGCAACCTGGCCTTCTCCGACATCTT 300
    ----- ------ ----- ---------- -------- -------
247 AAGACTACGGTAAACTTCCTCATAGGCAATCTGGCCTTTCTGATATCTT 296

301 GGTCGTCCTGTTTTTGCTCCCCTTTCACCCCTGACCTCTGTCTTGTTGGATC 350
    ------ -------- ----- --------- ------ -----
297 GGTTGTGCTGTTTTGCTCACCTTTCACACTGACGTCTGTCTTGCTGGATC 346

351 AGTGGATGTTTGGCAAAGCCATGTGCCATATCATGCCGTTCCTTCAATGT 400
    ------- --------- ------- --------- ---- ------
347 AGTGGATGTTTGGCAAAGTCATGTGCCATATTATGCCTTTTCTTCAATGT 396

401 GTGTCAGTTCTGGTTTCAACTCTGATTTTAATATCAATTGCCATTGTCAG 450
    ------- ------- ------ ------- --------------
397 GTGTCAGTTTTGGTTTCAACTTTAATTTTAATATCAATTGCCATTGTCAG 446

451 GTATCATATGATAAAGCACCCTATTTCTAACAATTTAACGGCAAACCATG 500
    ------- -------- ----- --- --- ----- ----------
447 GTATCATATGATAAAACATCCCATATCTAATAATTTAACAGCAAACCATG 496

501 GCTACTTCCTGATAGCTACTGTCTGGACACTGGGCTTTGCCATCTGTTCT 550
    ------ -------- --------- ------ -------------
497 GCTACTTTCTGATAGCTACTGTCTGGACACTAGGTTTTGCCATCTGTTCT 546
```

FIGURE 7C

```
551 CCCCTCCCAGTGTTTCACAGTCTTGTGGAACTTAAGGAGACCCTTTGGCTC      600
547 CCCCTTCCAGTGTTTCACAGTCTTGTGGAACTTCAAGAAACATTTGGTTC       596

601 AGCACTGCTGAGTAGCAAATATCTCTGTGTTGAGTCATGGCCCTCTGATT       650
597 AGCATTGCTGAGCAGCAGGTATTTATGTTGAGTCATGGCCATCTGATT         646

651 CATACAGAATTGCTTTCACAATCTCTTTATTGCTAGTGCAGTATATCCTG       700
647 CATACAGAATTGCCTTTACTATCTCTTTATTGCTAGTTCAGTATATTCTG       696

701 CCTCTAGTATGTTTAACGGTAAGTCATACCAGCGTCTGCCGAAGCATAAG       750
697 CCCTTAGTTTGTCTTACTGTAAGTCATACAAGTGTCTGCAGAAGTATAAG       746

751 CTGTGGATTGTCCCACAAAGAAAACAGACTCGAAGAAAATGAGATGATCA       800
747 CTGTGGATTGTCCAACAAAGAAAACAGACTTGAAGAAAATGAGATGATCA       796

801 ACTTAACCCTACAGCCATCCAAAAAGAGCAGGAACCAGGCAAAACCCCC        850
797 ACTTAACTCTTCATCCATCCAAAAAGAGTGGGCCTCAGGTGAAACTCTCT       846
```

FIGURE 7D

```
 851 AGCACTCAAAAGTGGAGCTACTCATTCATTCAGAAAGCACAGAAGGAGGTA  900
 847 GGCAGCCATAAATGGAGTTATTCATTCATCAAAAACACAGAAGAAGATA    896

901 CAGCAAGAAGACGGCCTGTCTTACCCGCCCAGCAGGACCTTCCCAGG      950
 897 TAGCAAGAAGACAGCATGTGTGTTACCTGCTCCAGAAAGACCTTCTCAAG   946

951 GGAAGCA....CCTAGCCGTTCCAGAAAATCCAGCCTCCGTCCGTAGCCAG 1000
 947 AGAACCACTCCAGAATACTTCCAGAAAACTTTGGCTCTGTAAGAAGTCAG  996

1001 CTGTCGCCATCCAGTAAGGTCATTCCAGGGGTCCCAATCTGCTTTGAGGT  1050
 997 CTCTCTTCATCCAGTAAGTTCATACCAGGGGTCCCCACTTGCTTTGAGAT 1046

1051 GAAACCTGAAAGAAGCTCAGATGCTCATGAGAGAGTCAAGCGTTCCA     1100
1047 AAAACCTGAAAGAAATTCAGAAAATTCAGATGTTCATGAATTGAGAGTAAAACGTTCTG 1096

1101 TCACTAGAATAAAAAGAGATCTCGAAGTGTTTTCTACAGACTGACCATA   1150
1097 TTACAAGAATAAAAAGAGATCTCGAAGTGTTTTCTACAGACTGACCATA  1146
```

FIGURE 7E

```
1151 CTGATACTCGTGTTCGCCGTTAGCTGGATGCCACTCCACGTCTTCCACGT 1200
     ||| |||| ||||| |||||| ||||||||||||||| || |||||| ||
1147 CTGATATTAGTATTTGCTGTGTTAGTTGGATGCCACTACACCTTTCCATGT 1196

1201 GGTGACTGACTTCAATGATAACTTGATTTCCAATAGGCATTTCAAGCTGG 1250
     |||  |||| ||||||| ||  || ||||| ||||||||||||||| |||
1197 GGTAACTGATTTTAATGACAATCTTATTTCAAATAGGCATTTCAAGTTGG 1246

1251 TATACTGCATCTGTCACTGTTAGGCATGATGTCCTGTTGTCTAAATCCG 1300
     |  |||||||| ||||| |||| ||||||||||| ||||||| ||| ||
1247 TGTATTGCATTTGTCATTTGTTGGGCATGATGATGTCCTGTTGTCTTAATCCA 1296

1301 ATCCTATATATGGTTTCCTTAATAATGGTATCAAAGCAGAGACTTGAGAGCCCT 1350
     ||  ||||| |||||| ||||| ||||| ||| |||  ||  ||| ||| |||
1297 ATTCTATATGGGTTTCTTAATAAAGCTGATTTAAGTGTCCCT 1346

1351 TATCCACTGCCTACACACATGTCA 1372
     ||   ||||||||| |||||||||
1347 TATACACTGTCTTCATATG... 1365
```

FIGURE 7F

| FIGURE 7F |
|---|
| FIGURE 7G |

```
  1 MDVLFFHQDSSMEFKLEEHFNKTFVTENNTAAAARNAAFPAWEDYRGSVDD   50
    ::        .:.  ..:.:  :::.:...:.:...      ::...:::
  1 .MSFYSKQDYNMDLELDEYYNKTLATENNTAATRNSDFPVWDDYKSSVDD   49
                      I                           II
 51 LQYFLIGLYTFVSLLGFMGNLLILMAVMKKRNQKTTVNFLIGNLAFSDIL  100
    |||||||||||||||||||||||||||| ||||||||||||||||||||
 50 LQYFLIGLYTFVSLLGFMGNLLILMALMKKRNQKTTVNFLIGNLAFSDIL   99
                                              III
101 VVLFCSPFTLTSVLLDQWMFGKAMCHIMPFLQCVSVLVSTLILISIAIVR  150
    |||||||||||||||||||||||| |||||||||||||||||||||||||
100 VVLFCSPFTLTSVLLDQWMFGKVMCHIMPFLQCVSVLVSTLILISIAIVR  149
                     IV
151 YHMIKHPISNNLTANHGYFLIATVWTLGFAICSPLPVFHSLVELKETFGS  200
    ||||||||||||||||||||||||||||||||||||||||||||| ||||
150 YHMIKHPISNNLTANHGYFLIATVWTLGFAICSPLPVFHSLVELQETFGS  199
```

FIGURE 7G

```
                                                                V
201 ALLSSKYLCVESWPSDSYRIAFTISLLLVQYILPLVCLTVSHTSVCRSIS           250
200 ALLSSRYLCVESWPSDSYRIAFTISLLLVQYILPLVCLTVSHTSVCRSIS           249

251 CGLSHKENRLEENEMINLTLQPSKKSRNQAKTPSTQKWSYSFIRKHRRY             300
250 CGLSNKENRLEENEMINLTLHPSKKSGPQVKLSGSHKWSYSFIKKHRRY             299

301 SKKTACVLPAPAGPSQGKHLAV.PENPASVRSQLSPSSKVIPGVPICFEV            349
300 SKKTACVLPAPERPSQENHSRILPENFGSVRSQLSSSSKFIPGVPTCFEI            349
                                                          VI
350 KPEESSDAHEMRVKRSITRIKKKRSRSVFYRLTILILVFAVSWMPLHVFHV           399
350 KPEENSDVHELRVKRSVTRIKKKRSRSVFYRLTILILVFAVSWMPLHLFHV           399
                                              VII
400 VTDFNDNLISNRHFKLVYCICHLLGMMSCCLNPILYGFLNNGIKADLRAL            449
400 VTDFNDNLISNRHFKLVYCICHLLGMMSCCLNPILYGFLNNGIKADLVSL            449

450 IHCLHMS    456
450 IHCLHM.    455
```

```
                                                                    V
Y5h  LLS--SRYLCVESUPSD...S.YRIAFTISLLLVQYILPLVCLTVSHTSV            244
Y1h  D.AYK.DKYVCFDQFPSD...S.HRLSYTTLLVLQYFGPLCFIFICYFKI            234
Y2h  IVA.....CTEKWPGEEKSIYGTVYSLSLILYVLPLGIISFSYTRI                242
Y4h  ALEFLADKVVCTESUP...LAHHRTIYTTFLLFQYCLPLGFILVCYARI             237

Y5h  CRSISCGLSNKENRLEENEMINLTLHPSKKSGPQVKLSGSHKWSYSFIKK            294
Y1h  .........................................YI                  236
Y2h  .........................................WSKLKN              248
Y4h  .........................................YR                  239

Y5h  HRRYSKKTACVLPAPERPSQENHSRILPENFGSVRSQLSSSSKFIPGVP             344
Y1h  RLKRRNNMDKMRDNKYRSSE............................              257
Y2h  HVSPGAANDHYHQRRQK...............................              265
Y4h  RLQRQGRVFHK.GTYSLRAGH...........................              259

VI
Y5h  TCFEIKPEENSDVHELRVKRSVTRIKKRSRSVFYRLTILILVFAVSWMPL            394
Y1h  ..................................TKRININLLSIVVAFAVCWLPL     279
Y2h  ....................................TTKMLVCVVVFAVSWLPL       284
Y4h  ....................................MKQVNVLVVHVVAFAVLWLPL    281
```

FIGURE 8C

```
                                              VII
Y5h  HLFHVVTDF NDNLISNRHF KLVYCICHLL GNMSCCLNPI LYGFLNNGIK A  444
Y1h  TIFNTVFDWN HQIIATCNHN NLFLLCNLTA HISTCVNPIF YGFLNKNFQ R  329
Y2h  HAFQLAVDID SQVLDLKEYK LIFTVFHIIA MCSTFANPLL YGWMNSNYR K  334
Y4h  HVFNSLEDWH HEAIPICHGN LIFLVCHLLA MASTCVNPFI YGFLNTNFK K  331

Y5h  DLVSLIH.CL HM........ .......... .......... ..........   455
Y1h  DLQFFNFEDF RSRDDDYETI AMSTMHTDVS KTSLKQASPV AFKKINND     379
Y2h  AFLSAFR.CE QRLDAIHSEV SVTFKAKKNL EVRKNSGPND SFTEATNV.    381
Y4h  EIKALVLTCQ QSAPLEESEH LPLSTVHTEV SKGSLRLSGR SNPI....     375

Y5h  ........ 455
Y1h  DNEKI... 384
Y2h  ........ 365
Y4h  ........ 375
```

DNA ENCODING A HYPOTHALAMIC ATYPICAL NEUROPEPTIDE Y/PEPTIDE YY RECEPTOR (Y5) AND USES THEREOF

BACKGROUND OF THE INVENTION

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the sequence listing and the claims.

Neuropeptide Y (NPY) is a member of the pancreatic polypeptide family with widespread distribution throughout the mammalian nervous system. NPY and its relatives (peptide YY or PYY, and pancreatic polypeptide or PP) elicit a broad range of physiological effects through activation of at least five G protein-coupled receptor subtypes known as Y1, Y2, Y3, Y4 (or PP), and the "atypical Y1". The role of NPY as the most powerful stimulant of feeding behavior yet described is thought to occur primarily through activation of the hypothalamic "atypical Y1" receptor. This receptor is unique in that its classification was based solely on feeding behavior data, rather than radioligand binding data, unlike the Y1, Y2, Y3, and Y4 (or PP) receptors, each of which were described previously in both radioligand binding and functional assays. Applicants now report the use of a $^{125}$I-PYY-based expression cloning technique to isolate a rat hypothalamic cDNA encoding an "atypical Y1" receptor referred to herein as the Y5 subtype. Applicants also report the isolation and characterization of a Y5 homolog from human hippocampus. Protein sequence analysis reveals that the Y5 receptor belongs to the G protein-coupled receptor superfamily. Both the human and rat homolog display ≦42% identity in transmembrane domains with the previously cloned "Y-type" receptors. Rat brain localization studies using in situ hybridization techniques verified the existence of Y5 receptor mRNA in rat hypothalamus. Pharmacological evaluation revealed the following similarities between the Y5 and the "atypical Y1" receptor. 1) Peptides bound to the Y5 receptor with a rank order of potency identical to that described for the feeding response: NPY≧NPY$_{2-36}$=PYY=[Leu$^{31}$, pro$^{34}$]NPY>>NPY$_{13-36}$. 2) The Y5 receptor was negatively coupled to cAMP accumulation, as had been proposed for the "atypical Y1" receptor. 3) Peptides activated the Y5 receptor with a rank order of potency identical to that described for the feeding response. 4) The reported feeding "modulator" [D-Trp$^{32}$]NPY bound selectively to the Y5 receptor and subsequently activated the receptor. 5) Both the Y5 and the "atypical Y1" receptors were sensitive to deletions or modifications in the midregion of NPY and related peptide ligands. These data support the identity of the Y5 receptor as the previously described "atypical Y1", and furthermore indicate a role for the Y5 receptor as a potential target in the treatment of obesity, metabolism, and appetite disorders.

The peptide neurotransmitter neuropeptide Y (NPY) is a 36 amino acid member of the pancreatic polypeptide family with widespread distribution throughout the mammalian nervous system. NPY is considered to be the most powerful stimulant of feeding behavior yet described (Clark et al., 1984; Levine and Morley, 1984; Stanley and Leibowitz, 1984). Direct injection into the hypothalamus of satiated rats, for example, can increase food intake up to 10-fold over a 4-hour period (Stanley et al., 1992). The role of NPY in normal and abnormal eating behavior, and the ability to interfere with NPY-dependent pathways as a means to appetite and weight control, are areas of great interest in pharmacological and pharmaceutical research (Sahu and Kalra, 1993; Dryden et al., 1994). Any credible means of studying or controlling NPY-dependent feeding behavior, however, must necessarily be highly specific as NPY can act through at least 5 pharmacologically defined receptor subtypes to elicit a wide variety of physiological functions (Dumont et al., 1992). It is therefore vital that knowledge of the molecular biology and structural diversity of the individual receptor subtypes be understood as part of a rational drug design approach to develop subtype selective compounds. A brief review of NPY receptor pharmacology is summarized below and also in Table 1.

TABLE 1: Pharmacologically defined receptors for NPY and related pancreatic polypeptides.

Rank orders of affinity for key peptides (NPY, PYY, PP, [Leu$^{31}$, Pro$^{34}$]NPY, NPY$_{2-36}$, and NPY$_{13-36}$) are based on previously reported binding and functional data (Schwartz et al., 1990; Wahlestedt et al., 1991; Dumont et al., 1992; Wahlestedt and Reis, 1993). Data for the Y2 receptor were disclosed in U.S. patent application Ser. No. 08/192,288 filed on Feb. 3, 1994, U.S. Pat. No. 5,545,549, the foregoing contents of which are hereby incorporated by reference. Data for the Y4 receptor were disclosed in U.S. patent application Ser. No. 08/176,412 filed on Dec. 28 1993, U.S. Pat. No. 5,516,653, the foregoing contents of which are hereby incorporated by reference. Missing peptides in the series reflect a lack of published information.

TABLE 1

| Receptor | Affinity (pK$_i$ or pEC$_{50}$) | | | | | |
|---|---|---|---|---|---|---|
| | 11 to 10 | 10 to 9 | 9 to 8 | 8 to 7 | 7 to 6 | <6 |
| Y1 | NPY<br>PYY<br>[Leu$^{31}$, Pro$^{34}$]NPY | | NPY$_{2-36}$ | NPY$_{13-36}$ | PP | |
| Y2 | | PYY<br>NPY<br>NPY$_{2-36}$ | NPY$_{13-36}$ | | | [Leu$^{31}$, Pro$^{34}$]NPY<br>PP |
| Y3 | | NPY | [Pro$^{34}$]NPY | NPY$_{13-36}$<br>PP | | PYY |
| Y4 | PP | PYY<br>[Leu$^{31}$, Pro$^{34}$]NPY | NPY<br>NPY$_{2-36}$ | NPY$_{13-36}$ | | |
| atypical | | PYY | | NPY$_{13-36}$ | | |

TABLE 1-continued

| | Affinity (pK$_i$ or pEC$_{50}$) | | | | | |
|---|---|---|---|---|---|---|
| Receptor | 11 to 10 | 10 to 9 | 9 to 8 | 8 to 7 | 7 to 6 | <6 |
| Y1 (feeding) | | NPY NPY$_{2-36}$ [Leu$^{31}$, Pro$^{34}$] NPY | | | | |

NPY Receptor Pharmacology

NPY receptor pharmacology has historically been based on structure/activity relationships within the pancreatic polypeptide family. The entire family includes the namesake pancreatic polypeptide (PP), synthesized primarily by endocrine cells in the pancreas; peptide YY (PYY), synthesized primarily by endocrine cells in the gut; and NPY, synthesized primarily in neurons (Michel, 1991; Dumont et al., 1992; Wahlestedt and Reis, 1993). All pancreatic polypeptide family members share a compact structure involving a "PP-fold" and a conserved C-terminal hexapeptide ending in Tyr$^{36}$ (or Y$^{36}$ in the single letter code). The striking conservation of y$^{36}$ has prompted the reference to the pancreatic polypeptides' receptors as "Y-type" receptors (Wahlestedt et al., 1987), all of which are proposed to function as seven transmembrane-spanning G protein-coupled receptors (Dumont et al., 1992).

The Y1 receptor recognizes NPY≧PYY>>PP (Grundemar et al., 1992). The receptor requires both the N- and the C-terminal regions of the peptides for optimal recognition. Exchange of Gln$^{34}$ in NPY or PYY with the analogous residue from PP (Pro$^{34}$), however, is well-tolerated. The Y1 receptor has been cloned from a variety of species including human, rat and mouse (Larhammar et al, 1992; Herzog et al, 1992; Eva et al, 1990; Eva et al, 1992). The Y2 receptor recognizes PYY~NPY>>PP and is relatively tolerant of N-terminal deletion (Grundemar et al., 1992). The receptor has a strict requirement for structure in the C-terminus (Arg$^{33}$-Gln$^{34}$-Arg$^{35}$-Tyr$^{36}$-NH$_2$); exchange of Gln$^{34}$ with Pro$^{34}$, as in PP, is not well tolerated. The Y2 receptor has recently been cloned (disclosed in U.S. patent application Ser. No. 08/192,288, filed on Feb. 3, 1994 U.S. Pat. No. 5,545,549. The Y3 receptor is characterized by a strong preference for NPY over PYY and PP (Wahlestedt et al., 1991). [Pro$^{34}$]NPY is reasonably well tolerated even though PP, which also contains Pro$^{34}$, does not bind well to the Y3 receptor. This receptor (Y3) has not yet been cloned. The Y4 receptor (disclosed in U.S. patent application Ser. No. 08/176,412, filed on Dec. 28 1993 U.S. Pat. No. 5,576,653, binds PP>PYY>NPY. Like the Y1, the Y4 requires both the N- and the C-terminal regions of the peptides for optimal recognition (Synaptic Y4 patent). The "atypical Y1" or "feeding" receptor was defined exclusively by injection of several pancreatic polypeptide analogs into the paraventricular nucleus of the rat hypothalamus which stimulated feeding behavior with the following rank order: NPY$_{2-36}$≧NPY~PYY~[Leu$^{31}$, Pro$^{34}$]NPY>NPY$_{13-36}$ (Kalra et al., 1991; Stanley et al., 1992). The profile is similar to that of a Y1-like receptor except for the anomalous ability of NPY$_{2-36}$ to stimulate food intake with potency equivalent or better than that of NPY. A subsequent report in J. Med. Chem. by Balasubramaniam and co-workers (1994) showed that feeding can be regulated by [D-Trp$^{32}$]NPY. While this peptide was presented as an NPY antagonist, the published data at least in part support a stimulatory effect of [D-Trp$^{32}$]NPY on feeding. [D-Trp$^{32}$]NPY thereby represents another diagnostic tool for receptor identification. In contrast to other NPY receptor subtypes, the "feeding" receptor has never been characterized for peptide binding affinity in radioligand binding assays and the fact that a single receptor could be responsible for the feeding response has been impossible to validate in the absence of an isolated receptor protein; the possibility exists, for example, that the feeding response could be a composite profile of Y1 and Y2 subtypes.

Applicants now report the isolation by expression cloning of a novel Y-type receptor from a rat hypothalamic cDNA library, along with its pharmacological characterization, in situ localization, and human homolog. The data provided link this newly-cloned receptor subtype, from now on referred to as the Y5 subtype, to the "atypical Y1" feeding response. This discovery therefore provides a novel approach, through the use of heterologous expression systems, to develop a subtype selective antagonist for obesity and other indications.

BRIER DESCRIPTION OF THE FIGURES

FIG. 1 Competitive displacement of $^{125}$I-PYY on membranes from rat hypothalamus. Membranes were incubated with $^{125}$I-PYY and increasing concentrations of peptide competitors. IC$_{50}$ values corresponding to 50% displacement were determined by nonlinear regression analysis. Data are representative of at least two independent experiments. IC$_{50}$ values for these compounds are listed separately in Table 2.

FIG. 2 Competitive displacement of $^{125}$I-PYY$_{3-36}$ on membranes from rat hypothalamus. Membranes were incubated with $^{125}$I-PYY$_{3-36}$ and increasing concentrations of peptide competitors. IC$_{50}$ values corresponding to 50% displacement were determined by nonlinear regression analysis. Data are representative of at least two independent experiments. IC$_{50}$ values for these compounds are listed separately in Table 2.

FIG. 3 Nucleotide sequence of the rat hypothalamic Y5 cDNA clone (Seq. I.D. No 1). Initiation and stop codons are underlined. Only partial 5' and 3' untranslated sequences are shown.

FIG. 4 Corresponding amino acid sequence of the rat hypothalamic Y5 cDNA clone (Seq. I.D. No. 2).

FIG. 5 Nucleotide sequence of the human hippocampal Y5 cDNA clone (Seq. I.D. No. 3). Initiation and stop codons are underlined. Only partial 5' and 3' untranslated sequences are shown.

FIG. 6 Corresponding amino acid sequence of the human hippocampal Y5 cDNA clone (Seq. I.D. No. 4).

FIGS. 7A–7G Comparison of coding nucleotide sequences between rat hypothalamic Y5 (top row) and human hippocampal Y5 (bottom row) cDNA clones (84.1% nucleotide identity). FIGS. 7F–7G. Comparison of deduced amino acid sequences between rat hypothalamic Y5 (top row) and human hippocampal Y5 (top row) cDNA clones (87.2% overall and 98.8% transmembrane domain identities).

FIGS. 8A–8C Comparison of the human Y5 receptor deduced amino acid sequence with those of the human Y1, Y2, Y4 sequences. Solid bars, the seven putative membrane-spanning domains (TM I-VII). Shading, identities between receptor sequences.

FIG. 9 Equilibrium binding of $^{125}$I-PYY to membranes from COS-7 cells transiently expressing rat Y5 receptors. Membranes were incubated with $^{125}$-PYY for the times indicated, in the presence or absence of 300 nM human NPY. Specific binding, B, was plotted against time, t, to obtain the maximum number of equilibrium binding sites, $B_{max}$, and observed association rate, $K_{obs}$, according to the equation, $B = B_{max} * (1-e^{-(kobs\ *t)})$. Binding is shown as the percentage of total equilibrium binding, $B_{max}$, determined by nonlinear regression analysis. Each point represents a triplicate determination.

FIG. 10 Saturable equilibrium binding of $^{125}$I-PYY to membranes from COS-7 cells transiently expressing rat Y5 receptors. Membranes were incubated with $^{125}$I-PYY ranging in concentration from 0.4 pM to 2.7 nM, in the presence or absence of 300 nM human NPY. Specific binding, B, was plotted against the free $^{125}$I-PYY concentration, [L], to obtain the maximum number of saturable binding sites, $B_{max}$, and the $^{125}$I-PYY equilibrium dissociation constant, $K_d$, according to the binding isotherm, $B=B_{max}[L]/([L]+K_d)$. Specific binding is shown. Data are representative of three independent experiments, with each point measured in triplicate.

FIG. 11 Competitive displacement of $^{125}$I-PYY from COS-7 cells transiently expressing rat Y5 receptors. Membranes were incubated with $^{125}$I-PYY and increasing concentrations of peptide competitors. $IC_{50}$ values corresponding to 50% displacement were determined by nonlinear regression analysis and converted to $K_i$ values according to the equation, $K_i = IC_{50}/(1+[L]/K_d)$, where [L] is the $^{125}$I-PYY concentration and $K_d$ is the equilibrium dissociation constant of $^{125}$I-PYY. Data are representative of at least two independent experiments. Rank orders of affinity for these and other compounds are listed separately in Table 4.

FIG. 12 Inhibition of forskolin-stimulated cAMP accumulation in intact 293 cells stably expressing rat Y5 receptors. Functional data were derived from radioimmunoassay of cAMP in 293 cells stimulated with 10 μM forskolin over a 5 minute period. Rat/human NPY was tested for agonist activity at concentrations ranging from 0.03 pM to 0.3 μM over the same period. The $EC_{50}$ value corresponding to 50% maximal activity was determined by nonlinear regression analysis. The data shown are representative of three independent experiments.

FIG. 13A–13H Schematic diagrams of coronal sections through the rat brain, illustrating the distribution of NPY Y5 receptor mRNA, as visualized microscopically in sections dipped in liquid emulsion. The sections are arranged from rostral (A) to caudal (H). Differences in silver grain density over individual neurons in a given area are indicated by the hatching gradient. The full definitions for the abbreviations are as follows:

Aco=anterior cortical amygdaloid nucleus;
AD=anterodorsal thalamic nucleus;
APT=anterior pretectal nucleus;
Arc=arcuate hypothalamic nucleus;
BLA=basolateral amygdaloid nucleus anterior;
CA3=field CA3 of Ammon's horn, hippocampus;
CeA=central amygdaloid nucleus;
Cg=cingulate cortex;
CL=centrolateral thalamic nucleus;
CM=central medial thalamic nucleus
DG=dentate gyrus, hippocampus;
DMH=dorsomedial hypothalamic nucleus;
DR=dorsal raphe;
GiA=gigantocellular reticular nucleus, alpha;
HDB=nucleus horizontal limb diagonal band;
InG=intermediate gray layer superior colliculus;
LC=locus coeruleus;
LH=lateral hypothalamic area;
MePV=medial amygdaloid nucleus, posteroventral;
MVe=medial vestibular nucleus;
MHb=medial habenular nucleus;
PAG=periaqueductal gray;
PaS=parasubiculum;
PC=paracentral thalamic nucleus;
PCRtA=parvocellular reticular nucleus, alpha;
Pe=periventricular hypothalamic nucleus;
PrS=presubiculum;
PN=pontine nuclei;
PVH=paraventricular hypothalamic nucleus;
PVHmp=paraventricular hypothalamic nucleus, medial parvicellular part
PVT=paraventricular thalamic nucleus;
Re=reunions thalamic nucleus;
RLi=rostral linear nucleus raphe;
RSG=retrosplenial cortex;
SNc=substantia nigra, pars compacta; and
SON=supraoptic nucleus.

DETAILED DESCRIPTION OF THE INVENTION

Figure 1:
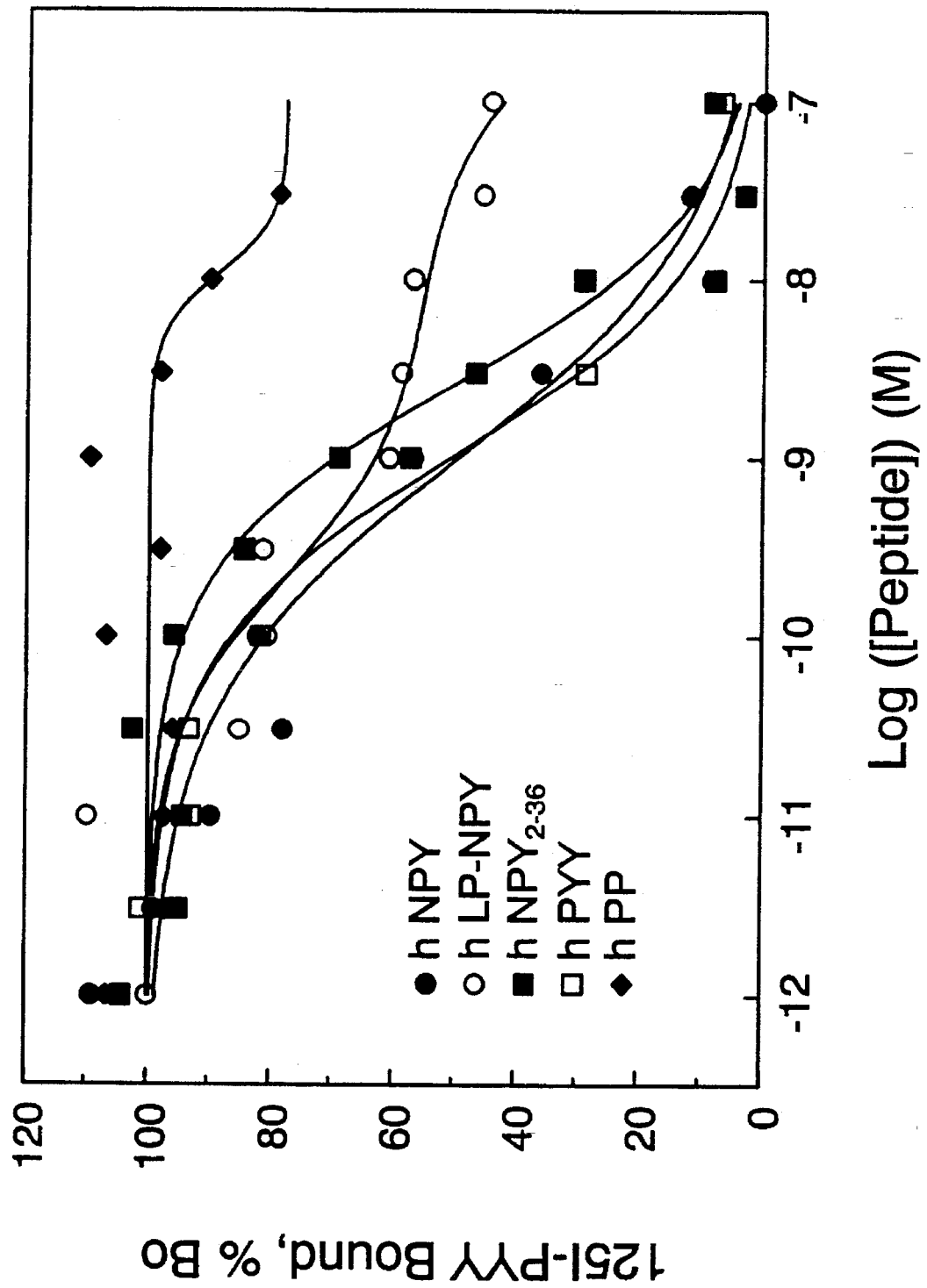

Throughout this application, the following standard abbreviations are used to indicate specific nucleotide bases:

| | |
|---|---|
| C = cytosine | A = adenine |
| T = thymine | G = guanine |

This invention provides an isolated nucleic acid molecule encoding a Y5 receptor. In an embodiment, the isolated nucleic acid molecule encodes a receptor being characterized by an amino acid sequence in the transmembrane region, which amino acid sequence has 60% homology or higher to the amino acid sequence in the transmembrane region of the human Y5 receptor shown in FIG. 6. In another embodiment, the Y5 receptor has substantially the same amino acid sequence as described in FIG. 4. In another embodiment, the Y5 receptor has substantially the same amino acid sequence as described in FIG. 6.

This invention provides the above-described isolated nucleic acid molecule, wherein the nucleic acid molecule is a DNA molecule. In an embodiment, the DNA molecule is a cDNA molecule. In another embodiment, the DNA molecule is a genomic DNA molecule. In still another embodiment, the nucleic acid molecule is an RNA molecule. In a separate embodiment, the nucleic acid molecule encodes a human Y5 receptor. In an embodiment, the human Y5 receptor has the amino acid sequence as described in FIG. 6.

This invention also encompasses DNAs and cDNAs which encode amino acid sequences which differ from those of Y5 receptor, but which should not produce phenotypic changes. Alternatively, this invention also encompasses DNAs and cDNAs which hybridize to the DNA and cDNA of the subject invention. Hybridization methods are well known to those of skill in the art.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The DNA molecules described and claimed herein are useful for the information which they provide concerning the amino acid sequence of the polypeptide and as products for the large scale synthesis of the polypeptide by a variety of recombinant techniques. The molecule is useful for generating new cloning and expression vectors, transformed and transfected prokaryotic and eukaryotic host cells, and new and useful methods for cultured growth of such host cells capable of expression of the polypeptide and related products.

In a separate embodiment, the nucleic acid molecule encodes a rat Y5 receptor. In another embodiment, the rat Y5 receptor has the amino acid sequence shown in FIG. 4.

This invention also provides an isolated Y5 receptor protein.

This invention provides a vector comprising the above-described nucleic acid molecule.

Vectors which comprise the isolated nucleic acid molecule described hereinabove also are provided. Suitable vectors comprise, but are not limited to, a plasmid or a virus. These vectors may be transformed into a suitable host cell to form a host cell vector system for the production of a polypeptide having the biological activity of a Y5 receptor.

This invention provides the above-described vector adapted for expression in a bacterial cell which further comprises the regulatory elements necessary for expression of the nucleic acid molecule in the bacterial cell operatively linked to the nucleic acid molecule encoding the Y5 receptor as to permit expression thereof.

This invention provides the above-described vector adapted for expression in a yeast cell which comprises the regulatory elements necessary for expression of the nucleic acid molecule in the yeast cell operatively linked to the nucleic acid molecule encoding the Y5 receptor as to permit expression thereof.

This invention provides the above-described vector adapted for expression in an insect cell which comprises the regulatory elements necessary for expression of the nucleic acid molecule in the insect cell operatively linked to the nucleic acid molecule encoding the Y5 receptor as to permit expression thereof.

In an embodiment, the vector is adapted for expression in a mammalian cell which comprises the regulatory elements necessary for expression of the DNA in the mammalian cell operatively linked to the DNA encoding the mammalian Y5 receptor as to permit expression thereof.

In a further embodiment, the vector is adapted for expression in a mammalian cell which comprises the regulatory elements necessary for expression of the DNA in the mammalian cell operatively linked to the DNA encoding the human Y5 receptor as to permit expression thereof.

In a still further embodiment, the plasmid is adapted for expression in a mammalian cell which comprises the regulatory elements necessary for expression of the DNA in the mammalian cell operatively linked to the DNA encoding the rat Y5 receptor as to permit expression thereof.

This invention provides the above-described plasmid adapted for expression in a mammalian cell which comprises the regulatory elements necessary for expression of DNA in a mammalian cell operatively linked to the DNA encoding the mammalian Y5 receptor as to permit expression thereof.

This invention provides a plasmid which comprises the regulatory elements necessary for expression of DNA in a mammalian cell operatively linked to the DNA encoding the human Y5 receptor as to permit expression thereof designated pcEXV-hY5 (ATCC Accession No. 75943).

This plasmid (pcEXV-hY5) was deposited on Nov. 4, 1994 with the American Type Culture Collection (ATCC), 12301 Parklawn Drive, Rockville, Md. 20852, U.S.A. under the provisions of the Budapest Treaty for the International Recognition of the Deposit of Microorgansims for the Purposes of Patent Procedure and was accorded ATCC Accession No. 75943.

This invention provides a plasmid which comprises the regulatory elements necessary for expression of DNA in a mammalian cell operatively linked to the DNA encoding the rat Y5 receptor as to permit expression thereof designated pcEXV-rY5 (ATCC Accession No. 75944).

This plasmid (pcEXV-rY5) was deposited on Nov. 4, 1994 with the American Type Culture Collection (ATCC), 12301 Parklawn Drive, Rockville, Md. 20852, U.S.A. under the provisions of the Budapest Treaty for the International Recognition of the Deposit of Microorgansims for the Purposes of Patent Procedure and was accorded ATCC Accession No. CRL 75944.

This invention provides a mammalian cell comprising the above-described plasmid or vector. In an embodiment, the mammalian cell is a COS-7 cell.

In another embodiment, the mammalian cell is a 293 human embryonic kidney cell designated 293-rY5-14 (ATCC Accession No. CRL 11757).

This cell (293-rY5-14) was deposited on Nov. 4, 1994 with the American Type Culture Collection (ATCC), 12301 Parklawn Drive, Rockville, Md. 20852, U.S.A. under the provisions of the Budapest Treaty for the International Recognition of the Deposit of Microorgansims for the Purposes of Patent Procedure and was accorded ATCC Accession No. CRL 11757.

This invention provides a nucleic acid probe comprising a nucleic acid molecule of at least 15 nucleotides capable of specifically hybridizing with a unique sequence included within the sequence of a nucleic acid molecule encoding a Y5 receptor. In an embodiment, the nucleic acid is DNA.

This nucleic acid molecule produced can either be DNA or RNA. As used herein, the phrase "specifically hybridizing" means the ability of a nucleic acid molecule to recognize a nucleic acid sequence complementary to its own and to form double-helical segments through hydrogen bonding between complementary base pairs.

This nucleic acid molecule of at least 15 nucleotides capable of specifically hybridizing with a sequence of a nucleic acid molecule encoding the human Y5 receptors can be used as a probe. Nucleic acid probe technology is well known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encodes the Y5 receptor into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the DNA molecule which encodes the Y5 receptor downstream of a bacteriophage promoter such as T3, T7 or SP6. Large amounts of RNA probe may be produced by incubating the labeled nucleotides with the linearized fragment where it contains an upstream promoter in the presence of the appropriate RNA polymerase.

This invention also provides a nucleic acid molecule of at least 15 nucleotides capable of specifically hybridizing with a sequence of a nucleic acid molecule which is complementary to the mammalian nucleic acid molecule encoding a Y5 receptor. This molecule may either be a DNA or RNA molecule.

This invention provides an antisense oligonucleotide having a sequence capable of specifically hybridizing to an mRNA molecule encoding a Y5 receptor so as to prevent translation of the mRNA molecule.

This invention provides an antisense oligonucleotide having a sequence capable of specifically hybridizing to the genomic DNA molecule of Y5 receptor.

This invention provides an antisense oligonucleotide of Y5 receptor comprising chemical analogues of nucleotides.

This invention provides an antibody directed to a Y5 receptor. This invention also provides an antibody directed to a human Y5 receptor.

This invention provides a monoclonal antibody directed to an epitope of a human Y5 receptor present on the surface of a Y5 receptor expressing cell.

This invention provides a pharmaceutical composition comprising an amount of the oligonucleotide effective to reduce activity of a human Y5 receptor by passing through a cell membrane and binding specifically with mRNA encoding a human Y5 receptor in the cell so as to prevent its translation and a pharmaceutically acceptable carrier capable of passing through a cell membrane. In an embodiment, the oligonucleotide is coupled to a substance which inactivates mRNA. In another embodiment, the substance which inactivates mRNA is a ribozyme.

This invention provides the above-described pharmaceutical composition, wherein the pharmaceutically acceptable carrier capable of passing through a cell membrane comprises a structure which binds to a receptor specific for a selected cell type and is thereby taken up by cells of the selected cell type.

This invention provides a pharmaceutical composition comprising an amount of an antagonist effective to reduce the activity of a human Y5 receptor and a pharmaceutically acceptable carrier.

This invention provides a pharmaceutical composition comprising an amount of an agonist effective to increase activity of a Y5 receptor and a pharmaceutically acceptable carrier.

This invention provides the above-described pharmaceutical composition which comprises an amount of the antibody effective to block binding of a ligand to the Y5 receptor and a pharmaceutically acceptable carrier.

As used herein, "pharmaceutically acceptable carriers" means any of the standard pharmaceutically acceptable carriers. Examples include, but are not limited to, phosphate buffered saline, physiological saline, water and emulsions, such as oil/water emulsions.

This invention provides a transgenic nonhuman mammal expressing DNA encoding a human Y5 receptor.

This invention provides a transgenic nonhuman mammal comprising a homologous recombination knockout of the native Y5 receptor.

This invention provides a transgenic nonhuman mammal whose genome comprises antisense DNA complementary to DNA encoding a human Y5 receptor so placed as to be transcribed into antisense mRNA which is complementary to mRNA encoding a Y5 receptor and which hybridizes to mRNA encoding a Y5 receptor thereby reducing its translation.

This invention provides the above-described transgenic nonhuman mammal, wherein the DNA encoding a human Y5 receptor additionally comprises an inducible promoter.

This invention provides the transgenic nonhuman mammal, wherein the DNA encoding a human Y5 receptor additionally comprises tissue specific regulatory elements.

In an embodiment, the transgenic nonhuman mammal is a mouse.

Animal model systems which elucidate the physiological and behavioral roles of Y5 receptor are produced by creating transgenic animals in which the activity of the Y5 receptor is either increased or decreased, or the amino acid sequence of the expressed Y5 receptor is altered, by a variety of techniques. Examples of these techniques include, but are not limited to: 1) Insertion of normal or mutant versions of DNA encoding a Y5 receptor, by microinjection, electroporation, retroviral transfection or other means well known to those skilled in the art, into appropriate fertilized embryos in order to produce a transgenic animal or 2) Homologous recombination of mutant or normal, human or animal versions of these genes with the native gene locus in transgenic animals to alter the regulation of expression or the structure of these Y5 receptor sequences. The technique of homologous recombination is well known in the art. It replaces the native gene with the inserted gene and so is useful for producing an animal that cannot express native Y5 receptors but does express, for example, an inserted mutant Y5 receptor, which has replaced the native Y5 receptor in the animal's genome by recombination, resulting in underexpression of the transporter. Microinjection adds genes to the genome, but does not remove them, and so is useful for producing an animal which expresses its own and added Y5 receptors, resulting in overexpression of the Y5 receptors.

One means available for producing a transgenic animal, with a mouse as an example, is as follows: Female mice are mated, and the resulting fertilized eggs are dissected out of their oviducts. The eggs are stored in an appropriate medium such as M2 medium. DNA or cDNA encoding a Y5 receptor is purified from a vector by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

This invention also provides a method for determining whether a ligand can specifically bind to a Y5 receptor which comprises contacting a cell transfected with and expressing DNA encoding the Y5 receptor with the ligand under conditions permitting binding of ligands to such receptor, detecting the presence of any such ligand specifically bound to the Y5 receptor, and thereby determining whether the ligand specifically binds to the Y5 receptor.

This invention provides a method for determining whether a ligand can specifically bind to a human Y5 receptor which comprises contacting a cell transfected with and expressing DNA encoding the human Y5 receptor with the ligand under conditions permitting binding of ligands to such receptor, detecting the presence of any such ligand specifically bound to the human Y5 receptor, and thereby determining whether the ligand specifically binds to the human Y5 receptor.

This invention provides a method for determining whether a ligand can specifically bind to a human Y5 receptor which comprises contacting a cell transfected with and expressing DNA encoding the human Y5 receptor with the ligand under conditions permitting binding of ligands to such receptor, detecting the presence of any such ligand specifically bound to the human Y5 receptor, and thereby determining whether the ligand specifically binds to the human Y5 receptor, such human Y5 receptor having substantially the same amino acid sequence shown in FIG. 6.

This invention provides a method for determining whether a ligand can specifically bind to a Y5 receptor which comprises contacting a cell transfected with and expressing DNA encoding the Y5 receptor with the ligand under conditions permitting binding of ligands to such receptor, detecting the presence of any such ligand specifically bound to the Y5 receptor, and thereby determining whether the ligand specifically binds to the Y5 receptor, such Y5 receptor being characterized by an amino acid sequence in the transmembrane region having 60% homology or higher to the amino acid sequence in the transmembrane region of the Y5 receptor shown in FIG. 6.

This invention provides a method for determining whether a ligand can specifically bind to a Y5 receptor which comprises preparing a cell extract from cells transfected with and expressing DNA encoding the Y5 receptor, isolating a membrane fraction from the cell extract, contacting the membrane fraction with the ligand under conditions permitting binding of ligands to such receptor, detecting the presence of the ligand specifically bound to the Y5 receptor, and thereby determining whether the ligand specifically binds to the Y5 receptor.

This invention provides a method for determining whether a ligand can specifically bind to a human Y5 receptor which comprises preparing a cell extract from cells transfected with and expressing DNA encoding the human Y5 receptor, isolating a membrane fraction from the cell extract, contacting the membrane fraction with the ligand under conditions permitting binding of ligands to the human Y5 receptor, detecting the presence of the ligand specifically bound to the human Y5 receptor, and thereby determining whether the ligand can specifically bind to the human Y5 receptor.

This invention provides a method for determining whether a ligand can specifically bind to a human Y5 receptor which comprises preparing a cell extract from cells transfected with and expressing DNA encoding the human Y5 receptor, isolating a membrane fraction from the cell extract, contacting the membrane fraction with the ligand under conditions permitting binding of ligands to the human Y5 receptor, detecting the presence of the ligand specifically bound to the human Y5 receptor, and thereby determining whether the ligand can specifically bind to the human Y5 receptor, such human Y5 receptor having substantially the same amino acid sequence shown in FIG. 6.

This invention provides a method for determining whether a ligand can specifically bind to a Y5 receptor which comprises preparing a cell extract from cells transfected with and expressing DNA encoding the Y5 receptor, isolating a membrane fraction from the cell extract, contacting the membrane fraction with the ligand under conditions permitting binding of ligands to the Y5 receptor, detecting the presence of the ligand specifically bound to the Y5 receptor, and thereby determining whether the ligand can specifically bind to the Y5 receptor, such Y5 receptor being characterized by an amino acid sequence in the transmembrane region having 60% homology or higher to the amino acid sequence in the transmembrane region of the Y5 receptor shown in FIG. 6.

This invention provides a method for determining whether a ligand is a Y5 receptor agonist which comprises contacting a cell transfected with and expressing a Y5 receptor with the ligand under conditions permitting activation of a functional Y5 receptor response, detecting a functional increase in Y5 receptor activity, and thereby determining whether the ligand is a Y5 receptor agonist.

This invention provides a method for determining whether a ligand is a human Y5 receptor agonist which comprises contacting a cell transfected with and expressing a human Y5 receptor with the ligand under conditions permitting activation of a functional human Y5 receptor response, detecting a functional increase in human Y5 receptor activity, and thereby determining whether the ligand is a human Y5 receptor agonist.

This invention provides a method for determining whether a ligand is a Y5 receptor antagonist which comprises contacting a cell transfected with and expressing DNA encoding a Y5 receptor with the ligand in the presence of a known Y5 receptor agonist, such as PYY or NPY, under conditions permitting the activation of a functional Y5 receptor response, detecting a decrease in Y5 receptor activity, and thereby determining whether the ligand is a Y5 receptor antagonist.

This invention provides a method for determining whether a ligand is a human Y5 receptor antagonist which comprises contacting a cell transfected with and expressing DNA encoding a human Y5 receptor with the ligand in the presence of a known Y5 receptor agonist, such as PYY or NPY, under conditions permitting the activation of a functional Y5 receptor response, detecting a decrease in human Y5 receptor activity, and thereby determining whether the ligand is a human Y5 receptor antagonist.

In an embodiment of the above-described methods, the cell is non-neuronal in origin. In a further embodiment, the non-neuronal cell is a COS-7 cell, 293 human embryonic kidney cell, NIH-3T3 cell or L-M(TK-) cell.

In one embodiment of the above-described methods, the ligand is not previously known.

This invention provides a Y5 receptor agonist detected by the above-described method. This invention provides a Y5 receptor antagonist detected by the above-described method.

This invention provides a method of screening drugs to identify drugs which specifically bind to a Y5 receptor on the surface of a cell which comprises contacting a cell transfected with and expressing DNA encoding a Y5 receptor with a plurality of drugs under conditions permitting binding of drugs to the Y5 receptor, determining those drugs which specifically bind to the transfected cell, and thereby identifying drugs which specifically bind to the Y5 receptor.

This invention provides a method of screening drugs to identify drugs which specifically bind to a human Y5 receptor on the surface of a cell which comprises contacting a cell transfected with and expressing DNA encoding a human Y5 receptor with a plurality of drugs under conditions permitting binding of drugs to the human Y5 receptor, determining those drugs which specifically bind to the transfected cell, and thereby identifying drugs which specifically bind to the human Y5 receptor.

This invention provides a method of screening drugs to identify drugs which act as agonists of a Y5 receptor which comprises contacting a cell transfected with and expressing DNA encoding a Y5 receptor with a plurality of drugs under conditions permitting the activation of a functional Y5 receptor response, determining those drugs which activate such receptor in the cell, and thereby identify drugs which act as Y5 receptor agonists.

This invention provides a method of screening drugs to identify drugs which act as agonists of a human Y5 receptor which comprises contacting a cell transfected with and expressing DNA encoding a human Y5 receptor with a plurality of drugs under conditions permitting the activation of a functional human Y5 receptor response, determining those drugs which activate such receptor in the cell, and thereby identify drugs which act as human Y5 receptor agonists.

This invention provides a method of screening drugs to identify drugs which act as Y5 receptor antagonists which comprises contacting cells transfected with and expressing DNA encoding a Y5 receptor with a plurality of drugs in the presence of a known Y5 receptor agonist, such as PYY or NPY, under conditions permitting the activation of a functional Y5 receptor response, determining those drugs which inhibit the activation of the receptor in the mammalian cell, and thereby identifying drugs which act as Y5 receptor antagonists.

This invention provides a method of screening drugs to identify drugs which act as human Y5 receptor antagonists which comprises contacting cells transfected with and expressing DNA encoding a human Y5 receptor with a plurality of drugs in the presence of a known human Y5 receptor agonist, such as PYY or NPY, under conditions permitting the activation of a functional human Y5 receptor response, determining those drugs which inhibit the activation of the receptor in the mammalian cell, and thereby identifying drugs which act as human Y5 receptor antagonists. In an embodiment, the cell is non-neuronal in origin. In a further embodiment, the cell is a Cos-7 cell, a 293 human embryonic kidney cell, an L-M(TK-) cell or an NIH-3T3 cell.

This invention provides a pharmaceutical composition comprising a drug identified by the above-described method and a pharmaceutically acceptable carrier.

This invention provides a method of detecting expression of Y5 receptor by detecting the presence of mRNA coding for the Y5 receptor which comprises obtaining total mRNA from the cell and contacting the mRNA so obtained with the above-described nucleic acid probe under hybridizing conditions, detecting the presence of mRNA hybridized to the probe, and thereby detecting the expression of the Y5 receptor by the cell.

This invention provides a method of treating an abnormality in a subject, wherein the abnormality is alleviated by the inhibition of a Y5 receptor which comprises administering to a subject an effective amount of the above-described pharmaceutical composition effective to inhibit the Y5 receptor by the subject.

This invention provides a method of treating an abnormality in a subject wherein the abnormality is alleviated by the activation of a Y5 receptor which comprises administering to a subject an effective amount of the above-described pharmaceutical composition effective to activate the Y5 receptor in the subject.

This invention provides a method of treating an abnormality in a subject, wherein the abnormality is alleviated by the inhibition of a Y5 receptor which comprises administering to a subject an effective amount of Y5 receptor antagonist.

This invention provides a method of treating an abnormality in a subject wherein the abnormality is alleviated by the activation of a Y5 receptor which comprises administering to a subject an effective amount of a Y5 receptor agonist. In an embodiment, the abnormal condition is obesity. In a further embodiment, the abnormal condition is anorexia. In still another embodiment, the abnormal condition is bulimia nervosa. In a separate embodiment, the abnormal condition is a sexual/reproductive disorder. In another embodiment, the abnormal condition is depression. In another embodiment, the abnormal condition is anxiety.

In an embodiment, the abnormal condition is gastric ulcer. In a further embodiment, the abnormal condition is memory loss. In a further embodiment, the abnormal condition is migraine. In a further embodiment, the abnormal condition is pain. In a further embodiment, the abnormal condition is epileptic seizure. In a further embodiment, the abnormal condition is hypertension. In a further embodiment, the abnormal condition is cerebral hemorrhage. In a further embodiment, the abnormal condition is shock. In a further embodiment, the abnormal condition is congestive heart failure. In a further embodiment, the abnormal condition is sleep disturbance. In a further embodiment, the abnormal condition is nasal congestion. In a further embodiment, the abnormal condition is diarrhea.

This invention provides a method of treating obesity in a subject which comprises administering to the subject an effective amount of a Y5 receptor antagonist.

This invention provides a method of treating anorexia in a subject which comprises administering to the subject an effective amount of a Y5 receptor agonist.

This invention provides a method of treating bulimia nervosa in a subject which comprises administering to the subject an effective amount of a Y5 receptor antagonist.

This invention provides a method of inducing a subject to eat which comprises administering to the subject an effective amount of a Y5 receptor agonist. In one embodiment, the subject is a vertebrate. In another embodiment, the subject is a human.

This invention provides a method of increasing the consumption of a food product by a subject which comprises a composition of the food product and an effective amount of a Y5 receptor agonist. In one embodiment, the subject is a vertebrate. In another embodiment, the subject is a human.

This invention provides a method of treating abnormalities which are alleviated by reduction of activity of a human Y5 receptor which comprises administering to a subject an amount of the abovedescribed pharmaceutical composition effective to reduce the activity of human Y5 receptor and thereby alleviate abnormalities resulting from overactivity of a human Y5 receptor.

This invention provides a method of treating an abnormal condition related to an excess of Y5 receptor activity which comprises administering to a subject an amount of the pharmaceutical composition effective to block binding of a ligand to the Y5 receptor and thereby alleviate the abnormal condition.

This invention provides a method of detecting the presence of a human Y5 receptor on the surface of a cell which comprises contacting the cell with the antibody capable of binding to the human Y5 receptor under conditions permitting binding of the antibody to the receptor, detecting the presence of the antibody bound to the cell, and thereby detecting the presence of a human Y5 receptor on the surface of the cell.

This invention provides a method of determining the physiological effects of varying levels of activity of a human Y5 receptors which comprises producing a transgenic non-human mammal whose levels of human Y5 receptor activity are varied by use of an inducible promoter which regulates human Y5 receptor expression.

This invention provides a method of determining the physiological effects of varying levels of activity of a human Y5 receptors which comprises producing a panel of transgenic nonhuman mammals each expressing a different amount of human Y5 receptor.

This invention provides a method for identifying a substance capable of alleviating the abnormalities resulting from overactivity of a human Y5 receptor comprising administering a substance to the above-described transgenic nonhuman mammals, and determining whether the substance alleviates the physical and behavioral abnormalities displayed by the transgenic nonhuman mammal as a result of overactivity of a human Y5 receptor.

This invention provides a method for treating the abnormalities resulting from overactivity of a human Y5 receptor which comprises administering to a subject an amount of the above-described pharmaceutical composition effective to alleviate the abnormalities resulting from overactivity of a human Y5 receptor.

This invention provides a method for identifying a substance capable of alleviating the abnormalities resulting from underactivity of a human Y5 receptor comprising administering the substance to the above-described transgenic nonhuman mammals and determining whether the substance alleviates the physical and behavioral abnormalities displayed by the transgenic nonhuman mammal as a result of underactivity of a human Y5 receptor.

This invention provides a method for treating the abnormalities resulting from underactivity of a human Y5 receptor which comprises administering to a subject an amount of the above-described pharmaceutical composition effective to alleviate the abnormalities resulting from underactvity of a human Y5 receptor.

This invention provides a method for diagnosing a predisposition to a disorder associated with the activity of a specific human Y5 receptor allele which comprises: a. obtaining DNA of subjects suffering from the disorder; performing a restriction digest of the DNA with a panel of restriction enzymes; c. electrophoretic-ally separating the resulting DNA fragments on a sizing gel; d. contacting the resulting gel with a nucleic acid probe capable of specifically hybridizing to DNA encoding a human Y5 receptor and labelled with a detectable marker; e. detecting labelled bands which have hybridized to the DNA encoding a human Y5 receptor labelled with a detectable marker to create a unique band pattern specific to the DNA of subjects suffering from the disorder; f. preparing DNA obtained for diagnosis by steps a–e; and g. comparing the unique band pattern specific to the DNA of subjects suffering from the disorder from step e and the DNA obtained for diagnosis from step f to determine whether the patterns are the same or different and to diagnose thereby predisposition to the disorder if the patterns are the same. In an embodiment, a disorder associated with the activity of a specific human Y5 receptor allele is diagnosed.

This invention provides a method of preparing an isolated Y5 receptor which comprises: a. inducing cells to express the Y5 receptor; b. recovering the receptor from the resulting cells; and c. purifying the receptor so recovered.

This invention provides a method of preparing the isolated Y5 receptor which comprises: a. inserting nucleic acid encoding Y5 receptor in a suitable vector; b. inserting the resulting vector in a suitable host cell; c. recovering the receptor produced by the resulting cell; and d. purifying the receptor so recovered.

This invention will be better understood from the Experimental Details which follow. However, one skilled in the art will readily appreciate that the specific methods and results discussed are merely illustrative of the invention as described more fully in the claims which follow thereafter.

Experimental Details

MATERIALS AND METHODS

CDNA Cloning

Total RNA was prepared by a modification of the guanidine thiocyanate method (Kingston, 1987), from 5 grams of rat hypothalamus (Rockland, Gilbertsville, Pa.). Poly A$^+$RNA was purified with a FastTrack kit (Invitrogen Corp., San Diego, Calif.). Double stranded (ds) cDNA was synthesized from 7 µg of poly A$^+$ RNA according to Gubler and Hoffman (Gubler and Hoffman, 1983), except that ligase was omitted in the second strand cDNA synthesis. The resulting DS cDNA was ligated to BstxI/EcoRI adaptors (Invitrogen Corp.), the excess of adaptors was removed by chromatography on Sephacryl 500 HR (Pharmacia®-LKB) and the ds-cDNA size selected on a Gen-Pak Fax HPLC column (Millipore Corp., Milford, Mass.). High molecular weight fractions were ligated in pEXJ.BS (A cDNA cloning expression vector derived from pcEXV-3; Okayama and Berg, 1983; Miller and Germain, 1986) cut by BstxI as described by Aruffo and Seed (Aruffo and Seed, 1987). The ligated DNA was electroporated in E.Coli MC 1061 F$^+$ (Gene Pulser, Biorad). A total of 3.4×10$^6$ independent clones with an insert mean size of 2.7 kb could be generated. The library was plated on Petri dishes (Ampicillin selection) in pools of 6.9 to 8.2×10$^3$ independent clones. After 18 hours amplification, the bacteria from each pool were scraped, resuspended in 4 ml of LB media and 1.5 ml processed for plasmid purification with a QIAprep-8 plasmid kit (Qiagen Inc, Chatsworth, Calif.). 1 ml aliquots of each bacterial pool were stored at −85° C. in 20% glycerol.

Isolation of a cDNA clone encoding an atypical rat hypothalamic NPY5 receptor

DNA from pools of ≈7500 independent clones was transfected into COS-7 cells by a modification of the DEAE-dextran procedure (Warden and Thorne, 1968). COS-7 cells were grown in Dulbecco's modified Eagle medium (DMEM) supplemented with 10% fetal calf serum, 100 U/ml of penicillin, 100 μg/ml of streptomycin, 2 mML-glutamine (DMEM-C) at 37° C. in 5% $CO_2$. The cells were seeded one day before transfection at a density of 30,000 cells/cm$^2$ on Lab-Tek chamber slides (1 chamber, Permanox slide from Nunc Inc., Naperville, Ill.). On the next day, cells were washed twice with PBS, 735 μl of transfection cocktail was added containing 1/10 of the DNA from each pool and DEAE-dextran (500 μg/ml) in Opti-MEM I serum free media (Gibco®BRL LifeTechnologies Inc. Grand Island, N.Y.). After a 30 min. incubation at 37° C., 3 ml of chloroquine (80 μM in DMEM-C) was added and the cells incubated a further 2.5 hours at 37° C. The media was aspirated from each chamber and 2 ml of 10% DMSO in DMEM-C added. After 2.5 min. incubation at room temperature, the media was aspirated, each chamber washed once with 2 ml PBS, the cells incubated 48 hours in DMEM-C and the binding assay was performed on the slides. After one wash with PBS, positive pools were identified by incubating the cells with 1 nM (3×10$^6$ cpm per slide) of porcine [$^{125}$I]-PYY (NEN; SA=2200Ci/mmole) in 20 mM Hepes-NaOH pH 7.4, CaCl2 1.26 mM, MgSO4 0.81 mM, $KH_2PO_4$ 0.44 mM, KCL 5.4, NaCl 10 mM, 0.1% BSA, 0.1% bacitracin for 1 hour at room temperature. After six washes (three seconds each) in binding buffer without ligand, the monolayers were fixed in 2.5% glutaraldehyde in PBS for five minutes, washed twice for two minutes in PBS, dehydrated in ethanol baths for two minutes each (70, 80, 95, 100%) and air dried. The slides were then dipped in 100% photoemulsion (Kodak® type NTB2) at 42° C. and exposed in the dark for 48 hours at 4° C. in light proof boxes containing drierite. Slides were developed for three minutes in Kodak® D19 developer (32 g/1 of water), rinsed in water, fixed in Kodak® fixer for 5 minutes, rinsed in water, air dried and mounted with Aqua-Mount (Lerner Laboratories, Pittsburgh, Pa.). Slides were screened at 25x total magnification. A single clone, CG-18, was isolated by SIB selection as described (Mc Cormick, 1987). DS-DNA was sequenced with a Sequenase kit (US Biochemical, Cleveland, Ohio) according to the manufacturer. Nucleotide and peptide sequence analysis were performed with GCG programs (Genetics Computer group, Madison, Wis.).

Isolation of the human Y5 homolog

Using rat oligonucleotide primers in TM 3 (sense primer; position 484–509 in FIG. 1A) and in TM 6 (antisense primer; position 1219–1243 in FIG. 3A), applicants screened a human hippocampal cDNA library using the polymerase chain reaction. 1 μl (4×10$^6$ bacteria) of each of 450 amplified pools containing each ≈5000 independent clones and representing a total of 2.2×10$^6$ was subjected directly to 40 cycles of PCR and the resulting products analyzed by agarose gel electrophoresis. One of three positive pools was analyzed further and by sib selection a single cDNA clone was isolated and characterized. This cDNA turned out to be full length and in the correct orientation for expression. DS-DNA was sequenced with a sequenase kit (US Biochemical, Cleveland, Ohio) according to the manufacturer.

Cell Culture

COS-7 cells were grown on 150 mm plates in D-MEM with supplements (Dulbecco's Modified Eagle Medium with 10% bovine calf serum, 4 mM glutamine, 100 units/ml penicillin/100 μg/ml streptomycin) at 37° C., 5% $CO_2$. Stock plates of COS-7 cells were trypsinized and split 1:6 every 3–4 days. Human embryonic kidney 293 cells were grown on 150mm plates in D-MEM with supplements (minimal essential medium) with Hanks' salts and supplements (Dulbecco's Modified Eagle Medium with 10% bovine calf serum, 4 mM glutamine, 100 units/ml penicillin/100 μg/ml streptomycin) at 37° C., 5% $CO_2$. Stock plates of 293 cells were trypsinized and split 1:6 every 3–4 days. Mouse fibroblast LMT(k)-cells were grown on 150 mm plates in D-MEM with supplements (Dulbecco's Modified Eagle Medium with 10% bovine calf serum, 4 mM glutamine, 100 units/ml penicillin/100 μg/ml streptomycin) at 37° C., 5% $CO_2$. Stock plates of COS-7 cells were trypsinized and split 1:10 every 3–4 days.

Transient Transfection

All receptor subtypes studied (human and rat Y1, human and rat Y2, human and rat Y4, human and rat Y5) were transiently transfected into COS-7 cells by the DEAE-dextran method, using 1 μg of DNA/10$^6$ cells (Cullen, 1987).

Stable Transfection

Human Y1, human Y2, and rat Y5 receptors were co-transfected with a G-418 resistant gene into the human embryonic kidney 293 cell line by a calcium phosphate transfection method (Cullen, 1987). Stably transfected cells were selected with G-418. Human Y4 receptors were similarly transfected into mouse fibroblast LMT(k)-cells.

Membrane Harvest

Membranes were harvested from COS-7 cells 48 hours after transient transfection. Adherent cells were washed twice in ice-cold phosphate buffered saline (138 mM NaCl, 8.1 mM $Na_2HPO_4$, 2.5 mM KCl, 1.2 mM $KH_2PO_4$, 0.9 mM $CaCl_2$, 0.5 mM $MgCl_2$, pH 7.4) and lysed by sonication in ice-cold sonication buffer (20 mM Tris-HCl, 5 mM EDTA, pH 7.7). Large particles and debris were cleared by low speed centrifugation (200×g, 5 min, 4° C.). Membranes were collected from the supernatant fraction by centrifugation (32,000×g, 18 min, 4° C.), washed with ice-cold hypotonic buffer, and collected again by centrifugation (32,000×g, 18 min, 4° C.). The final membrane pellet was resuspended by sonication into a small volume of ice-cold binding buffer (~1 ml for every 5 plates: 10 mM NaCl, 20 mM HEPES, 0.22 mM $KH_2PO_4$, 1.26 mM $CaCl_2$, 0.81 mM $MgSO_4$, pH 7.4). Protein concentration was measured by the Bradford method (Bradford, 1976) using Bio-Rad Reagent, with bovine serum albumin as a standard. Membranes were held on ice for up to one hour and used fresh, or flash-frozen and stored in liquid nitrogen.

Membranes were prepared similarly from dissected rat hypothalamus. Frozen hypothalami were homogenized for 20 seconds in ice-cold sonication buffer with the narrow probe of a Virtishear homogenizer at 1000 rpm (Virtis, Gardiner, N.Y.). Large particles and debris were cleared by centrifugation (200×g, 5 min, 4° C.) and the supernatant fraction was reserved on ice. Membranes were further extracted from the pellet by repeating the homogenization and centrifugation procedure two more times. The supernatant fractions were pooled and subjected to high speed centrifugation (100,000×g, 20 min. 4° C.). The final membrane pellet was resuspended by gentle homogenization into a small volume of ice-cold binding buffer (1 ml/gram wet weight tissue) and held on ice for up to one hour, or flash-frozen and stored in liquid nitrogen.

Radioligand Binding to Membrane suspensions

Membrane suspensions were diluted in binding buffer supplemented with 0.1% bovine serum albumin to yield an optimal membrane protein concentration so that $^{125}$-PYY bound by membranes in the assay was less than 10% of $^{125}$-IPYY delivered to the sample (100,000 dpm/sample= 0.08 nM for competition binding assays). $^{125}$I-PYY and peptide competitors were also diluted to desired concentrations in supplemented binding buffer. Individual samples were then prepared in 96-well polypropylene microtiter plates by mixing $^{125}$I-PYY (25 µl), competing peptides or supplemented binding buffer (25 µl), and finally, membrane suspensions (200 µl). Samples were incubated in a 30° C. water bath with constant shaking for 120 min. Incubations were terminated by filtration over Whatman GF/C filters (pre-coated with 1% polyethyleneimine and air-dried before use), followed by washing with 5 ml of ice-cold binding buffer. Filter-trapped membranes were impregnated with MultiLex solid scintillant (Wallac, Turku, Finland) and counted for $^{125}$I in a Wallac Beta-Plate Reader. Non-specific binding was defined by 300 nM human NPY for all receptors except the Y4 subtypes; 100 nM human PP was used for the human Y4 and 100 nM rat PP for the rat Y4. Specific binding in time course and competition studies was typically 80%; most non-specific binding was associated with the filter. Binding data were analyzed using nonlinear regression and statistical techniques available in the GraphPAD Prism package (San Diego, Calif.).

Functional Assay: Radioimmunoassay of cAMP

Stably transfected cells were seeded into 96-well microtiter plates and cultured until confluent. To reduce the potential for receptor desensitization, the serum component of the media was reduced to 1.5% for 4 to 16 hours before the assay. Cells were washed in Hank's buffered saline, or HBS (150 mM NaCl, 20 mM HEPES, 1 mM $CaCl_2$, 5 mM KCl, 1 mM $MgCl_2$, and 10 mM glucose) supplemented with 0.1% bovine serum albumin plus 5 mM theophylline and pre-equilibrated in the same solution for 20 min at 37° C. in 5% $CO_2$. Cells were then incubated 5 min with 10 µM forskolin and various concentrations of receptor-selective ligands. The assay was terminated by the removal of HBS and acidification of the cells with 100 mM HCl. Intracellular cAMP was extracted and quantified with a modified version of a magnetic bead-based radioimmunoassay (Advanced Magnetics, Cambridge, Mass.). The final antigen/antibody complex was separated from free $^{125}$I-cAMP by vacuum filtration through a PVDF filter in a microtiter plate (Millipore, Bedford, Mass.). Filters were punched and counted for $^{125}$I in a Packard gamma counter. Binding data were analyzed using nonlinear regression and statistical techniques available in the GraphPAD Prism package (San Diego, Calif.).

Tissue preparation for neuroanatomical studies

Male Sprague-Dawley rats (Charles Rivers) were decapitated and the brains rapidly removed and frozen in isopentane. Coronal sections were cut at 11 µm on a cryostat and thaw-mounted onto poly-L-lysine coated slides and stored at −80° C. until use. Prior to hybridization, tissues were fixed in 4% paraformaldehyde, treated with 5 mM dithiothreitol, acetylated in 0.1M triethanolamine containing 0.25% acetic anhydride, delipidated with chloroform, and dehydrated in graded ethanols.

Probes

The oligonucleotide probes employed to characterize the distribution of the rat NPY Y5 mRNA were complementary to nucleotides 1121 to 1165 in the 5,6-loop of the rat Y5 mRNA (FIG. 3A) 45 mer antisense and sense oligonucleotide probes were synthesized on a Millipore Expedite 8909 Nucleic Acid Synthesis System. The probes were then lyophilized, reconstituted in sterile water, and purified on a 12% polyacrylamide denaturing gel. The purified probes were again reconstituted to a concentration of 100 ng/µl, and stored at −20° C.

In Situ Hybridization

Probes were 3'-end labeled with $^{35}$S-dATP (1200 Ci/mmol, New England Nuclear, Boston, Mass.) to a specific activity of $10^9$ dpm/µg using terminal deoxynucleotidyl transferase (Pharmacia®). The radiolabeled probes were purified on Biospin 6 chromatography columns (Bio-Rad; Richmond, Calif.), and diluted in hybridization buffer to a concentration of $1.5 \times 10^4$ cpm/µl. The hybridization buffer consisted of 50% formamide, 4× sodium citrate buffer (1× SSC=0.15M NaCl and 0.015M sodium citrate), 1× Denhardt's solution (0.2% polyvinylpyrrolidine, 0.2% Ficoll, 0.2% bovine serum albumin), 50 mM dithiothreitol, 0.5 mg/ml salmon sperm DNA, 0.5 mg/ml yeast tRNA, and 10% dextran sulfate. One hundred µl of the diluted radiolabeled probe was applied to each section, which was then covered with a Parafilm coverslip. Hybridization was carried out overnight in humid chambers at 40° to 55° C. The following day the sections were washed in two changes of 2× SSC for one hour at room temperature, in 2× SSC for 30 min at 50°–60° C. and finally in 0 1× SSC for 30 min at room temperature. Tissues were dehydrated in graded ethanols and apposed to Kodak®XAR-5 film for 3 days to 3 weeks at −20° C., then dipped in Kodak NTB3 autoradiography emulsion diluted 1:1 with 0.2% glycerol water. After exposure at 4° C. for 2 to 8 weeks, the slides were developed in Kodak® D-19 developer, fixed, and counterstained with cresyl violet.

Hybridization Controls

Controls for probe/hybridization specificity included hybridization with the radiolabeled sense probe, and the use of transfected cell lines. Briefly, COS-7 cells were transfected (see above) with receptor cDNAs for the rat Y1, Y2 (disclosed in US patent application Ser. No. 08/192,288, filed on Feb. 3, 1994 U.S. Pat. No. 5,545,549), Y4 (disclosed in US patent application Ser. No. 08/176,412, filed on Dec. 28, 1993 U.S. Pat. No. 5,516,653), or Y5. As described above, the transfected cells were treated and hybridized with the radiolabeled Y5 antisense and sense oligonucleotide probes, washed, and apposed to film for 1–7 days.

Analysis of hybridization signals

Sections through the rat brain were analyzed for hybridization signals in the following manner. "Hybridization signal" as used in the present context indicates the relative number of silver grains observed over neurons in a selected area of the rat brain. Two independent observers rated the intensity of the hybridization signal in a given brain area as nonexistent, low, moderate, or high. These were then converted to a subjective numerical scale as 0, +1, +2, or +3 (see Table 10), and mapped on to schematic diagrams of coronal sections through the rat brain (see FIG. 11).

Materials

Cell culture media and supplements were from Specialty Media (Lavallette, N.J.). Cell culture plates (150 mm and 96-well microtiter) were from Corning (Corning, N.Y.). Polypropylene 96-well microtiter plates were from Co-star (Cambridge, Mass.). Porcine $^{125}$I-PYY and $^{125}$I-PYY$_{3-36}$ was from New England Nuclear (Boston, Mass.). Commercially available NPY and related peptide analogs were either from Bachem California (Torrance, Calif.) or Peninsula (Belmont, Calif.); [D-Trp$^{32}$]NPY and PP C-terminal fragments were synthesized by custom order from Chiron Mimotopes Peptide Systems (San Diego, Calif.). Bio-Rad Reagent was from Bio-Rad (Hercules, Calif.). Bovine serum albumin (ultra-fat free, A-7511) was from Sigma (St. Louis. Mo.). All other materials were reagent grade.

EXPERIMENTAL RESULTS
cDNA Cloning

Figure 2:
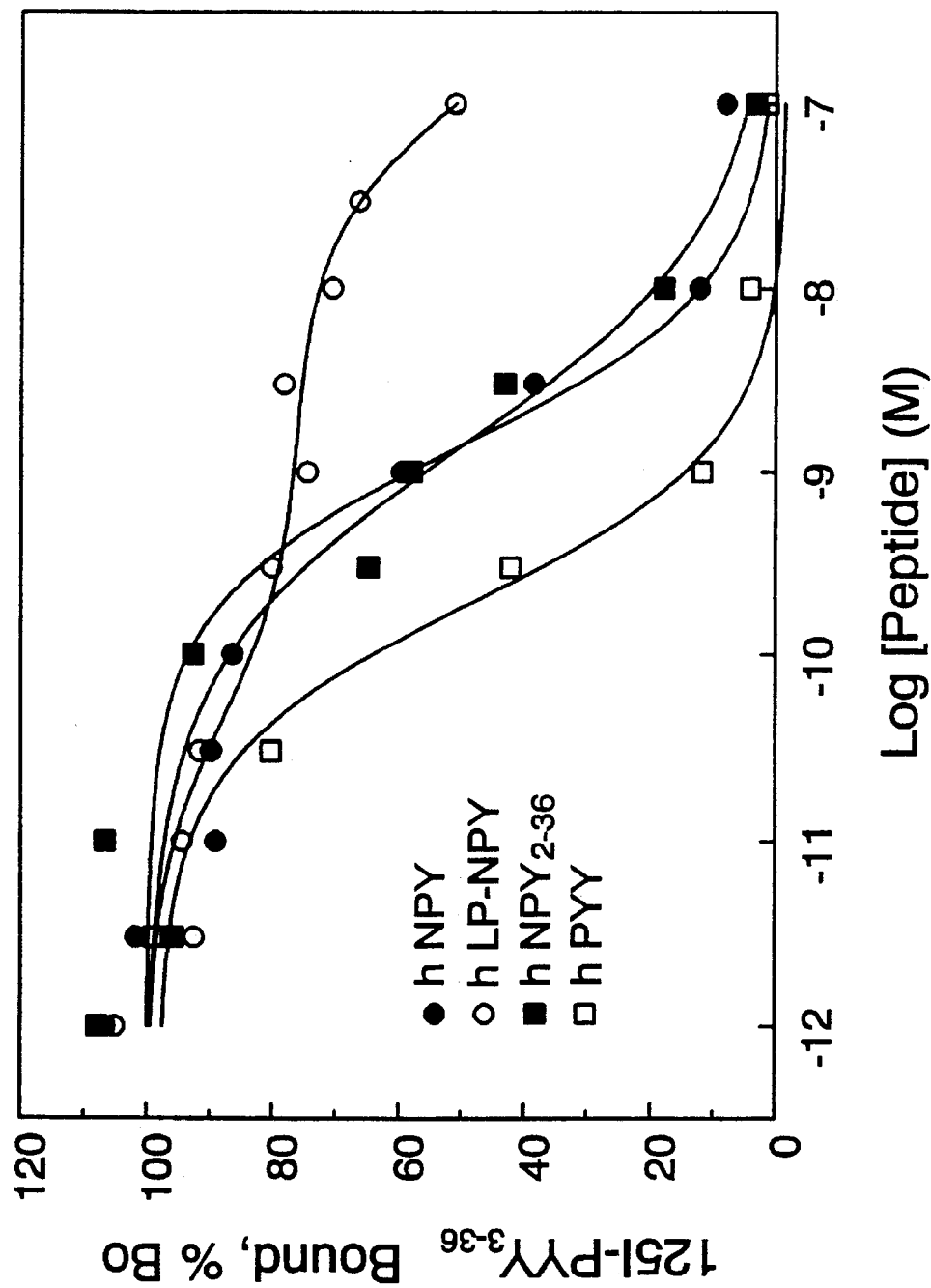

In order to clone a rat hypothalamic "atypical" NPY receptor subtype, applicants used an expression cloning strategy in COS-7 cells (Gearing et al, 1989; Kluxen et al, 1992; Kiefer et al, 1992). This strategy was chosen for its extreme sensitivity since it allows detection of a single "receptor positive" cell by direct microscopic autoradiography. Since the "atypical" receptor has only been described in feeding behavior studies involving injection of NPY and NPY related ligands in rat hypothalamus (see introduction), applicants first examined its binding profile by running competitive displacement studies of $^{125}$I-PYY and $^{125}$I-PYY$_{3-36}$ on membranes prepared from rat hypothalamus. The competitive displacement data indicate: 1) Human PP is able to displace 20% of the bound $^{125}$I-PYY with an IC$_{50}$ of 11 nM (FIG. 1 and Table 2). As can be seen in table 5, this value does not fit with the isolated rat Y1, Y2 and Y4 clones and could therefore correspond to another NPY/PYY receptor subtype. 2) [Leu$_{31}$, Pro$_{34}$] NPY (a Y1 specific ligand) is able to displace with high affinity (IC$_{50}$ of 0.38) 27% of the bound $^{125}$I-PYY$_{3-36}$ ligand (a Y2 specific ligand) (FIG. 2 and table 2). These data provide the first evidence based on a binding assay that rat hypothalamic membranes could carry an NPY receptor subtype with a mixed Y1/Y2 pharmacology (referred to as the "atypical" subtype) which fits with the pharmacology defined in feeding behavior studies.

TABLE 2: Pharmacological profile of the rat hypothalamus.

Binding data reflect competitive displacement of $^{125}$I-PYY and $^{125}$I-PYY$_{3-36}$ from rat hypothalamic membranes. Peptides were tested at concentrations ranging from 0.001 nM to 100 nM unless noted. The IC$_{50}$ value corresponding to 50% displacment, and the percentage of displacement relative to that produced by 300 nM human NPY, were determined by nonlinear regression analysis. Data shown are representative of at least two independent experiments.

TABLE 2

| Peptide | IC$_{50}$ Values, nM (% NPY-produced displacement) | | |
|---|---|---|---|
| | $^{125}$I-PYY | $^{125}$I-PYY$_{3-36}$ | |
| human NPY | 0.82 (100%) | 1.5 (100%) | |
| human NPY$_{2-36}$ | 2.3 (100%) | 1.2 (100%) | |
| human [Leu$^{31}$, Pro$^{34}$]NPY | 0.21 (44%) 340 (56%) | 0.38 (27%) | 250 (73%) |
| human PYY | 1.3 (100%) | 0.29 (100%) | |
| human PP | 11 (20%) | untested | |

Based on the above data, a rat hypothalamic cDNA library of 3×10$^6$ independent recombinants with a 2.7 kb average insert size was fractionated into 450 pools of ≈7500 independent clones. All pools were tested in a binding assay with $^{125}$I-PYY as described (Y2 patent). Seven pools gave rise to positive cells in the screening assay (#'s 81, 92, 147, 246, 254, 290, 312). Since Y1, Y2, Y4 and Y5 receptor subtypes (by PCR or binding analysis) are expressed in rat hypothalamus, applicants analyzed the DNA of positive pools by PCR with rat Y1, Y2 and Y4 specific primers. Pools #147, 246, 254 and 312 turned out to contain cDNAs encoding a Y1 receptor, pool #290 turned out to encode a Y2 subtype, but pools #81 and 92 were negative by PCR analysis for Y1, Y2 and Y4 and therefore likely contained a cDNA encoding a new rat hypothalamic NPY receptor (Y5). Pools #81 and 92 later turned out to contain an identical NPY receptor cDNA. Pool 92 was subjected to sib selection as described (Y2 patent) until a single clone was isolated (designated CG-18).

The isolated clone carries a 2.8 kb cDNA. This cDNA contains an open reading frame between nucleotides 779 and 2146 that encodes a 456 amino acid protein. The long 5' untranslated region could be involved in the regulation of translation efficiency or mRNA stability. The flanking sequence around the putative initiation codon does not conform to the Kozak consensus sequence for optimal translation initiation (Kozak, 1989, 1991). The hydrophobicity plot displayed seven hydrophobic, putative membrane spanning regions which makes the rat hypothalamic Y5 receptor a member of the G-protein coupled superfamily. The nucleotide and deduced amino acid sequences are shown in FIGS. 3 and 4, respectively. Like most G-protein coupled receptors, the Y5 receptor contains consensus sequences for N-linked glycosylation, in the amino terminus (position 21 and 28) involved in the proper expression of membrane proteins (Kornfeld and Kornfeld, 1985). The Y5 receptor carries two highly conserved cysteine residues in the first two extracellular loops that are believed to form a disulfide bond stabilizing the functional protein structure (Probst et al, 1992). The Y5 receptor shows 9 potential phosphorylation sites for protein kinase C in positions 204, 217, 254, 273, 285, 301, 328, 336 and 409 and 2 cAMP- and cGMP-dependent protein kinase phosphorylation sites in positions 298 and 370. It should be noted that 8 of those 11 potential phosphorylation sites are located in the third intracellular loop, two in the second intra-cellular loop and one in the carboxy terminus of the receptor and therefore could play a role in regulating functional characteristics of the Y5 receptor (Probst et al, 1992). In addition the rat Y5 receptor carries a leucine zipper motif in its first putative transmembrane domain (Landschulz et al, 1988). A tyrosine kinase phosphorylation site is found in the middle of the leucine zipper.

Figures 8A, 8B, 8C:
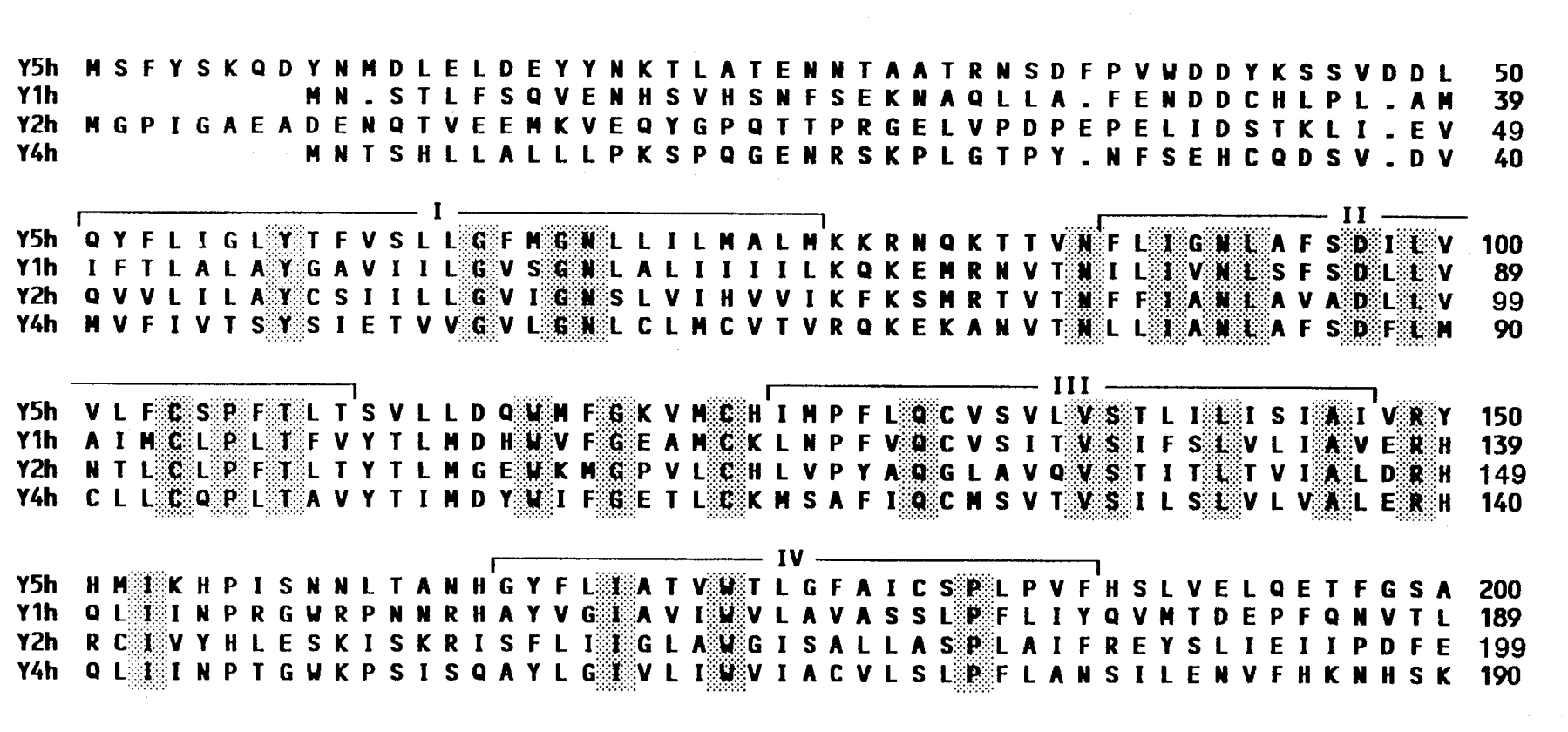

Localization studies (see below) show that the Y5mRNA is present in several areas of the rat hippocampus. Assuming a comparable localization in human brain, applicants screened a human hippocampal cDNA library (Y2 patent) with rat oligonucleotide primers which were shown to yield a DNA band of the expected size in a PCR reaction run on human hippocampal cDNA (C. Gerald, unpublished results). Using this PCR screening strategy (Gerald et al, 1994, submitted for publication), three positive pools were identified. One of these pools was analyzed further, and an isolated clone was purified by sib selection. The isolated clone (CG-19) turned out to contain a full length cDNA cloned in the correct orientation for functional expression (see below). The human Y5 nucleotide and deduced amino acid sequences are shown in FIGS. 5 and 6, respectively. When compared to the rat Y5 receptor the human sequence shows 84.1% nucleotide identity (FIG. 7A to 7E) and 87.2% amino acid identity (FIG. 7F and 7G). The rat protein sequence is one amino acid longer at the very end of both amino and carboxy tails of the receptor when compared to the human. The human 5–6 loop is one amino acid longer than the rat and shows multiple non conservative substitutions. Even though the 5–6 loops show significant changes between the rat and human homologs, all of the protein motifs found in the rat receptor are present in the human homolog. All putative transmembrane domains and extra cellular loop regions are highly conserved (FIG. 7F and 7G). Therefore, both pharmacological profiles and functional characteristics of the rat and human Y5 receptor subtype homologs may be expected to match closely. When the human and rat Y5 receptor sequences were compared to other NPY receptor subtypes or to other human G protein-coupled receptor subtypes, both overall and transmembrane domain identities are very low, showing that the Y5 receptor genes are not closely related to any other previously characterized cDNAs. Even among the human NPY receptor family, Y1, Y2, Y4 and Y5 members show unusually low levels of amino acid identity (FIG. 8A through 8C).

TABLE 3

Human Y5 transmembrane domains identity with other human NPY receptor subtypes and other human G-protein coupled receptors

| Receptor subtype | % TM identity |
| --- | --- |
| Y-4 | 40 |
| Y-2 | 42 |
| Y-1 | 42 |
| MUSGIR | 32 |
| DroNPY | 31 |
| Beta-1 | 30 |
| Endotheline-1 | 30 |
| Dopamine D2 | 29 |
| Adenosine A2b | 28 |
| Subst K | 28 |
| Alpha-2A | 27 |
| 5-HT1Dalpha | 26 |
| Alpha-1A | 26 |
| IL-8 | 26 |
| 5-HT2 | 25 |
| Subst P | 24 |

Figure 9:
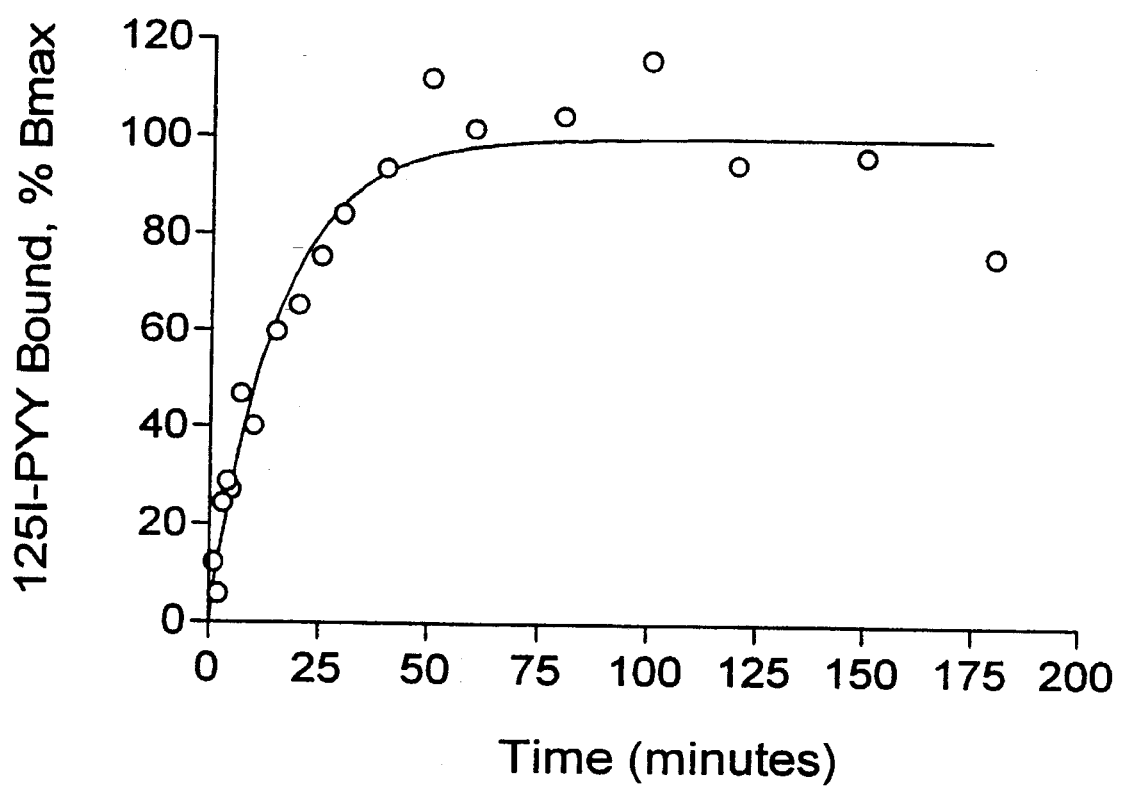
Figure 10:
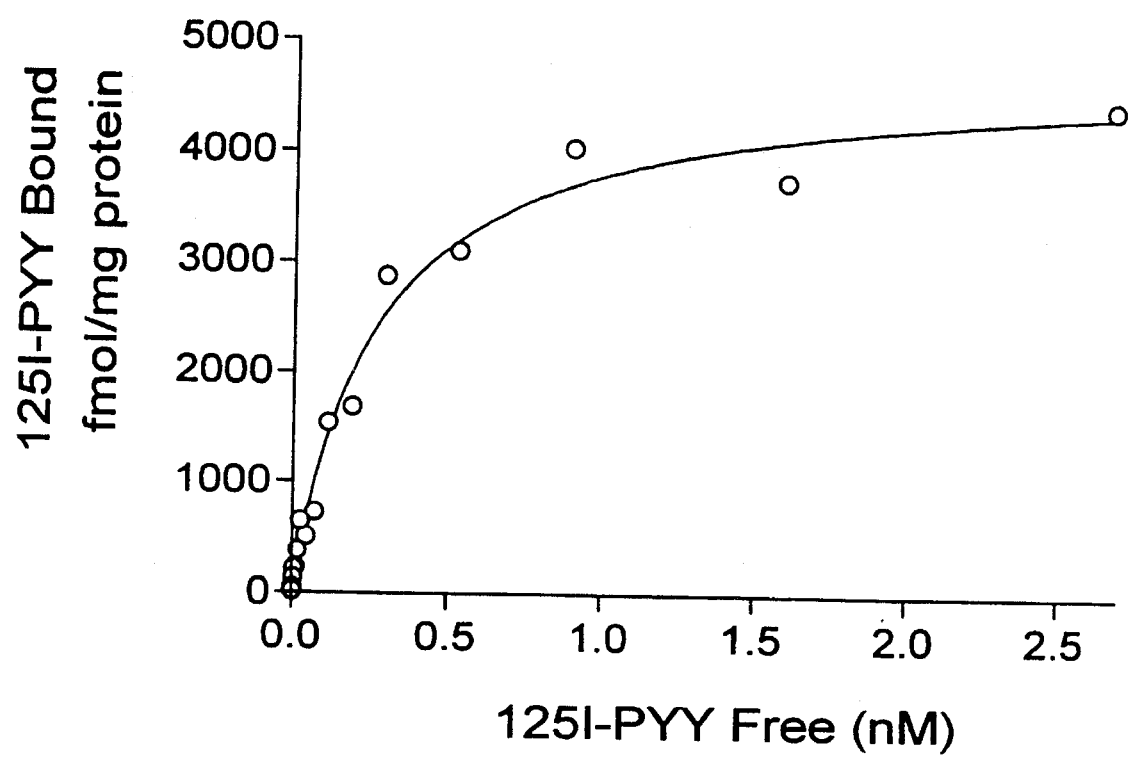

Binding Studies The cDNA for the rat hypothalamic Y5 receptor was expressed in COS-7 cells for full pharmacological evaluation. $^{125}$I-PYY bound specifically to membranes from COS-7 cells transiently transfected with the rat Y5 receptor construct. The time course of specific binding was measured in the presence of 0.08 nM $^{125}$I-PYY at 30° C. (FIG. 9). The association curve was monophasic, with an observed association rate ($K_{obs}$) of 0.06 min$^{-1}$ and a $t_{1/2}$ of 11 min; equilibrium binding was 99% complete within 71 min and stable for at least 180 min. All subsequent binding assays were carried out for 120 min at 30 ° C. The binding of $^{125}$I-PYY to transiently expressed rat Y5 receptors was saturable over a radioligand concentration range of 0.4 pM to 2.7 nM. Binding data were fit to a one-site binding model with an apparent $K_d$ of 0.29 nM (p$K_d$=9.54±0.13, n=4). A receptor density of between 5 and 10 pmol/mg membrane protein was measured on membranes which had been frozen and stored in liquid nitrogen (FIG. 10). Membranes from mock-transfected cells, when prepared and analyzed in the same way as those from CG-18-transfected cells, displayed no specific binding of $^{125}$I-PYY (data not shown). Applicants conclude that the $^{125}$I-PYY binding sites observed under the described conditions were derived from the rat Y5 receptor construct.

Figure 11:
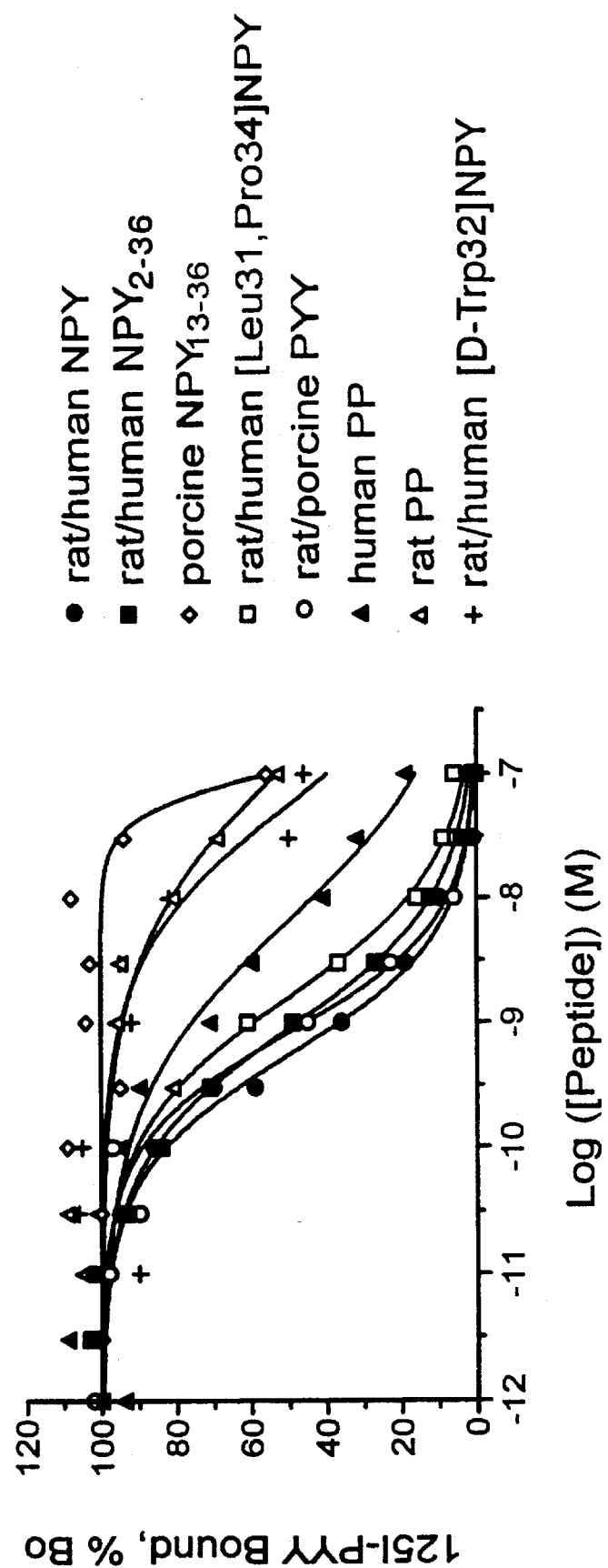

The pharmacological profile of the rat Y5 receptor was first studied by using pancreatic polypeptide analogs in membrane binding assays. The rank order of affinity for selected compounds was derived from competitive displacement of $^{125}$I-PYY (FIG. 11). The rat Y5 receptor was compared with cloned Y1, Y2, and Y4 receptors from human (Table 4) and rat (Table 5), all expressed transiently in COS-7 cells. One receptor subtype absent from our panel was the Y3, human or rat, as no model suitable for radioligand screening has yet been identified.

TABLE 4: Pharmacological profile of the rat Y5 receptor vs. Y-type receptors cloned from human.

Binding data reflect competitive displacement of $^{125}$I-PYY from membranes of COS-7 cells transiently expressing rat Y5 and human subtype clones. Peptides were tested at concentrations ranging from 0.001 nM to 1000 nM unless noted. IC$_{50}$ values corresponding to 50% displacement were determined by nonlinear regression analysis and converted to $K_i$ values according to the Chang-Prusoff equation. The data shown are representative of at least two independent experiments.

TABLE 4

| | K$_i$ Values (nM) | | | |
| --- | --- | --- | --- | --- |
| Peptide | Rat Y5 | Human Y4 | Human Y1 | Human Y2 |
| rat/human NPY | 0.68 | 2.2 | 0.07 | 0.74 |
| porcine NPY | 0.66 | 1.1 | 0.05 | 0.81 |
| human NPY$_{2-36}$ | 0.86 | 16 | 3.9 | 2.0 |
| porcine NPY$_{2-36}$ | 1.2 | 5.6 | 2.4 | 1.2 |
| porcine NPY$_{13-36}$ | 73 | 38 | 60 | 2.5 |
| porcine NPY$_{26-36}$ | >1000 | 304 | >1000 | 380 |
| porcine C2-NPY | 470 | 120 | 79 | 3.5 |
| human [Leu$^{31}$, Pro$^{34}$]NPY | 1.0 | 1.1 | 0.17 | >130 |
| human [D-Trp$^{32}$]NPY | 53 | >760 | >1000 | >1000 |
| human NPY free acid | 480 | >1000 | 490 | >1000 |
| rat/porcine PYY | 0.64 | 0.14 | 0.35 | 1.26 |
| human PYY | 0.87 | 0.87 | 0.18 | 0.36 |
| human PYY$_{3-36}$ | 8.4 | 15 | 41 | 0.70 |
| human PYY$_{13-36}$ | 190 | 46 | 33 | 1.5 |
| human [Pro$^{34}$]PYY | 0.52 | 0.12 | 0.14 | >310 |
| human PP | 5.0 | 0.06 | 77 | >1000 |
| human PP$_{2-36}$* | not tested | 0.06 | >40 | >100 |
| human PP$_{13-36}$* | not tested | 39 | >100 | >100 |
| rat PP | 180 | 0.16 | 450 | >1000 |
| salmon PP | 0.31 | 3.2 | 0.11 | 0.17 |

*Tested only up to 100 nM.

TABLE 5: Pharmacological profile of the rat Y5 receptor vs. Y-type receptors cloned from rat.

Binding data reflect competitive displacement of $^{125}$I-PYY from membranes of COS-7 cells transiently expressing rat Y5 and rat subtype clones. Peptides were tested at concentrations ranging from 0.001 nM to 1000 nM. IC$_{50}$ values corresponding to 50% displacement were determined by nonlinear regression analysis and converted to $K_i$ values according to the Chang-Prusoff equation. The data shown are representative of at least two independent experiments.

TABLE 5

| | K$_i$ Values (nM) | | | |
| --- | --- | --- | --- | --- |
| Peptide | Rat Y5 | Rat Y4 | Rat Y1 | Rat Y2 |
| rat/human NPY | 0.68 | 1.7 | 0.12 | 1.3 |
| human NPY$_{2-36}$ | 0.86 | 5.0 | 12 | 2.6 |
| porcine NPY$_{13-36}$ | 73 | 140 | 190 | 31 |
| human [Leu$^{31}$, Pro$^{34}$]NPY | 1.0 | 0.59 | 0.10 | >1000 |
| human [D-Trp$^{32}$]NPY | 53 | >630 | >1000 | 760 |
| rat/porcine PYY | 0.64 | 0.58 | 0.21 | 0.28 |
| human [Pro$^{34}$]PYY | 0.52 | 0.19 | 0.25 | >1000 |
| human PP | 5.0 | 0.04 | 43 | >1000 |
| rat PP | 230 | 0.19 | 350 | >1000 |
| salmon PP | 0.33 | 3.0 | 0.30 | 0.16 |

The rat Y5 receptor possessed a unique pharmacological profile when compared with human and rat Y-type receptors. It displayed a preference for structural analogs of rat/human NPY ($K_i$=0.68 nM) and rat/porcine PYY ($K_i$=0.64 nM) over most PP derivatives. The high affinity for salmon PP ($K_i=0.31$ nM) reflects the close similarity between salmon PP and rat NPY, sharing 81% of their amino acid sequence and maintaining identity at key positions: $Tyr^1$, $Gln^{34}$, and $Tyr^{36}$. Both N- and C-terminal peptide domains are apparently important for receptor recognition. The N-terminal tyrosine of NPY or PYY could be deleted without an appreciable loss in binding affinity ($K_i=0.86$ nM for rat/human $NPY_{2-36}$), but further N-terminal deletion was disruptive ($K_i=73$ nM for porcine $NPY_{13-36}$). This pattern places the binding profile of the Y5 receptor somewhere between that of the Y2 receptor (which receptor can withstand extreme N-terminal deletion) and that of the Y1 receptor (which receptor is sensitive to even a single-residue N-terminal deletion). Note that the human Y4 receptor can be described similarly ($K_i=0.06$ nM for human PP, 0.06 nM for human $PP_{2-36}$, and 39 nM for human $PP_{13-36}$). The Y5 receptor resembled both Y1 and Y4 receptors in its tolerance for ligands containing $Pro^{34}$ (as in human [$Leu^{31}$,$Pro^{34}$]NPY, human [$Pro^{34}$]-PYY, and human PP). Interestingly, the rat Y5 receptor displayed a preference for human PP ($K_i=5.0$ nM) over rat PP ($K_i=180$ nM). This pattern distinguishes the rat Y5 from the rat Y4 receptor, which binds both human and rat PP with $K_i$ values <0.2 nM. Hydrolysis of the carboxy terminal amide to free carboxylic acid, as in NPY free acid, was disruptive for binding affinity for the rat Y5 receptor ($K_i=480$ nM). The terminal amide appears to be a common structural requirement for pancreatic polypeptide family/receptor interactions.

Several peptides shown previously to stimulate feeding behavior in rats bound to the rat Y5 receptor with $K_i \leq 5.0$ nM. These include rat/human NPY ($K_i=0.68$ nM), rat/porcine PYY ($K_i=0.64$ nM), rat/human $NPY_{2-36}$ ($K_i=0.86$ nM), rat/human [$Leu^{31}$ $Pro^{31}$,]NPY ($K_i=1.0$ nM), and human PP ($K_i=5.0$ nM). Conversely, peptides which were relatively less effective as an orexigenic agents bound weakly to CG-18. These include porcine $NPY_{13-36}$ ($K_i=73$ nM), porcine C2-NPY ($K_i=470$ nM) and human NPY free acid ($K_i=480$ nM). The rank order of $K_i$ values are in agreement with rank orders of potency and activity for stimulation of feeding behavior when peptides are injected i.c.v. or directly into rat hypothalamus (Clark et al., 1984; Stanley et al., 1985; Kalra et al., 1991; Stanley et al., 1992). The rat Y5 receptor also displayed moderate binding affinity for [D-$Trp^{32}$]NPY ($K_i=53$ nM), the modified peptide reported to regulate NPY-induced feeding by Balasubramaniam and co-workers (1994). It is noteworthy that [D-$Trp^{32}$]NPY was ≥10-fold selective for CG-18 over the other cloned receptors studied, whether human or rat. These data clearly and definitively link the cloned Y5 receptor to the feeding response.

The cDNA corresponding to the human Y5 homolog isolated from human hippocampus was transiently expressed in COS-7 cells for membrane binding studies. The binding of $^{125}$I-PYY to the human Y5 receptor (CG-19) was saturable over a radioligand concentration range of 8 pM to 1.8 nM. Binding data were fit to a one-site binding model with an apparent $K_d$ of 0.10 nM. A maximum receptor density of 500 fmol/mg membrane protein was measured on fresh membranes. As determined by using peptide analogs within the pancreatic polypeptide family, the human Y5 pharmacological profile bears a striking resemblance to the rat Y5 receptor (Table 8).

TABLE 8: Pharmacological profile of the rat Y5 receptor vs. the human Y5 receptor.

Binding data reflect competitive displacement of $^{125}$-PYY from membranes of COS-7 cells transiently expressing the rat Y5 receptor and its human homolog. Peptides were tested at concentrations ranging from 0.001 nM to 1000 nM. $IC_{50}$ values corresponding to 50% displacement were determined by nonlinear regression analysis and converted to $K_i$ values according to the Chang-Prusoff equation.

TABLE 8

| Peptide | $K_i$ Values (nM) | |
|---|---|---|
| | Rat Y5 | Human Y5 |
| rat/human NPY | 0.68 | 0.15 |
| human $NPY_{2-36}$ | 0.86 | 0.33 |
| porcine $NPY_{13-36}$ | 73 | 110 |
| human [$Leu^{31}$, $Pro^{34}$]NPY | 1.0 | 0.72 |
| human [D-$Trp^{32}$]NPY | 53 | 18 |
| rat/porcine PYY | 0.64 | 0.75 |
| human [$Pro^{34}$]PYY | 0.52 | 0.34 |
| human PP | 5.0 | 1.7 |
| rat PP | 230 | 170 |
| salmon PP | 0.33 | 0.27 |

Functional Assay

Figure 12:
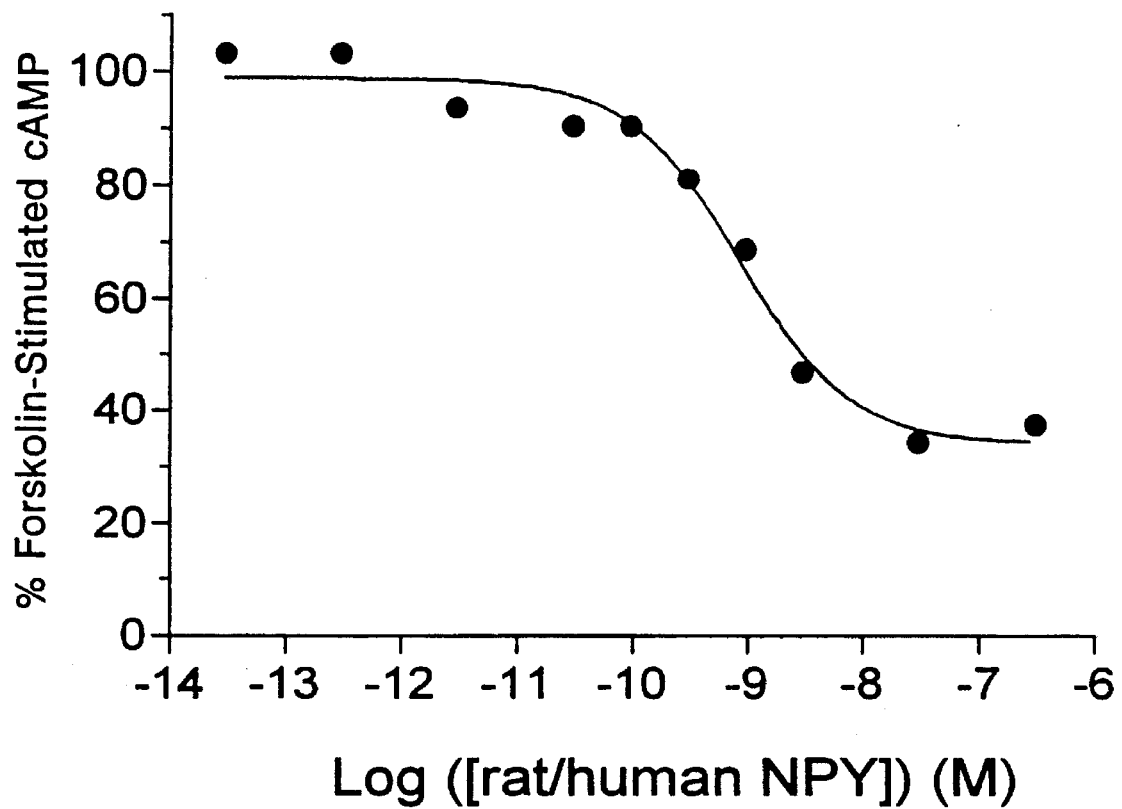
Figure 13A:
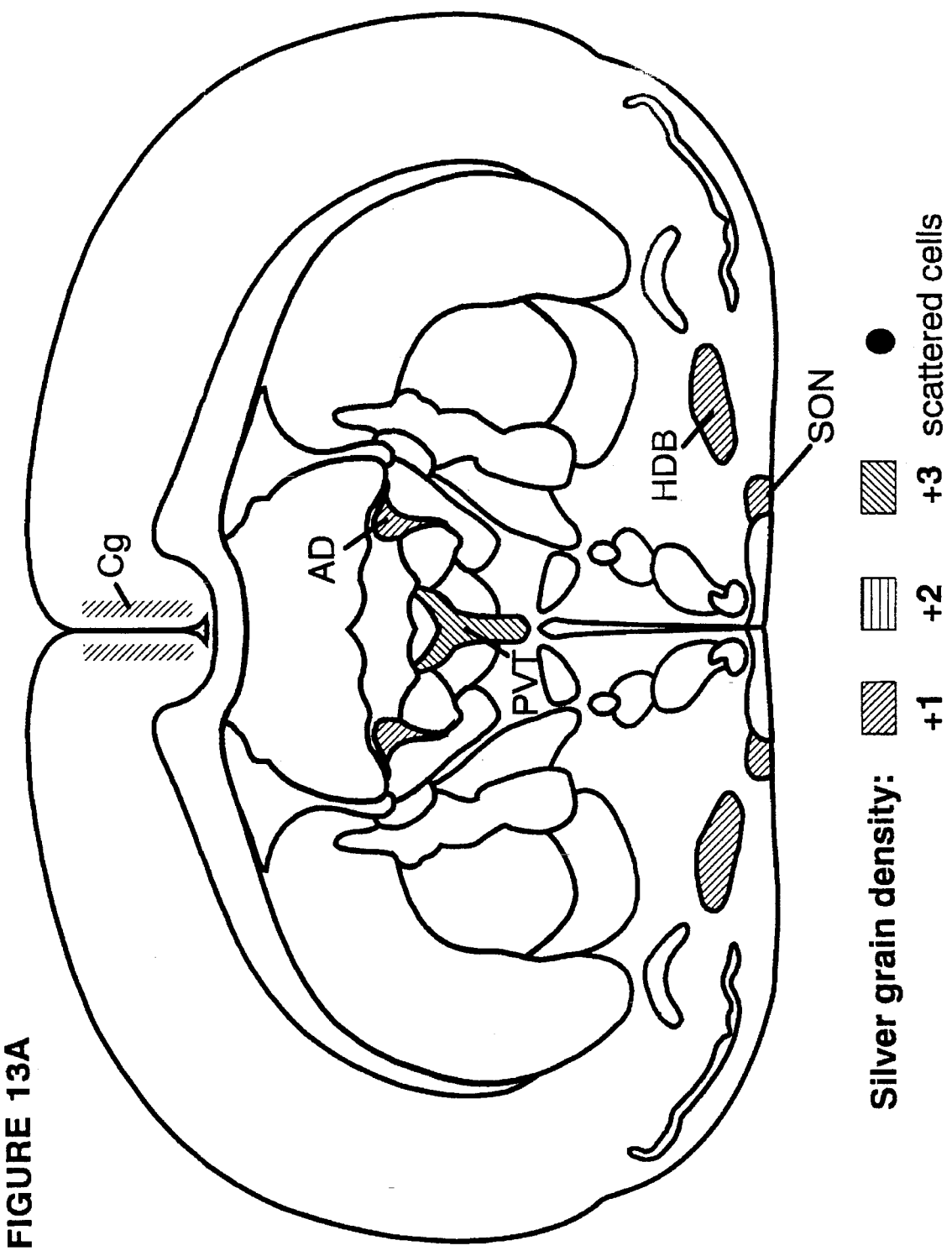
Figure 13B:
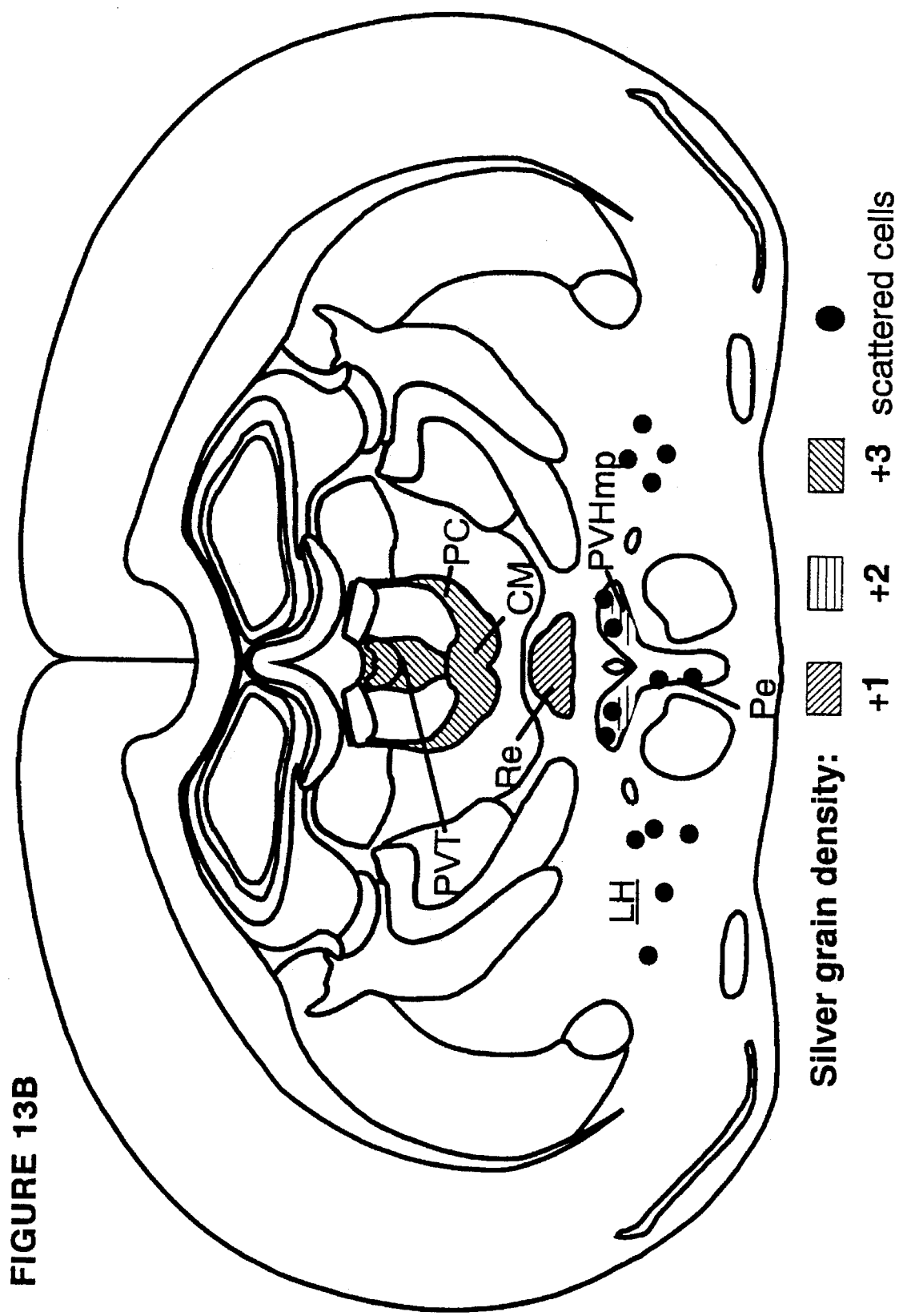
Figure 13C:
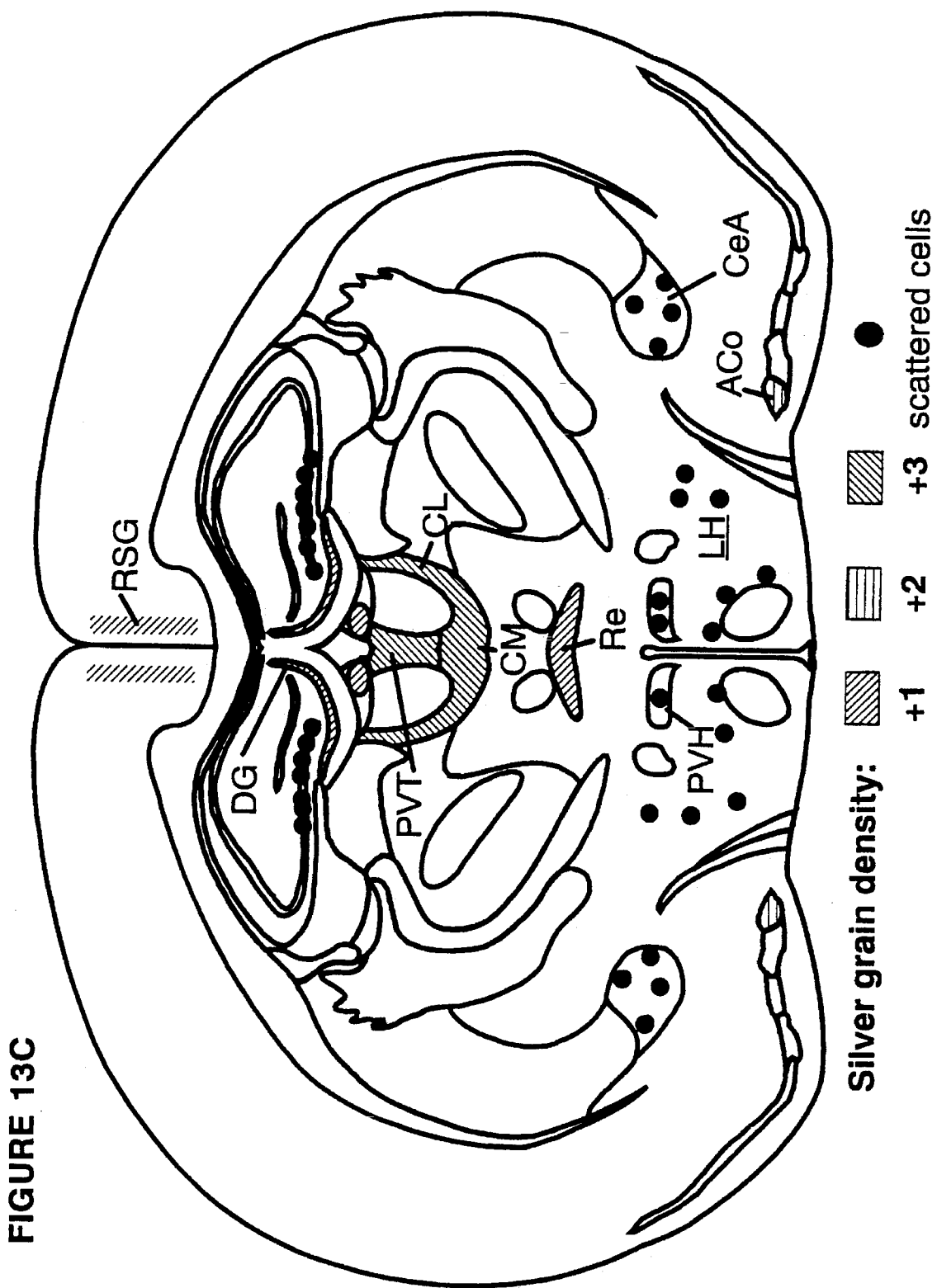
Figure 13D:
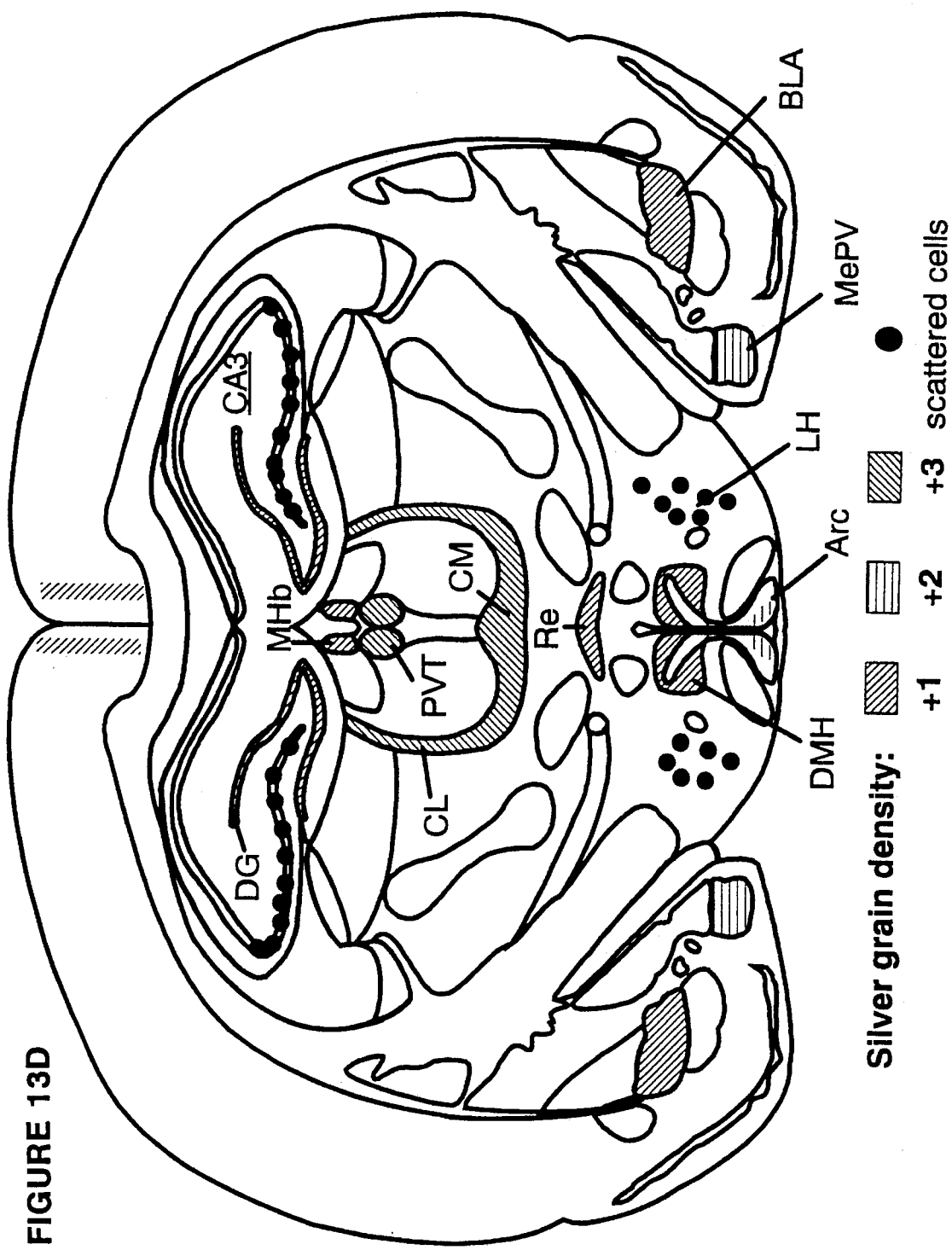
Figure 13E:
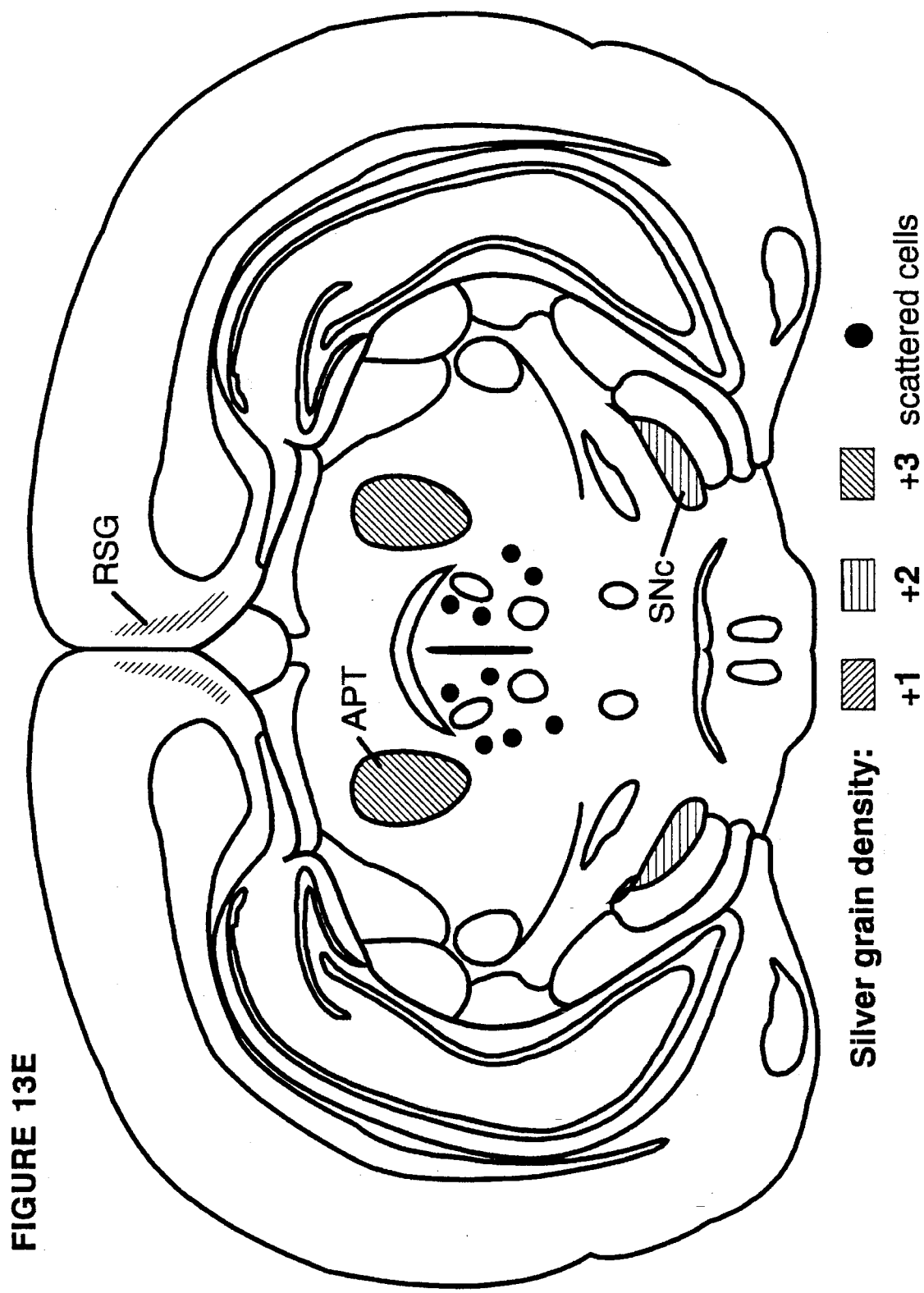
Figure 13F:
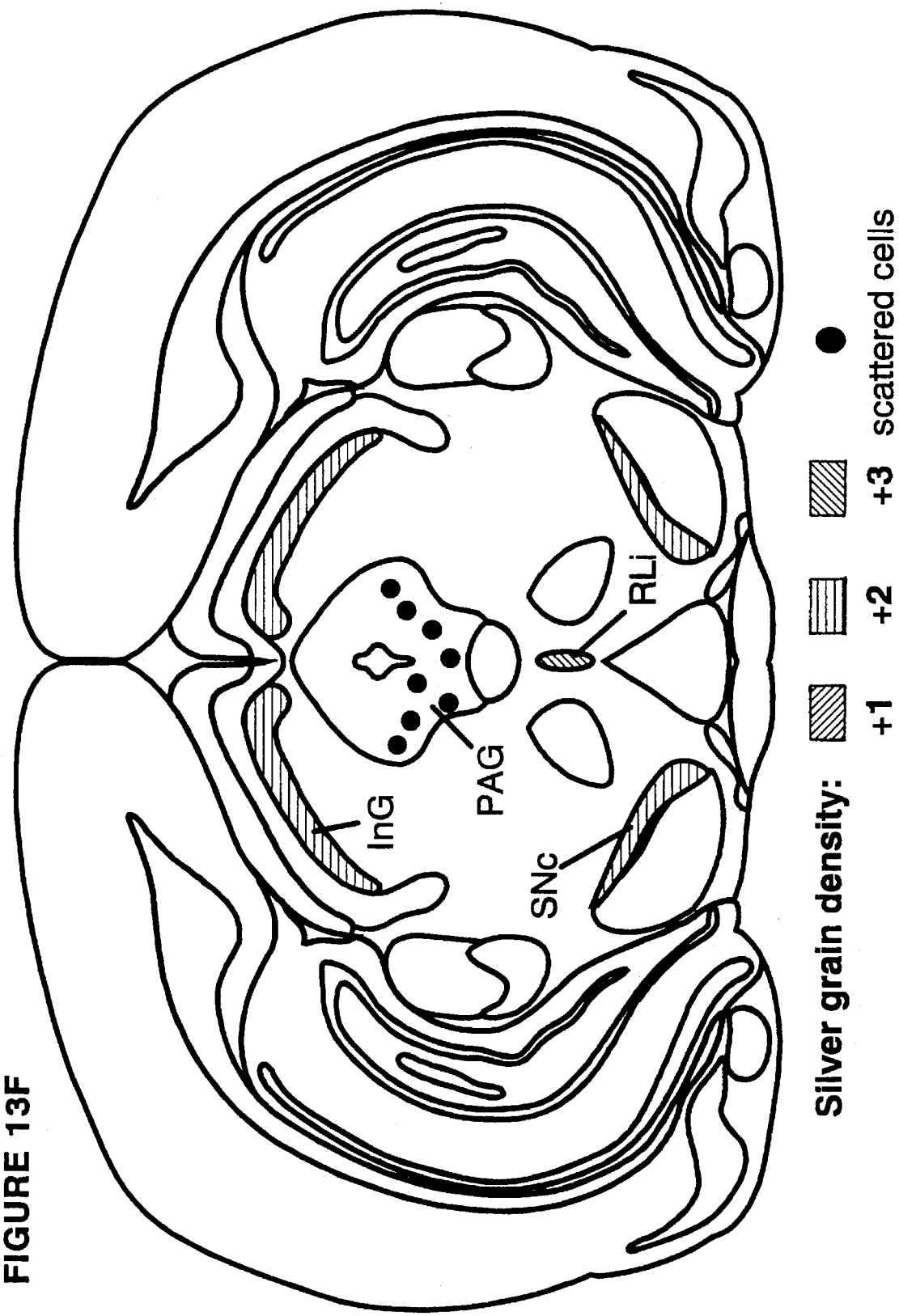
Figure 13G:
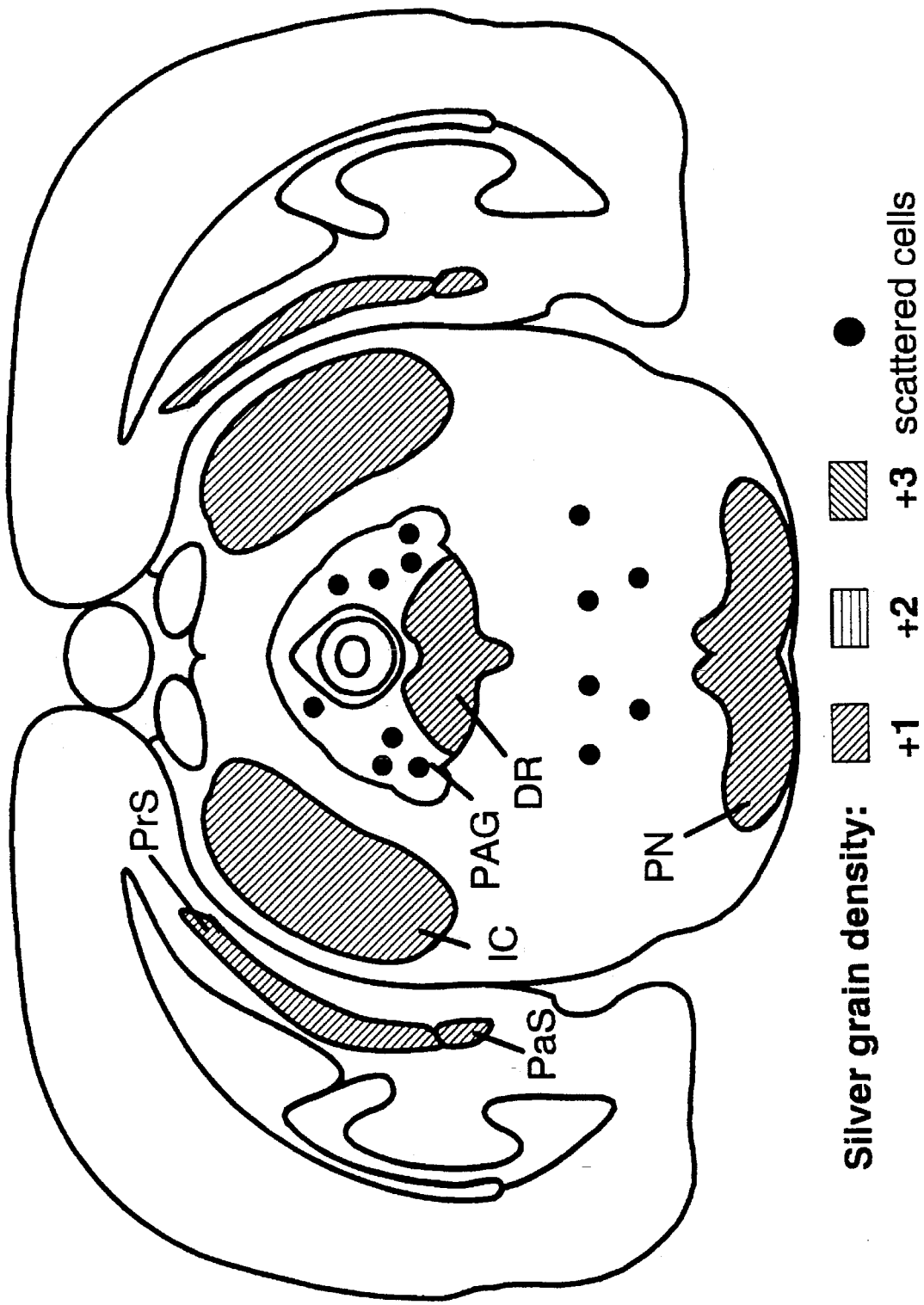
Figure 13H:
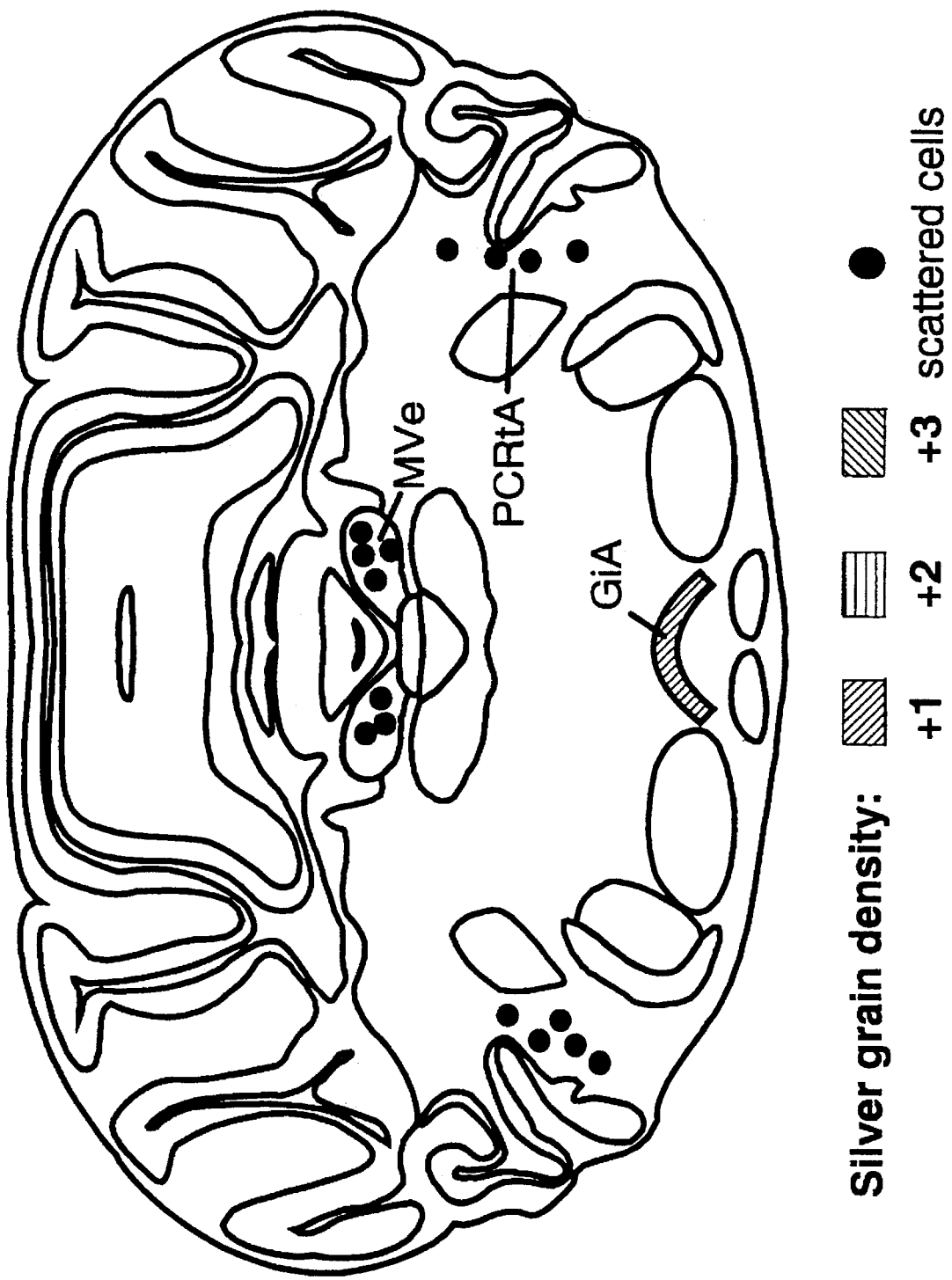

Activation of all Y-type receptors described thus far is thought to involve coupling to pertussis toxin-sensitive G-proteins which are inhibitory for adenylate cyclase activity ($G_i$ or $G_o$) (Wahlestedt and Reis, 1993). That the atypical Y1 receptor is linked to cyclase inhibition was prompted by the observation that pertussis toxin inhibited NPY-induced feeding in vivo (Chance et al., 1989); a more definitive analysis was impossible in the absence of the isolated receptor. Based on these prior observations, applicants investigated the ability of NPY to inhibit forskolin-stimulated cAMP accumulation in human embryonic kidney 293 cells stably transfected with rat Y5 receptors. Incubation of intact cells with 10 μM forskolin produced a 10-fold increase in cAMP accumulation over a 5 minute period, as determined by radioimmunoassay. Simultaneous incubation with rat/human NPY decreased the forskolin-stimulated cAMP accumulation by 67% in stably transfected cells (FIG. 12), but not in untransfected cells (data not shown). Applicants conclude that the rat Y5 receptor activation results in decreased cAMP accumulation, very likely through inhibition of adenylate cyclase activity. This result is consistent with the proposed signalling pathway for all Y-type receptors and for the atypical Y1 receptor in particular.

Peptides selected for their ability to stimulate feeding behavior in rats were able to activate the rat Y5 receptor with $EC_{50}$<10 nM (Kalra et al., 1991; Stanley et al., 1992; Balasubramaniam et al., 1994). These include rat/human NPY ($EC_{50}=1.8$ nM), rat/human $NPY_{2-36}$ ($EC_{50}=2.0$ nM), rat/human [$Leu^{31}$,$Pro^{34}$]NPY ($EC_{50}=0.6$ nM), rat/porcine PYY ($EC_{50}=4.0$ nM), and rat/human [D-$Trp^{32}$]NPY ($EC_{50}=7.5$ nM) (Table 6). Of particular interest is the Y5-selective peptide [D-$Trp^{32}$]NPY. This is a peptide which was shown to stimulate food intake when injected into rat hypothalamus, and which also attenuated NPY-induced feeding in the same paradigm (Balasubramaniam, 1994). Applicants observed that [D-$Trp^{32}$]NPY bound weakly to other Y-type clones with $K_i$>500 nM (Tables 4 and 5) and displayed no activity in functional assays (Table 7). In striking contrast, [D-$Trp^{32}$]NPY bound to the rat Y5 receptor with a $K_i=53$ nM and was fully able to mimic the inhibitory effect of NPY on forskolin-stimulated cAMP accumulation with an $EC_{50}$ of 25nm and an $E_{max}=72\%$. That [D-$Trp^{32}$]NPY was able to selectively activate the Y5 receptor while antagonizing the other subtype clones strongly suggests that Y5 receptor activation is responsible for the stimulatory effect of [D-Trp$^{32}$]NPY on feeding behavior in vivo.

TABLE 6: Functional activation of the rat Y5 receptor.

Functional data were derived from radioimmunoassay of cAMP accumulation in stably transfected cells stimulated with 10 μM forskolin. Peptides were tested for agonist activity at concentrations ranging from 0.03 pM to 0.3 μM. The maximum inhibition of cAMP accumulation ($E_{max}$) and the concentration producing a half-maximal effect ($EC_{50}$) were determined by nonlinear regression analysis according to a 4 parameter logistic equation.

TABLE 6

| Peptide | $E_{max}$ | $EC_{50}$ (nM) |
|---|---|---|
| rat/human NPY | 67% | 1.8 |
| rat/human NPY$_{2-36}$ | 84% | 2.0 |
| rat/human [Leu$^{31}$, Pro$^{34}$]NPY | 70% | 0.6 |
| rat/porcine PYY | 86% | 4.0 |
| rat/human [D-Trp$^{32}$]NPY | 72% | 7.5 |

TABLE 7: Binding and functional characterization of [D-Trp$^{32}$]NPY.

Binding data were generated as described in Tables 4 and 5. Functional data were derived from radioimmunoassay of cAMP accumulation in stably transfected cells stimulated with 10 μM forskolin. [D-Trp$^{32}$]NPY was tested for agonist activity at concentrations ranging from 0.03 pM to 0.3 μM. Alternatively, [D-Trp$^{32}$]NPY was included as a single spike (0.3 μM) in the human PYY concentration curve for human Y1 and human Y2 receptors, or in the human PP concentration curve for human Y4 receptors, and antagonist activity was detected by the presence of a rightward shift (from $EC_{50}$ to $EC_{50}'$). $K_b$ values were calculated according to the equation: $K_b=[[D-Trp^{32}]NPY/((EC_{50}/EC_{50}')-1)]$. The data shown are representative of at least two independent experiments.

TABLE 7

| Receptor Subtype | Species | Binding $K_i$ (nM) | Function $EC_{50}$ (nM) | $K_b$ (nM) | Activity |
|---|---|---|---|---|---|
| Y1 | Human | >1000 | | | None detected |
| Y2 | Human | >1000 | | | None detected |
| Y4 | Human | >1000 | | | None detected |
| Y5 | Human | 18 | | | Not Determined |
| Y1 | Rat | >1000 | | | Not Determined |
| Y2 | Rat | >1000 | | | Not Determined |
| Y4 | Rat | >1000 | | | Not Determined |
| Y5 | Rat | 53 | 25 | | Agonist |

Localization Studies

The mRNA for the NPY Y5 receptor was widely distributed in rat brain, and appeared to be moderately abundant (Table 10 and FIGS. 13A–13H). The midline thalamus contained many neurons with silver grains over them, particularly the paraventricular thalamic nucleus, the rhomboid nucleus, and the nucleus reunions. In addition, moderately intense hybridization signals were observed over neurons in both the centromedial and anterodorsal thalamic nuclei. In the hypothalamus, a moderate level of hybridization signal was seen over scattered neurons in the lateral hypothalamus, paraventricular, supraoptic, arcuate, and dorsomedial nuclei. In the paraventricular hypothalamus, positive neurons were observed primarily in the medial parvicellular subdivision.

TABLE 10

| Distribution of NPY Y5 mRNA in the Rat CNS | |
|---|---|
| REGION | Y5 mRNA |
| Cerebral cortex | +1 |
| Thalamus | |
| paraventricular n. | +3 |
| rhomboid n. | +3 |
| reunions n. | +3 |
| anterodorsal n. | +2 |
| Hypothalamus | |
| paraventricular n. | +2 |
| lateral hypoth. area | +2/+3 |
| supraoptic n. | +1 |
| arcuate n. | +2 |
| Hippocampus | |
| dentate gyrus | +1 |
| polymorph dentate gyrus | +2 |
| CA1 | 0 |
| CA3 | +1 |
| Amygdala | |
| central amygd. n., medial | +2 |
| anterior cortical amygd. n. | +2 |
| Olivary pretectal n. | +3 |
| Anterior pretectal n. | +3 |
| Substantia nigra, pars compacta | +2 |
| Superior colliculus | +2 |
| Central gray | +2 |
| Rostral linear raphe | +3 |
| Dorsal raphe | +1 |
| Inferior colliculus | +1 |
| Medial vestibular n. | +2/+3 |
| Parvicellular ret. n., alpha | +2 |
| Gigantocellular reticular n., alpha | +2 |
| Pontine nuclei | +1/+2 |

Moderate hybridization signals were found over most of the neurons in the polymorphic region of the dentate gyrus in the hippocampus, while lower levels were seen over scattered neurons in the CA3 region. In the amygdala, the central nucleus and the anterior cortical nucleus contained neurons with moderate levels of hybridization signal. In the mesencephalon, hybridization signals were observed over a number of areas. The most intense signals were found over neurons in the anterior and olivary pretectal nuclei, periaquaductal gray, and over the rostral linear raphe. Moderate hybridization signals were observed over neurons in the internal gray layer of the superior colliculus, the substantia nigra, pars compacta, the dorsal raphe, and the pontine nuclei. Most of the neurons in the inferior colliculus exhibited a low level of signal. In the medulla and pons, few areas exhibited substantial hybridization signals. The medial vestibular nucleus was moderately labeled, as was the parvicellular reticular nucleus, pars alpha, and the gigantocellular reticular nucleus.

Little or no hybridization signal was observed on sections hybridized with the radiolabeled sense oligonucleotide probe. More importantly, in the transfected COS-7 cells, the antisense probe hybridized only to the cells transfected with the rat Y5 cDNA (Table 9). These results indicate that the probe used to characterize the distribution of Y5 mRNA in rat brain is specific for this mRNA, and does not cross-hybridize to any of the other known NPY receptor mRNAs.

TABLE 9

Hybridization of antisense oligonucleotide
probes to transfected COS-7 cells.
Hybridization was performed as described in Methods. The
NPY Y5 probe hybridizes only to the cells transfected
with the Y5 cDNA. ND = not done.

| Cells | Mock | rY1 | rY2 | rY4 | rY5 |
|---|---|---|---|---|---|
| Oligo | | | | | |
| rY1 | − | + | − | ND | ND |
| rY2 | − | − | + | − | − |
| rY4 | − | − | − | + | − |
| rY5 | − | − | − | − | + |

EXPERIMENTAL DISCUSSION

In order to isolate new NPY receptor subtypes applicants choose an expression cloning approach where a functional receptor is actually detected with exquisite sensitivity on the surface of transfected cells, using a highly specific iodinated ligand. Using this strategy, applicants have identified a rat hypothalamic cDNA encoding a novel Y-type receptor (Y5). The fact that applicants had to screen $3.5 \times 10^6$ independent clones with a 2.7 kb average insert size to find two clones reveals either a very strong bias against Y5 cDNA cloning in the cDNA library construction procedure or that the Y5 mRNA is expressed at very low levels in rat hypothalamic tissue. The longest reading frame in the rat Y5 cDNA (CG-18) encodes a 456 amino acid protein with an estimated molecular weight of 50.1 kD. Given there are two N-linked glycosylation site in the amino terminus, the apparent molecular weight could be slightly higher. Applicants have isolated the human Y5 homolog from a human hippocampal cDNA library. The longest reading frame in the human Y5 cDNA (CG-19) encodes a 455 amino acid protein with an estimated molecular weight of 50 kD. The human Y5 receptor is one amino acid shorter than the rat Y5 and shows significant amino acid differences both in the N-terminal and the middle of the third intracellular loop portions of the protein. The seven transmembrane domains and the extracellular loops, however, are virtually identical and the protein motifs found in both species homologs are identical. Both human and rat Y5 receptors carry a large number of potential phosphorylation sites in their second and third intracellular loops which could be involved in the regulation of their functional characteristics.

The rat and human Y5 receptors both carry a leucine zipper in the first putative transmembrane domain. In such a structure, it has been proposed that segments containing periodic arrays of leucine residues exist in an alpha-helical conformation. The leucine side chains extending from one alpha-helix interact with those from a similar alpha helix of a second polypeptide, facilitating dimerization by the formation of a coiled coil (O'Shea et al, 1989). Usually, such patterns are associated with nuclear DNA binding protein like c-myc, c-fos and c-jun, but it is possible that in some proteins the leucine repeat simply facilitates dimerization and has little to do with positioning a DNA-binding region. Further evidence supporting the idea that dimerization of specific seven transmembrane receptors can occur comes from coexpression studies with muscarinic/adrenergic receptors where intermolecular "cross-talk" between chimeric G-protein coupled receptors has been described (Maggio et al., 1993). The tyrosine phosphorylation site found in the middle of this leucine zipper in transmembrane domain one (TM I) could be involved in regulating dimerization of the Y5 receptor. The physiological significance of G-protein coupled receptor dimerization remains to be elucidated but by analogy with peptide hormone receptors oligomerization, it could be involved in receptor activation and signal transduction (Wells, 1994).

The nucleotide and amino acid sequence analysis of Y5 (rat and human) reveals low identity levels with all 7 TM receptors including the Y1, Y2 and Y4 receptors, even in the transmembrane domains which are usually highly conserved within receptor subfamilies. Applicants have named CG-18 and CG-19 "Y5" receptors because of their unique amino acid sequence (87.2% identical with each other, ≦42% identical with the TM regions of previously cloned "Y" receptor subtypes) and pharmacological profile. The name is not biased toward any one member of the pancreatic polypeptide family. The "Y" has its roots in the original classification of Y1 and Y2 receptor subtypes (Wahlestedt et al., 1987). The letter reflects the conservation in pancreatic polypeptide family members of the C-terminal tyrosine, described as "Y" in the single letter amino acid code. The number is the next available in the Y-type series, position number three having been reserved for the pharmacologically defined Y3 receptor. Applicants note that the cloned human Y1 receptor was introduced by Larhammar and co-workers as a "human neuropeptide Y/peptide YY receptor of the Y1 type" (Larhammar et al., 1992). Similarly, the novel clones described herein can be described as rat and human neuropeptide Y/peptide YY receptors of the Y5 type. The rat hypothalamic Y5 receptor displays a very similar pharmacological profile to the pharmacologically described "atypical" Y1 receptor thought to mediate NPY-induced food intake in rat hypothalamus. Both the Y5 receptor and the "feeding receptor" display a preference for NPY and PYY-like analogs, a sensitivity to N-terminal peptide deletion, and a tolerance for $Pro^{34}$. Each would be considered Y1-like except for the anomalous ability of $NPY_{2-36}$ to bind and activate as well as NPY. Each appears to be sensitive to changes in the mid-region of the peptide ligand. For example, a study by Kalra and colleagues (1991) indicated that replacement of the NPY midregion by an aminooctanoic chain to produce $NPY_{1-4}$-$Aca_{25-36}$ dramatically reduced activity in a feeding behavioral assay. Likewise, applicants note that the robust difference in human PP binding ($K_f$=5.0 nM) and rat PP binding ($K_f$=230) to the rat Y5 receptor can be attributed to a series of 8 amino acid changes between residues 6-30 in the peptide ligands, with human PP bearing the closer resemblance to human NPY. These matching profiles, combined with a selective activation of the rat Y5 by the reported feeding "modulator" [D-$Trp^{32}$]NPY, support the identity of the rat Y5 as the "feeding receptor" first proposed to explain NPY-induced feeding in rat hypothalamus.

The distribution of Y5 mRNA in rat brain further extends the argument for a role of Y5 receptors in feeding behavior. The anatomical locus of the feeding response, for example, has been suggested to reside at least in part in the paraventricular hypothalamic nucleus (PVN) and also in the lateral hypothalamus, two places where Y5 mRNA was detected in abundance. Post-synaptic localization of the Y5 receptor in both of these regions can regulate the response to endogenously released NPY in vivo. The paraventricular nucleus receives projections from NPY-containing neurons in the arcuate nucleus, another region where Y5 mRNA was detected. This indicates a pre-synaptic role for the Y5 receptor in the control of NPY release via the arcuato-paraventricular projection, and consequently in the control of feeding behavior. The localization of the Y5 mRNA in the midline thalamic nuclei is also important. The paraventricular thalamic nucleus/centromedial nucleus complex projects heavily to the paraventricular hypothalamus and to the amygdala. As such, the Y5 receptor is a substrate for the emotional aspect of appetitive behaviors.

Y5 receptors are highly attractive targets for appetite and weight control based on several lines of research (Sahu and Kalra, 1993). NPY is the most potent stimulant of feeding behavior yet described (Clark et al., 1984; Levine and Morley, 1984; Stanley and Leibowitz, 1984). Direct injection of NPY into the hypothalamus of rats can increase food intake ~10-fold over a 4-hour period (Stanley et al., 1992). NPY-stimulated rats display a preference for carbohydrates over protein and fat (Stanley et al., 1985). Interestingly, NPY and NPY mRNA are increased in food-deprived rats (Brady et al., 1990; O'Shea and Gundlach, 1991) and also in rats which are genetically obese (Sanacora et al., 1990) or made diabetic by treatment with streptozotocin (White et al., 1990). One potential explanation is that NPY, a potent stimulant of feeding behavior in normal rats, is disregulated in the overweight or diabetic animal so that food intake is increased, accompanied by obesity. The physiological stress of obesity increases the risk for health problems such as cardiovascular malfunction, osteoarthritis, and hyperinsulinemia, together with a worsened prognosis for adult-onset diabetes. A nonpeptide antagonist targeted to the Y5 receptor could therefore be effective as a way to control not only appetite and body weight but an entire range of obesity- and diabetesrelated disorders (Dryden et al., 1994). There is also neurochemical evidence to suggest that NPY-mediated functions are disregulated in eating disorders such as bulimia and anorexia nervosa, so that they too could be responsive to treatment by a Y5-selective drug. It has been proposed, for example, that food intake in NPY-stimulated rats mimics the massive food consumption associated with binge eating in bulimia (Stanley, 1993). CSF levels of PYY but not NPY were elevated in bulimic patients who abstained from binging, and then diminished when binging was allowed (Berrettini et al., 1988). Conversely, NPY levels were elevated in underweight anorectic patients and then diminished as body weight was normalized (Kaye et al., 1990).

The Y5 pharmacological profile offers a new standard by which to review the molecular basis of all NPY-dependent processes; examples are listed in Table 11. Such an exercise suggests that the Y5 receptor is likely to have a physiological significance beyond feeding behavior. It has been reported, for example, that a Y-type receptor can regulate luteinizing hormone releasing hormone (LHRH) release from the median eminence of steroid-primed rats in vitro with an atypical Y1 pharmacological profile. NPY, $NPY_{2-36}$, and LP-NPY were all effective at 1 uM but deletion of as few as four amino acids from the N-terminus of NPY destroyed biological activity. The Y5 may therefore represent a therapeutic target for sexual or reproductive disorders. Preliminary in situ hybridization of rat Y5 mRNA in hippocampus and elsewhere further suggest that additional roles will be uncovered, for example, in the regulation of memory. It is worth while considering that the Y5 is so similar in pharmacological profile to the other Y-type receptors that it may have been overlooked among a mixed population of Y1, Y2 and Y4 receptors. Certain functions now associated with these subtypes could therefore be reassigned to Y5 as our pharmacological tools grow more sophisticated (Table 12). By offering new insight into NPY receptor pharmacology, the Y5 thereby provides a greater clarity and focus in the field of drug design.

TABLE 11

Pathophysiological Conditions Associated With NPY

The following pathological conditions have been linked to either 1) application of exogenous NPY, or 2) changes in levels of endogenous NPY.

| | | |
|---|---|---|
| 1 | obesity | Sahu and Kalra, 1993 |
| 2 | eating disorders (anorexia and bulimia nervosa) | Stanley, 1993 |
| 3 | sexual/reproductive function | Clark, 1994 |
| 4 | depression | Heilig and Weiderlov, 1990 |
| 5 | anxiety | Wahlestedt et al., 1993 |
| 6 | cocaine addiction | Wahlestedt et al., 1991 |
| 7 | gastric ulcer | Penner et al., 1993 |
| 8 | memory loss | Morley and Flood, 1990 |
| 9 | pain | Hua et al., 1991 |
| 10 | epileptic seizure | Rizzi et al., 1993 |
| 11 | hypertension | Zukowska-Grojec et al., 1993 |
| 12 | subarachnoid hemorrhage | Abel et al., 1988 |
| 13 | shock | Hauser et al., 1993 |
| 14 | circadian rhythm | Albers and Ferris, 1984 |
| 15 | nasal congestion | Lacroix et al., 1988 |
| 16 | diarrhea | Cox and Cuthbert, 1990 |
| 17 | neurogenic voiding dysfunction | Zoubek et al., 1993 |

A successful strategy for the design of a Y5-receptor based drug or for any drug targeted to single G protein-coupled receptor subtype involves the screening of candidate compounds 1) in radioligand binding assays so as to detect affinity for cross-reactive G protein-coupled receptors, and 2) in physiological assays so as to detect undesirable side effects. In the specific process of screening for a Y5-selective drug, the receptor subtypes most likely to cross-react and therefore most important for radioligand binding screens include the other "Y-type" receptors, Y1, Y2, Y3, and Y4. Cross-reactivity between the Y5 and any of the other subtypes could result in potential complications as suggested by the pathophysiological indications listed in Table 12. In designing a Y5 antagonist for obesity and appetite control, for example, it is important not to design a Y1 antagonist resulting in hypertension or increased anxiety, a Y2 antagonist resulting in memory loss, or a Y4 antagonist resulting in increased appetite.

TABLE 12

Y-Type Receptor Indications

| Y-type Receptor Indications | Receptor Subtype | Drug Activity | Reference |
|---|---|---|---|
| obesity, appetite disorder | atypical Y1 | antagonist | Sahu and Kalra, 1993 |
| adult onset diabetes | atypical Y1 | antagonist | Sahu and Kalra, 1993 |
| bulimia nervosa | atypical Y1 | antagonist | Stanley, 1993 |
| pheochromocytoma-induced hypertension | Y1 | antagonist | Grouzman et al., 1989 |
| subarachnoid hemorrhage | Y1 | antagonist | Abel et al., 1988 |

TABLE 12-continued

Y-Type Receptor Indications

| Y-type Receptor Indications | Receptor Subtype | Drug Activity | Reference |
|---|---|---|---|
| neurogenic vascular hypertrophy | Y1 Y2 | antagonist antagonist | Zukowska-Grojec et al., 1993 |
| epileptic seizure | Y2 | antagonist | Rizzi et al., 1993 |
| hypertension: central, peripheral regulation | peripheral Y1 central Y3 central Y2 | antagonist agonist antagonist | Grundemar and Hakanson, 1993 Barraco et al., 1991 |
| obesity, appetite disorder | Y4 or PP | agonist | Malaisse-Lagae et al., 1977 |
| anorexia nervosa | atypical Y1 | agonist | Berrettin i et al., 1988 |
| anxiety | Y1 | agonist | Wahlested t et al., 1993 |
| cocaine addiction | Y1 | agonist | Wahlested t et al., 1991 |
| stress-induced gastric ulcer | Y1 Y4 or PP | agonist agonist | Penner et al., 1993 |
| memory loss | Y2 | agonist | Morley and Flood, 1990 |
| pain | Y2 | agonist | Hua et al., 1991 |
| shock | Y1 | agonist | Hauser et al., 1993 |
| sleep disturbances, jet lag | Y2 | not clear | Albers and Ferris, 1984 |
| nasal decongestion | Y1 Y2 | agonist agonist | Lacroix et al., 1988 |
| diarrhea | Y2 | agonist | Cox and Cuthbert, 1990 |

The cloning of the Y5 receptor from human and rat is especially valuable for receptor characterization based on in situ localization, anti-sense functional knock-out, and gene induction. These studies will generate important information related to Y5 receptor function and its therapeutic significance. The cloned Y5 receptor lends itself to mutagenesis studies in which receptor/ligand interactions can be modeled. The Y5 receptor further allows us to investigate the possibility of other Y-type receptors through homology cloning. These could include new receptor subtypes as well as Y5 species homologs for the establishment of experimental animal models with relevance for human pathology. The Y5 receptor therefore represents an enormous opportunity for the development of novel and selective drug therapies, particularly those targeted to appetite and weight control, but also for memory loss, depression, anxiety, gastric ulcer, epileptic seizure, pain, hypertension, subarachnoid hemorrhage, sleeping disturbances, nasal congestion, neurogenic voiding dysfuncion, and diarrhea.

REFERENCES

Abel, P. W., Han, C., Noe, B. D., and McDonald, J. K. (1988). Neuropeptide Y: vasoconstrictor effects and possible role in cerebral vasospasm after experimental subarachnoid hemorrhage. *Brain Res.* 463: 250–258.

Albers, H. E., and Ferris, C. F. (1984). Neuropeptide Y: Role in light-dark cycle entrainment of hamster circadian rhythms. *Neurosci. Lett.* 50: 163–168.

Aruffo, A. and Seed, B. (1987). Molecular cloning of a CD28 cDNA by a high efficiency COS cell expression system. *PNAS*, 84, 8573–8577.

Balasubramaniam, A., Sheriff, S., Johnson, M. E., Prabhakaran, M., Huang, Y., Fischer, J. E., and Chance, W. T. (1994). [D-Trp$^{32}$]Neuropeptide Y: A competitive antagonist of NPY in rat hypothalamus. *J. Med. Chem.* 37: 311–815.

Berrettini, W. H., Kaye, W. H., Gwirtsman, H., and Allbright, A. (1988). Cerebrospinal fluid peptide YY immunoreactivity in eating disorders. *Neuropsychobiol* 19: 121–124.

Bradford, M. M. (1976). A rapid and sensitive method for the quantitation of microgram quantities of protein utilizing the principle of protein-dye binding. *Anal. Biochem.* 72: 248–254.

Brady, L. S., Smith, M. A., Gold, P. W., and Herkenham, M. (1990). Altered expression of hypothalamic neuropeptide Y mRNAs in food-restricted and food-deprived rats. *Neuroendocrinoloqy* 52: 441–447.

Chance, W. T., Sheriff, S., Foley-Nelson, T., Fischer, J. E., and Balasubramaniam, A. (1989). Pertuss toxin inhibits neuropeptide Y-induced feeding in rats. *Peptides* 10, 1283–1286.

Clark, J. T. (1994). Aging-induced decrements in neuropeptide Y: The retention of ejaculatory behavior is associated with site-selective differences. *Neurobiology of Aging* 15: 191–196.

Clark, J. T., Kalra, P. S., Crowley, W. R., and Kalra, S. P. (1984). Neuropeptide Y and human pancreatic polypeptide stimulate feeding behavior in rats. *Endocrinology* 115: 427–429.

Cox, H., and Cuthbert, A. W. (1990). The effects of neuropeptide Y and its fragments upon basal and electrically stimulated ion secretion in rat jejunum mucosa. *Br. J. Pharmac.* 101: 247–252.

Cullen, B. (1987). Use of eurkaryotic expression technology in the functional analysis of cloned genes. *Methods Enzymol.* 152: 685–704.

Dryden, S., Frankish, H., Wang, Q., and Williams, G. (1994). Neuropeptide Y and energy balance: one way ahead for the treatment of obesity? *Eur. J. Clin. Invest.* 24: 293–308.

Dumont, Y., J.-C. Martel, A. Fournier, S. St-Pierre, and R. Quirion. (1992). Neuropeptide Y and neuropeptide Y receptor subtypes in brain and peripheral tissues. *Progress in NeUrobiology* 38: 125–167.

Eva, C., Oberto, A., Sprengel, R. and E. Genazzani. (1992). The murine NPY-1 receptor gene: structure and delineation of tissue specific expression. *FEBS lett.* 314: 285–288.

Eva, C., Keinanen, K., Monyer, H., Seeburg, P., and Sprengel, R. (1990). Molecular cloning of a novel G protein-coupled receptor that may belong to the neuropeptide receptor family. *FEBS Lett.* 271, 80–84.

Fuhlendorff, J., U. Gether, L. Aakerlund, N. Langeland-Johansen, H. Thogersen, S. G. Melberg, U. B. Olsen, O. Thastrup, and T. W. Schwartz. (1990). [Leu$^{31}$,Pro$^{34}$]Neuropeptide Y: A specific Y1 receptor agonist. *Proc. Natl. Acad. Sci. USA* 87: 182–186.

Gerald, C., Adham, A., Kao, HT, Olsen, M. A., Laz, T. M., Vaysse, P., Hartig, P. R., Branchek, T. A. and R. L. Weinshank. The 5-HT$_4$ receptor: molecular cloning and pharmacological characterization of two splice variants (submitted for publication).

Grouzman, E., Comoy, E., and Bohuon, C. (1989). Plasma neuropeptide Y concentrations in patients with neuroendocrine tumors. *J. Clin. Endoc. Metab.* 68: 808–813.

Grundemar, L. and R1 Hakanson (1994). Neuropeptide Y effector systems: perspectives for drug development. *Trends. Pharmacol.* 15:153–159.

Grundemar, L., J. L. Krstenansky, and R. Hakanson. (1992). Activation of neuropeptide Y1 and neuropeptide Y2 receptors by substituted and truncated neuropeptide Y analogs: identification of signal epitopes. *Eur. J. Pharmacol.* 232: 271–278.

Gubler, U abd B. J. Hoffman. (1983). A simple and very efficient method for generating cDNA libraries. *Gene.* 25, 263–269

Hau, X. -Y., Boublik, J. H., Spicer, M. A., Rivier, J. E., Brown, M. R., and Yaksh, T. L. (1991). The antinociceptive effects of spinally administered neuropeptide Y in the rat: Systematic studies on structure-activity relationship. *JPET* 258: 243–253.

Hauser, G. J., Myers, A. K., Dayao, E. K., and Zukowska-Grojec, Z. (1993). Neuropeptide Y infusion improves hemodynamics and survival in rat endotoxic shock. *Am. J. Physiol.* 265: H1416–H1423.

Heilig, M., and Widerlov, E. (1990). Neuropeptide Y: an overview of central distribution, functional aspects, and possible involvement in neuropsychiatric illnesses. *Acta Psvchiatr. Scand.* 82: 95–114.

Herzog, H., Y. J. Hort, H. J. Ball, G. Hayes, J. Shine, and L. Selbie. (1992). Cloned human neuropeptide Y receptor couples to two different second messenger systems. *Proc. Natl. Acad. Sci. USA* 89: 5794–5798.

Herzog, H., Y. J. Hort, H. J. Ball, G. Hayes, J. Shine, and L. Selbie. (1992). Cloned human neuropeptide Y receptor couples to two different second messenger systems. *Proc. Natl. Acad. Sci. USA* 89, 5794–5798.

Kalra, S. P., Fuentes, M., Fournier, A., Parker, S. L., and Crowley, W. R. (1992). Involvement of the Y-1 receptor subtype in the regulation of luteinizing hormone secretion by neuropeptide Y in rats. Endocrinology 130: 3323–3330.

Kalra, S. P., Dube, M. G., Fournier, A., and Kalra, P. S. (1991). Structure-function analysis of stimulation of food intake by neuropeptide Y: Effects of receptor agonists. *Physiology & Behavior* 50: 5–9.

Kaye, W. H., Berrettini, W., Gwirtsman, H., and George, D. T. (1990). Altered cerebrospinal fluid neuropeptide Y and peptide YY immunoreactivity in anorexia and bulimia nervosa. *Arch. Gen. Psychiat.* 47: 548–556.

Kieffer, B., Befort, K., Gaveriaux-Ruff, C. and Hirth, C. G. (1992). The 6-opioid receptor: Isolation of a cDNA by expression cloning and pharmacological characterization. *Proc. natl. Acad. Sci. USA* 89, 12048–12052.

Kingston, R. E. (1987) in Ausubel, F. M.,Brent, R., Kingston, R. E., Moore, D. D., Seidman, J. G., Smith, J. A. & Struhl, K. (Eds), *Current Protocols in Molecular Biology*, John Wiley and Sons, N.Y., Vol. 1, pp. 4.2.3–4.2.4.

Kluxen, F. W., Bruns, C. and Lubbert H. (1992). Expression cloning of a rat brain somatostatin receptor cDNA. *Proc. Natl. Acad. Sci. USA* 89, 4618–4622.

Kornfeld, R. and Kornfeld, S. (1985). Assembly of asparagine linked oligosaccharides. *Annu. Rev. Biochem.* 54, 631–664.

Kozak, M. (1989). The scanning model for translation: an update. *J. Cell Biol.* 108, 229–241.

Kozak, M. (1991). Structural features in eukaryotic mRNAs that modulate the initiation of translation. *J. Biol. Chem.* 266, 19867–19870.

Krause, J., C. Eva, P. H. Seeburg, and R. Sprengel. (1991). Neuropeptide Y1 subtype pharmacology of a recombinantly expressed neuropeptide receptor. *Mol. Pharmacol.* 41: 817–821.

Lacroix, J. S., Stjarne, P., Angard, A., and Lundberg, M. (1988). Sympathetic vascular control of the pig nasal mucosa: reserpine-resistant, non-adrenergic nervous responses in relation to neuropeptide Y and ATP. *Acta Physiol. Scand.* 133: 183–197.

Landschultz, W. H., Johnson, P. F. and S. L. McKnight. (1988). The leucine zipper: a hypothetical structure common to a new class of DNA binding proteins. *Science* 240, 1759–1764.

Larhammar, D., A. G. Blomqvist, F. Yee, E. Jazin, H. Yoo, and C. Wahlestedt. (1992). Cloning and functional expression of a human neuropeptide Y/peptide YY receptor of the Y1 type. *J. Biol. Chem.* 267: 10935–10938.

Levine, A. S., and Morley, J. E. (1984). Neuropeptide Y: A potent inducer of consummatory behavior in rats. *Peptides* 5: 1025–1029.

Maggio, R., Vogel Z. and J. Wess. (1993). Coexpression studies with mutant muscarinic/adrenergic receptors provide evidence for intermolecular "cross-talk" between G-protein-linked receptors. *Proc. Natl. Acad. Sci. USA* 90: 3103–3107.

Malaisse-Lagai, F., Carpentier, J. -L., Patel, Y.C., Malaisse, W. J., and Orci, L. (1977). Pancreatic polypeptide: A possible role in the regulation of food intake in the mouse. Hypothesis. *Experientia* 33: 915–917.

McCormick, M. (1987). Sib Selection. Methods in Enzymology, 151: 445–449.

Miller, J. and Germain, R. N. (1986). Efficient cell surface expression of class II MHC molecules in the absence of associated invariant chain. *J. Exp. Med.* 164: 1478–1489.

Michel, M. C. (1991). Receptors for neuropeptide Y: multiple subtypes and multiple second messengers. Trends Pharmacol.: 12: 389–394.

Morley, J. E., and Flood, J. F. (1991). Neuropeptide Y and memory processing. An. N.Y. *Acad. Sci.* 611: 226–231.

Okayama, H. and P. Berg (1983). A cDNA cloning vector that permits expression of cDNA inserts in mammalian cells. *Mol. Cell. Biol.* 3: 280–289.

O'Shea, R. D., and Gundlach, A. L. (1991). Preproneuropeptide Y messenger ribonucleic acid in the hypothalamic arcuate nucleus of the rat is increased in food deprivation or dehydration. *J. Neuroendocrinol.* 3: 11–14.

O'Shea, E. K., Rutkowski, R. and P. S. Kim. (1989). Evidence that the leucine zipper is a coiled coil. *Science* 243: 538–542.

Penner, S. B., Smyth, D. D., and Glavin, G. B. (1993). Effects of neuropeptide Y and [Leu$^{31}$,Pro$^{34}$]Neuropeptide Y on experimental gastric lesion formation and gastric secretion in the rat. JPET. 266: 339–343.

Probst, W. C., Snyder, L. A., Schuster, D. I., Brosius, J and Sealfon, S. C. (1992). Sequence alignment of the G-protein coupled receptor superfamily. *DNA and Cell Bio.* 11, 1–20.

Sahu, A., and Kalra, S. P. (1993). Neuropeptidergic regulation of feeding behavior (neuropeptide Y). *Trends Endocrinol. Metab.* 4: 217–224.

Rizzi, M., Samini, R., Sperk, G., and Vezzani, A. (1993). Electrical kindling of the hippocampus is associated with functional activation of neuropeptide Y-containing neurons. Eur. *J. Neuroscience* 5: 1534–1538.

Sanacora, G., Kershaw, M., Finkelstein, J. A., and White, J. D. Increased hypothalamic content of preproneuropeptide Y messenger ribonucleic acid in genetically obese Zucker rats and its regulation by food deprivation. *Endocrinology* 127:730–737 (1990).

Schwartz, T. W., J. Fuhlendorff, L. L. Kjems, M. S. Kristensen, M. Vervelde, M. O'Hare, J. L. Krstenansky, and B. Bjornholm. (1990). Signal epitopes in the three-dimensional structure of neuropeptide Y. *Ann. N.Y. Acad. Sci.* 611: 35–47.

Stanley, B. G., Magdalin, W., Seirafi, A., Nguyen, M. M., and Leibowitz, S. F. (1992). Evidence for neuropeptide Y mediation of eating produced by food deprivation and for a variant of the Y1 receptor mediating this peptide's effect. *Peptides* 13: 581–587.

Stanley, B. G., and Leibowitz, S. F. (1984). Neuropeptide Y: Stimulation of feeding and drinking by injection into the paraventricular nucleus. *Life Sci.* 35: 2635–2642.

Stanley, B. G. Neuropeptide Y in multiple hypothalamic sites controls eating behavior, endocrine, and autonomic systems for body energy balance. In: *The Biology of Neuropeptide Y and Related Peptides*, pp. 457–509. Eds. W. F. Colmers and C. Wahlestedt. Humana Press, Totowa, New Jersey (1993).

Stanley, B. G., Daniel, D. R., Chin, A. S., and Leibowitz, S.F. (1985). Paraventricular nucleus injections of peptide YY and neuropeptide Y preferentially enhance carbohydrate ingestion. *Peptides* 6: 1205–1211.

Wahlestedt, C., L. Edvinsson, E. Ekblad, and R. Hakanson. Effects of neuropeptide Y at sympathetic neuroeffector junctions: Existence of Y1 and Y2 receptors. In: Neuronal messengers in vascular function, Fernstrom Symp. No 10., pp. 231–242. Eds A. Nobin and C. H. Owman. Elsevier: Amsterdam (1987).

Wahlestedt, C., Karoum, F., Jaskiw, G., Wyatt, R. J., Larhammar, D., Ekman, R., and Reis, D. J. (1991). Cocaine-induced reduction of brain neuropeptide Y synthesis dependent on medial prefrontal cortex. *Proc. Natl. Acad. Sci.* 88: 2978–2082.

Wahlestedt, C., Regunathan, S., and D. J. Reis (1991). Identification of cultured cells selectively expressing Yi-, Y2-, or Y3-type receptors for neuropeptide Y/peptide YY. *Life Sciences* 50:PL-7 - PL-12.

Wahlestedt, C., Pich, E. M., Koob, G.F., Yee, F., and Heilig, M. (1993). Modulation of anxiety and neuropeptide Y-Y1 receptors by antisense oligodeoxynucleotides. *Science* 259: 528–531.

Wahlestedt, C., and D. J. Reis. (1993). Neuropeptide Y-Related Peptides and Their Receptors—Are the Receptors Potential Therapeutic Targets? *Ann. Rev. Pharmacol. Tox.* 32:309–352

Warden, D. and H. V. Thorne. (1968). Infectivity of polyoma virus DNA for mouse embryo cells in presence of diethylaminoethyl-dextran. *J. Gen. Virol.* 3, 371.

Wells, J. A. (1994). Structural and functional basis for hormone binding and receptor oligomerization. *Current Opinion in Cell Biology* 6:163–173

White, J. D., Olchovsky, D., Kershaw, M., and Berelowitz, M. (1990). Increased hypothalamic content of preproneuropeptide-Y messenger ribonucleic acid in streptozotocin-diabetic rats. *Endocrinology* 126: 765–772.

Zoubek, J., Somogyi, G. T., and De Groat, W. C. (1993). A comparison of inhibitory effects of neuropeptide Y on rat urinary bladder, urethra, and vas deferens. *Am. J. Physiol.* 265: R536–R543.

Zukowska-Grojec, Z., Haass, M., and Bayorh, M. (1986). Neuropeptide Y and peptide YY mediate non-adrenergic vasoconstriction and modulate sympathetic responses in rats. *Reg. Pept.* 15: 99–110.

Zukowska-Grojec, Z., Bergeson, S., Kuch-Wocial, A., and Colton, C. (1993). Mitogenic effect of neuropeptide Y in rat vascular smooth muscle cells. Neuropeptide Y Conference Abstracts, (Cambridge) C10.

---

What is claimed is:

1. An isolated nucleic acid molecule encoding a human Y5 receptor having the amino acid sequence shown in Seq. ID No. 4.

2. An isolated nucleic acid molecule of claim 1, wherein the nucleic acid molecule is a DNA molecule.

3. An isolated DNA molecule of claim 2, wherein the DNA molecule is a cDNA molecule.

4. An isolated DNA molecule of claim 2, wherein the DNA molecule is a genomic DNA molecule.

5. An isolated nucleic acid molecule of claim 1, wherein the nucleic acid molecule is an RNA molecule.

6. An isolated nucleic acid molecule encoding a rat Y5 receptor, having the amino acid sequence shown in Seq. ID No. 2.

7. A vector comprising the nucleic acid molecule of claim 1.

8. A vector comprising the nucleic acid molecule of claim 6.

9. A vector of claim 7 adapted for expression in a bacterial cell which comprises the regulatory elements necessary for expression of the nucleic acid in the bacterial cell operatively linked to the nucleic acid encoding the human Y5 receptor as to permit expression thereof.

10. A vector of claim 7 adapted for expression in a yeast cell which comprises the regulatory elements necessary for expression of the nucleic acid in the yeast cell operatively linked to the nucleic acid encoding the human Y5 receptor as to permit expression thereof.

11. A vector of claim 7 adapted for expression in an insect cell which comprises the regulatory elements necessary for expression of the nucleic acid in the insect cell operatively linked to the nucleic acid encoding the human Y5 receptor as to permit expression thereof.

12. A vector of claim 7 adapted for expression in a mammalian cell which comprises the regulatory elements necessary for expression of the nucleic acid in the mammalian cell operatively linked to the nucleic acid encoding the human Y5 receptor as to permit expression thereof.

13. A vector of claim 8 adapted for expression in a mammalian cell which comprises the regulatory elements necessary for expression of the nucleic acid in the mammalian cell operatively linked to the nucleic acid encoding the rat Y5 receptor as to permit expression thereof.

14. A vector of claim 12 wherein the vector is a plasmid.

15. The plasmid of claim 14 designated pcEXV-hY5 (ATCC Accession No. 75943).

16. A vector of claim 8 adapted for expression in a bacterial cell which comprises the regulatory elements necessary for expression of the nucleic acid in the bacterial cell operatively linked to the nucleic acid encoding the rat Y5 receptor as to permit expression thereof.

17. A vector of claim 13 wherein the vector is a plasmid.

18. The plasmid of claim 17 designated pcEXV-rY5 (ATCC Accession No. 75944).

19. A mammalian cell comprising the vector of either of claims 12 or 13.

20. A mammalian cell of claim 19, wherein the mammalian cell is a COS-7 cell.

21. A mammalian cell of claim 19, wherein the mammalian cell is a 293 human embryonic kidney cell.

22. The cell of claim 21 designated 293-rY5-14 (ATCC Accession No. CRL 11757).

23. An isolated nucleic acid molecule of claim 6 wherein the nucleic acid molecule is a DNA molecule.

24. An isolated DNA molecule of claim 23, wherein the DNA molecule is a cDNA molecule.

25. An isolated DNA molecule of claim 23, wherein the DNA molecule is a genomic DNA molecule.

26. An isolated nucleic acid molecule of claim 6, wherein the nucleic acid molecule is an RNA molecule.

27. A vector of claim 8 adapted for expression in a yeast cell which comprises the regulatory elements necessary for expression of the nucleic acid in the yeast cell operatively linked to the nucleic acid encoding the rat Y5 receptor as to permit expression thereof.

28. A vector of claim 8 adapted for expression in an insect cell which comprises the regulatory elements necessary for expression of the nucleic acid in the insect cell operatively linked to the nucleic acid encoding the rat Y5 receptor as to permit expression thereof.

29. An isolated nucleic acid molecule encoding a human Y5 receptor having an amino acid sequence which is the same as the amino acid sequence encoded by the nucleic acid molecule contained in plasmid pcEXV-hY5 (ATCC Accession No. 75943).

30. An isolated nucleic acid molecule encoding a rat Y5 receptor having an amino acid sequence which is the same as the amino acid sequence encoded by the nucleic acid molecule contained in plasmid pcEXV-rY5 (ATCC Accession No. 75944).

* * * * *

UNITED STATES PATENT AND TRADEMARK OFFICE
CERTIFICATE OF CORRECTION

PATENT NO. : 5,602,024  
DATED : February 11, 1997  
INVENTOR(S) : Christophe P.G. Gerald, Mary W. Walker, Theresa Branchek, Richard L. Weinshank Page 1 of 2

It is certified that error appears in the above-identified patent and that said Letters Patent is hereby corrected as shown below:

Col.1, line 39, change "in situ" to -- *in situ* --
Col.2, line 46, change "Dec. 28 1993," to --Dec. 28, 1993,--
Col.3, line 24, change "$y^{36}$" to --$Y^{36}$--
    line 50, change "Dec. 28 1993 U.S. Pat. No. 5,576,653," to --Dec. 28, 1993, U.S. Pat. No. 5,516,653--.
    line 58, change "[$Leu^{31}$, $Pro^{34}$]" to --[$Leu^{31}$,$Pro^{34}$]--
    line 63, change "J. Med. Chem" to --*J. Med. Chem*--
Col.4, lines 23-24, change "in situ" to --*in situ*--
    line 32, change "BRIER" to --BRIEF--
Col.5, line 11, change "$^{125}$-PYY" to --$^{125}$I-PYY--
Col.15, line 7, change "abovedescribed" to --above-described--
Col.16, line 40, change "CDNA" to --cDNA--
Col.17, line 8-9, change "2 mML-glutamine" to --2 mM L-glutamine--
Col.19, line 1, change "$^{125}$-PYY" to --$^{125}$I-PYY--
    line 3, change "$^{125}$-IPYY" to --$^{125}$I-PYY--
Col.20, line 23, change "0 1X" to --0.1X--
Col.23, line 16, change "Endotheline-1" to --Endothelin-1 --
    line 25, after "Binding Studies" insert hard return.
    Start new paragraph with "The cDNA for.."
Col.25, line 33, change "[$Leu^{31}$ $Pro^{31}$,]" to --[$Leu^{31}$,$Pro^{34}$]--
    line 65, change "$^{125}$-PYY" to --$^{125}$I-PYY--
Col.26, line 30, change "in vivo" to --*in vivo*--
Col.30, line 28, Start new paragraph beginning with "The rat hypothalamic.."
    line 60, change "in vivo" to --*in vivo*--
Col.31, line 29, change "diabetesrelated" to --diabetes-related--
Col.33, line 39-40, change "in situ" to --*in situ*--
Col.34, line 43, change "*NeUrobiology*" to --*Neurobiology*--
Col.35, line 20, change "*Psvchiatr.*" to --*Psychiatr.*--
    line 42, change "6-opioid" to -- δ-opioid --
Col.37, line 26, change "Yi-," to -- Y1-, --

UNITED STATES PATENT AND TRADEMARK OFFICE
CERTIFICATE OF CORRECTION

PATENT NO. : 5,602,024
DATED : February 11, 1997
INVENTOR(S) : Christophe P.G. Gerald, Mary W. Walker, Theresa Branchek, Richard L. Weinshank It is certified that error appears in the above-identified patent and that said Letters Patent is hereby corrected as shown below:

Col.41, line ~33, change "(A) LENGTH: 456 amino acids" to
--(A) LENGTH: 457 amino acids--

Col.43, line ~45, change "Met Ser " to --Met Ser *--
$\phantom{Col.43, line ~45, change "Met Ser}_{455}\phantom{" to --Met Ser}_{455}$ Col.47, line ~32, change "(A) LENGTH: 455 amino acids" to
--(A) LENGTH: 457 amino acids--

Col.49, line ~45, change "His Met" to --His Met * *--
$\phantom{Col.49, line ~45, change "His Met}_{455}\phantom{" to --His Met}_{455}$ Signed and Sealed this Twenty-second Day of December, 1998

Attest:

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1501 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 61..1432

( x i ) SEQUENCE DESCRIPTION: SEQ ID NO:1:

```
TTAGTTTTGT  TCTGAGAACG  TTAGAGTTAT  AGTACCGTGC  GATCGTTCTT  CAAGCTGCTA              60

ATG  GAC  GTC  CTC  TTC  TTC  CAC  CAG  GAT  TCT  AGT  ATG  GAG  TTT  AAG  CTT    108
Met  Asp  Val  Leu  Phe  Phe  His  Gln  Asp  Ser  Ser  Met  Glu  Phe  Lys  Leu
 1              5                   10                  15

GAG  GAG  CAT  TTT  AAC  AAG  ACA  TTT  GTC  ACA  GAG  AAC  AAT  ACA  GCT  GCT    156
Glu  Glu  His  Phe  Asn  Lys  Thr  Phe  Val  Thr  Glu  Asn  Asn  Thr  Ala  Ala
                 20                  25                  30

GCT  CGG  AAT  GCA  GCC  TTC  CCT  GCC  TGG  GAG  GAC  TAC  AGA  GGC  AGC  GTA    204
Ala  Arg  Asn  Ala  Ala  Phe  Pro  Ala  Trp  Glu  Asp  Tyr  Arg  Gly  Ser  Val
```

-continued

|  |  |  |  |
|---|---|---|---|
| 35 | 40 | 45 | |

| GAC Asp | GAT Asp 50 | TTA Leu | CAA Gln | TAC Tyr | TTT Phe | CTG Leu | ATT Ile 55 | GGG Gly | CTC Leu | TAT Tyr | ACA Thr | TTC Phe 60 | GTA Val | AGT Ser | CTT Leu | 252 |
| CTT Leu 65 | GGC Gly | TTT Phe | ATG Met | GGC Gly | AAT Asn 70 | CTA Leu | CTT Leu | ATT Ile | TTA Leu 75 | ATG Met | GCT Ala | GTT Val | ATG Met | AAA Lys | AAG Lys 80 | 300 |
| CGC Arg | AAT Asn | CAG Gln | AAG Lys | ACT Thr 85 | ACA Thr | GTG Val | AAC Asn | TTT Phe | CTC Leu 90 | ATA Ile | GGC Gly | AAC Asn | CTG Leu | GCC Ala 95 | TTC Phe | 348 |
| TCC Ser | GAC Asp | ATC Ile | TTG Leu 100 | GTC Val | GTC Val | CTG Leu | TTT Phe | TGC Cys 105 | TCC Ser | CCT Pro | TTC Phe | ACC Thr | CTG Leu 110 | ACC Thr | TCT Ser | 396 |
| GTC Val | TTG Leu | TTG Leu 115 | GAT Asp | CAG Gln | TGG Trp | ATG Met | TTT Phe 120 | GGC Gly | AAA Lys | GCC Ala | ATG Met | TGC Cys 125 | CAT His | ATC Ile | ATG Met | 444 |
| CCG Pro | TTC Phe 130 | CTT Leu | CAA Gln | TGT Cys | GTG Val | TCA Ser 135 | GTT Val | CTG Leu | GTT Val | TCA Ser | ACT Thr 140 | CTG Leu | ATT Ile | TTA Leu | ATA Ile | 492 |
| TCA Ser 145 | ATT Ile | GCC Ala | ATT Ile | GTC Val | AGG Arg 150 | TAT Tyr | CAT His | ATG Met | ATA Ile | AAG Lys 155 | CAC His | CCT Pro | ATT Ile | TCT Ser | AAC Asn 160 | 540 |
| AAT Asn | TTA Leu | ACG Thr | GCA Ala | AAC Asn 165 | CAT His | GGC Gly | TAC Tyr | TTC Phe | CTG Leu 170 | ATA Ile | GCT Ala | ACT Thr | GTC Val | TGG Trp 175 | ACA Thr | 588 |
| CTG Leu | GGC Gly | TTT Phe | GCC Ala 180 | ATC Ile | TGT Cys | TCT Ser | CCC Pro | CTC Leu 185 | CCA Pro | GTG Val | TTT Phe | CAC His | AGT Ser 190 | CTT Leu | GTG Val | 636 |
| GAA Glu | CTT Leu | AAG Lys | GAG Glu | ACC Thr 195 | TTT Phe | GGC Gly | TCA Ser | GCA Ala | CTG Leu 200 | CTG Leu | AGT Ser | AGC Ser | AAA Lys | TAT Tyr 205 | CTC Leu | 684 |
| TGT Cys | GTT Val | GAG Glu | TCA Ser 210 | TGG Trp | CCC Pro | TCT Ser | GAT Asp | TCA Ser 215 | TAC Tyr | AGA Arg | ATT Ile | GCT Ala | TTC Phe 220 | ACA Thr | ATC Ile | 732 |
| TCT Ser 225 | TTA Leu | TTG Leu | CTA Leu | GTG Val | CAG Gln 230 | TAT Tyr | ATC Ile | CTG Leu | CCT Pro | CTA Leu 235 | GTA Val | TGT Cys | TTA Leu | ACG Thr | GTA Val 240 | 780 |
| AGT Ser | CAT His | ACC Thr | AGC Ser | GTC Val 245 | TGC Cys | CGA Arg | AGC Ser | ATA Ile | AGC Ser 250 | TGT Cys | GGA Gly | TTG Leu | TCC Ser | CAC His 255 | AAA Lys | 828 |
| GAA Glu | AAC Asn | AGA Arg | CTC Leu 260 | GAA Glu | GAA Glu | AAT Asn | GAG Glu | ATG Met 265 | ATC Ile | AAC Asn | TTA Leu | ACC Thr | CTA Leu 270 | CAG Gln | CCA Pro | 876 |
| TCC Ser | AAA Lys | AAG Lys | AGC Ser 275 | AGG Arg | AAC Asn | CAG Gln | GCA Ala | AAA Lys 280 | ACC Thr | CCC Pro | AGC Ser | ACT Thr | CAA Gln 285 | AAG Lys | TGG Trp | 924 |
| AGC Ser | TAC Tyr 290 | TCA Ser | TTC Phe | ATC Ile | AGA Arg | AAG Lys 295 | CAC His | AGA Arg | AGG Arg | AGG Arg | TAC Tyr 300 | AGC Ser | AAG Lys | AAG Lys | ACG Thr | 972 |
| GCC Ala 305 | TGT Cys | GTC Val | TTA Leu | CCC Pro | GCC Ala 310 | CCA Pro | GCA Ala | GGA Gly | CCT Pro | TCC Ser 315 | CAG Gln | GGG Gly | AAG Lys | CAC His | CTA Leu 320 | 1020 |
| GCC Ala | GTT Val | CCA Pro | GAA Glu | AAT Asn 325 | CCA Pro | GCC Ala | TCC Ser | GTC Val | CGT Arg 330 | AGC Ser | CAG Gln | CTG Leu | TCG Ser | CCA Pro 335 | TCC Ser | 1068 |
| AGT Ser | AAG Lys | GTC Val | ATT Ile | CCA Pro 340 | GGG Gly | GTC Val | CCA Pro | ATC Ile | TGC Cys 345 | TTT Phe | GAG Glu | GTG Val | AAA Lys | CCT Pro 350 | GAA Glu | 1116 |
| GAA Glu | AGC Ser | TCA Ser | GAT Asp | GCT Ala | CAT His | GAG Glu | ATG Met | AGA Arg | GTC Val | AAG Lys | CGT Arg | TCC Ser | ATC Ile | ACT Thr | AGA Arg | 1164 |

|     |     |     |     |     |     |     |     |     |     |     |     |     |     |     |      |
|-----|-----|-----|-----|-----|-----|-----|-----|-----|-----|-----|-----|-----|-----|-----|------|
|     |     |     | 355 |     |     |     | 360 |     |     |     | 365 |     |     |     |      |
| ATA | AAA | AAG | AGA | TCT | CGA | AGT | GTT | TTC | TAC | AGA | CTG | ACC | ATA | CTG | ATA  | 1212 |
| Ile | Lys | Lys | Arg | Ser | Arg | Ser | Val | Phe | Tyr | Arg | Leu | Thr | Ile | Leu | Ile  |
|     | 370 |     |     |     |     | 375 |     |     |     |     | 380 |     |     |     |      |
| CTC | GTG | TTC | GCC | GTT | AGC | TGG | ATG | CCA | CTC | CAC | GTC | TTC | CAC | GTG | GTG  | 1260 |
| Leu | Val | Phe | Ala | Val | Ser | Trp | Met | Pro | Leu | His | Val | Phe | His | Val | Val  |
| 385 |     |     |     |     | 390 |     |     |     |     | 395 |     |     |     |     | 400  |
| ACT | GAC | TTC | AAT | GAT | AAC | TTG | ATT | TCC | AAT | AGG | CAT | TTC | AAG | CTG | GTA  | 1308 |
| Thr | Asp | Phe | Asn | Asp | Asn | Leu | Ile | Ser | Asn | Arg | His | Phe | Lys | Leu | Val  |
|     |     |     |     | 405 |     |     |     |     | 410 |     |     |     |     | 415 |      |
| TAC | TGC | ATC | TGT | CAC | TTG | TTA | GGC | ATG | ATG | TCC | TGT | TGT | CTA | AAT | CCG  | 1356 |
| Tyr | Cys | Ile | Cys | His | Leu | Leu | Gly | Met | Met | Ser | Cys | Cys | Leu | Asn | Pro  |
|     |     |     | 420 |     |     |     |     | 425 |     |     |     |     | 430 |     |      |
| ATC | CTA | TAT | GGT | TTC | CTT | AAT | AAT | GGT | ATC | AAA | GCA | GAC | TTG | AGA | GCC  | 1404 |
| Ile | Leu | Tyr | Gly | Phe | Leu | Asn | Asn | Gly | Ile | Lys | Ala | Asp | Leu | Arg | Ala  |
|     |     | 435 |     |     |     |     | 440 |     |     |     |     | 445 |     |     |      |
| CTT | ATC | CAC | TGC | CTA | CAC | ATG | TCA | TGA | TTCTCTCTGTG | CACCAAAGAG |     |     |     |     | 1452 |
| Leu | Ile | His | Cys | Leu | His | Met | Ser | *   |     |     |     |     |     |     |      |
| 450 |     |     |     |     |     | 455 |     |     |     |     |     |     |     |     |      |

AGAAGAAACG TGGTAATTGA CACATAATTT ATACAGAAGT ATTCTGGAT     1501

( 2 ) INFORMATION FOR SEQ ID NO:2:

( i ) SEQUENCE CHARACTERISTICS:
        ( A ) LENGTH: 456 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Asp | Val | Leu | Phe | Phe | His | Gln | Asp | Ser | Ser | Met | Glu | Phe | Lys | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Glu | Glu | His | Phe | Asn | Lys | Thr | Phe | Val | Thr | Glu | Asn | Asn | Thr | Ala | Ala |
|     |     |     | 20  |     |     |     |     | 25  |     |     |     |     | 30  |     |     |
| Ala | Arg | Asn | Ala | Ala | Phe | Pro | Ala | Trp | Glu | Asp | Tyr | Arg | Gly | Ser | Val |
|     |     |     | 35  |     |     |     | 40  |     |     |     |     | 45  |     |     |     |
| Asp | Asp | Leu | Gln | Tyr | Phe | Leu | Ile | Gly | Leu | Tyr | Thr | Phe | Val | Ser | Leu |
|     | 50  |     |     |     |     | 55  |     |     |     |     | 60  |     |     |     |     |
| Leu | Gly | Phe | Met | Gly | Asn | Leu | Leu | Ile | Leu | Met | Ala | Val | Met | Lys | Lys |
| 65  |     |     |     |     | 70  |     |     |     |     | 75  |     |     |     |     | 80  |
| Arg | Asn | Gln | Lys | Thr | Thr | Val | Asn | Phe | Leu | Ile | Gly | Asn | Leu | Ala | Phe |
|     |     |     |     | 85  |     |     |     |     | 90  |     |     |     |     | 95  |     |
| Ser | Asp | Ile | Leu | Val | Val | Leu | Phe | Cys | Ser | Pro | Phe | Thr | Leu | Thr | Ser |
|     |     |     | 100 |     |     |     |     | 105 |     |     |     |     | 110 |     |     |
| Val | Leu | Leu | Asp | Gln | Trp | Met | Phe | Gly | Lys | Ala | Met | Cys | His | Ile | Met |
|     |     |     | 115 |     |     |     |     | 120 |     |     |     |     | 125 |     |     |
| Pro | Phe | Leu | Gln | Cys | Val | Ser | Val | Leu | Val | Ser | Thr | Leu | Ile | Leu | Ile |
|     |     | 130 |     |     |     |     | 135 |     |     |     |     | 140 |     |     |     |
| Ser | Ile | Ala | Ile | Val | Arg | Tyr | His | Met | Ile | Lys | His | Pro | Ile | Ser | Asn |
| 145 |     |     |     |     | 150 |     |     |     |     | 155 |     |     |     |     | 160 |
| Asn | Leu | Thr | Ala | Asn | His | Gly | Tyr | Phe | Leu | Ile | Ala | Thr | Val | Trp | Thr |
|     |     |     |     | 165 |     |     |     |     | 170 |     |     |     |     | 175 |     |
| Leu | Gly | Phe | Ala | Ile | Cys | Ser | Pro | Leu | Pro | Val | Phe | His | Ser | Leu | Val |
|     |     |     | 180 |     |     |     |     | 185 |     |     |     |     | 190 |     |     |
| Glu | Leu | Lys | Glu | Thr | Phe | Gly | Ser | Ala | Leu | Leu | Ser | Ser | Lys | Tyr | Leu |
|     |     |     | 195 |     |     |     |     | 200 |     |     |     |     | 205 |     |     |
| Cys | Val | Glu | Ser | Trp | Pro | Ser | Asp | Ser | Tyr | Arg | Ile | Ala | Phe | Thr | Ile |

|          |     |     |     |     | 210 |     |     |     |     | 215 |     |     |     |     | 220 |     |
|----------|-----|-----|-----|-----|-----|-----|-----|-----|-----|-----|-----|-----|-----|-----|-----|-----|

Ser Leu Leu Leu Val Gln Tyr Ile Leu Pro Leu Val Cys Leu Thr Val
225                 230                 235                 240

Ser His Thr Ser Val Cys Arg Ser Ile Ser Cys Gly Leu Ser His Lys
                245                 250                 255

Glu Asn Arg Leu Glu Glu Asn Glu Met Ile Asn Leu Thr Leu Gln Pro
            260                 265                 270

Ser Lys Lys Ser Arg Asn Gln Ala Lys Thr Pro Ser Thr Gln Lys Trp
        275                 280                 285

Ser Tyr Ser Phe Ile Arg Lys His Arg Arg Arg Tyr Ser Lys Lys Thr
    290                 295                 300

Ala Cys Val Leu Pro Ala Pro Ala Gly Pro Ser Gln Gly Lys His Leu
305                 310                 315                 320

Ala Val Pro Glu Asn Pro Ala Ser Val Arg Ser Gln Leu Ser Pro Ser
                325                 330                 335

Ser Lys Val Ile Pro Gly Val Pro Ile Cys Phe Glu Val Lys Pro Glu
                340                 345                 350

Glu Ser Ser Asp Ala His Glu Met Arg Val Lys Arg Ser Ile Thr Arg
        355                 360                 365

Ile Lys Lys Arg Ser Arg Ser Val Phe Tyr Arg Leu Thr Ile Leu Ile
    370                 375                 380

Leu Val Phe Ala Val Ser Trp Met Pro Leu His Val Phe His Val Val
385                 390                 395                 400

Thr Asp Phe Asn Asp Asn Leu Ile Ser Asn Arg His Phe Lys Leu Val
                405                 410                 415

Tyr Cys Ile Cys His Leu Leu Gly Met Met Ser Cys Cys Leu Asn Pro
        420                 425                 430

Ile Leu Tyr Gly Phe Leu Asn Asn Gly Ile Lys Ala Asp Leu Arg Ala
        435                 440                 445

Leu Ile His Cys Leu His Met Ser
450                 455

( 2 ) INFORMATION FOR SEQ ID NO:3:

( i ) SEQUENCE CHARACTERISTICS:
        ( A ) LENGTH: 1457 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 61..1432

( x i ) SEQUENCE DESCRIPTION: SEQ ID NO:3:

GTTTCCCTCT GAATAGATTA ATTTAAAGTA GTCATGTAAT GTTTTTTTGG TTGCTGACAA    60

ATG TCT TTT TAT TCC AAG CAG GAC TAT AAT ATG GAT TTA GAG CTC GAC    108
Met Ser Phe Tyr Ser Lys Gln Asp Tyr Asn Met Asp Leu Glu Leu Asp
1               5                   10                  15

GAG TAT TAT AAC AAG ACA CTT GCC ACA GAG AAT AAT ACT GCT GCC ACT    156
Glu Tyr Tyr Asn Lys Thr Leu Ala Thr Glu Asn Asn Thr Ala Ala Thr
            20                  25                  30

CGG AAT TCT GAT TTC CCA GTC TGG GAT GAC TAT AAA AGC AGT GTA GAT    204
Arg Asn Ser Asp Phe Pro Val Trp Asp Asp Tyr Lys Ser Ser Val Asp

|   |   |   |   |   | 35 |   |   |   |   | 40 |   |   |   |   | 45 |   |   |   |
|---|---|---|---|---|---|---|---|---|---|---|---|---|---|---|---|---|---|---|

GAC TTA CAG TAT TTT CTG ATT GGG CTC TAT ACA TTT GTA AGT CTT CTT       252
Asp Leu Gln Tyr Phe Leu Ile Gly Leu Tyr Thr Phe Val Ser Leu Leu
 50              55                  60

GGC TTT ATG GGG AAT CTA CTT ATT TTA ATG GCT CTC ATG AAA AAG CGT       300
Gly Phe Met Gly Asn Leu Leu Ile Leu Met Ala Leu Met Lys Lys Arg
 65              70                  75                          80

AAT CAG AAG ACT ACG GTA AAC TTC CTC ATA GGC AAT CTG GCC TTT TCT       348
Asn Gln Lys Thr Thr Val Asn Phe Leu Ile Gly Asn Leu Ala Phe Ser
                 85                  90                      95

GAT ATC TTG GTT GTG CTG TTT TGC TCA CCT TTC ACA CTG ACG TCT GTC       396
Asp Ile Leu Val Val Leu Phe Cys Ser Pro Phe Thr Leu Thr Ser Val
            100                 105                 110

TTG CTG GAT CAG TGG ATG TTT GGC AAA GTC ATG TGC CAT ATT ATG CCT       444
Leu Leu Asp Gln Trp Met Phe Gly Lys Val Met Cys His Ile Met Pro
        115                 120                 125

TTT CTT CAA TGT GTG TCA GTT TTG GTT TCA ACT TTA ATT TTA ATA TCA       492
Phe Leu Gln Cys Val Ser Val Leu Val Ser Thr Leu Ile Leu Ile Ser
    130                 135                 140

ATT GCC ATT GTC AGG TAT CAT ATG ATA AAA CAT CCC ATA TCT AAT AAT       540
Ile Ala Ile Val Arg Tyr His Met Ile Lys His Pro Ile Ser Asn Asn
145                 150                 155                 160

TTA ACA GCA AAC CAT GGC TAC TTT CTG ATA GCT ACT GTC TGG ACA CTA       588
Leu Thr Ala Asn His Gly Tyr Phe Leu Ile Ala Thr Val Trp Thr Leu
                165                 170                 175

GGT TTT GCC ATC TGT TCT CCC CTT CCA GTG TTT CAC AGT CTT GTG GAA       636
Gly Phe Ala Ile Cys Ser Pro Leu Pro Val Phe His Ser Leu Val Glu
            180                 185                 190

CTT CAA GAA ACA TTT GGT TCA GCA TTG CTG AGC AGC AGG TAT TTA TGT       684
Leu Gln Glu Thr Phe Gly Ser Ala Leu Leu Ser Ser Arg Tyr Leu Cys
        195                 200                 205

GTT GAG TCA TGG CCA TCT GAT TCA TAC AGA ATT GCC TTT ACT ATC TCT       732
Val Glu Ser Trp Pro Ser Asp Ser Tyr Arg Ile Ala Phe Thr Ile Ser
    210                 215                 220

TTA TTG CTA GTT CAG TAT ATT CTG CCC TTA GTT TGT CTT ACT GTA AGT       780
Leu Leu Leu Val Gln Tyr Ile Leu Pro Leu Val Cys Leu Thr Val Ser
225                 230                 235                 240

CAT ACA AGT GTC TGC AGA AGT ATA AGC TGT GGA TTG TCC AAC AAA GAA       828
His Thr Ser Val Cys Arg Ser Ile Ser Cys Gly Leu Ser Asn Lys Glu
                245                 250                 255

AAC AGA CTT GAA GAA AAT GAG ATG ATC AAC TTA ACT CTT CAT CCA TCC       876
Asn Arg Leu Glu Glu Asn Glu Met Ile Asn Leu Thr Leu His Pro Ser
            260                 265                 270

AAA AAG AGT GGG CCT CAG GTG AAA CTC TCT GGC AGC CAT AAA TGG AGT       924
Lys Lys Ser Gly Pro Gln Val Lys Leu Ser Gly Ser His Lys Trp Ser
        275                 280                 285

TAT TCA TTC ATC AAA AAA CAC AGA AGA AGA TAT AGC AAG AAG ACA GCA       972
Tyr Ser Phe Ile Lys Lys His Arg Arg Arg Tyr Ser Lys Lys Thr Ala
    290                 295                 300

TGT GTG TTA CCT GCT CCA GAA AGA CCT TCT CAA GAG AAC CAC TCC AGA      1020
Cys Val Leu Pro Ala Pro Glu Arg Pro Ser Gln Glu Asn His Ser Arg
305                 310                 315                 320

ATA CTT CCA GAA AAC TTT GGC TCT GTA AGA AGT CAG CTC TCT TCA TCC      1068
Ile Leu Pro Glu Asn Phe Gly Ser Val Arg Ser Gln Leu Ser Ser Ser
                325                 330                 335

AGT AAG TTC ATA CCA GGG GTC CCC ACT TGC TTT GAG ATA AAA CCT GAA      1116
Ser Lys Phe Ile Pro Gly Val Pro Thr Cys Phe Glu Ile Lys Pro Glu
            340                 345                 350

GAA AAT TCA GAT GTT CAT GAA TTG AGA GTA AAA CGT TCT GTT ACA AGA      1164
Glu Asn Ser Asp Val His Glu Leu Arg Val Lys Arg Ser Val Thr Arg

|     |     |     |     | 355 |     |     |     |     | 360 |     |     |     |     | 365 |     |      |
| --- | --- | --- | --- | --- | --- | --- | --- | --- | --- | --- | --- | --- | --- | --- | --- | ---- |
| ATA | AAA | AAG | AGA | TCT | CGA | AGT | GTT | TTC | TAC | AGA | CTG | ACC | ATA | CTG | ATA | 1212 |
| Ile | Lys | Lys | Arg | Ser | Arg | Ser | Val | Phe | Tyr | Arg | Leu | Thr | Ile | Leu | Ile |      |
|     | 370 |     |     |     |     | 375 |     |     |     |     | 380 |     |     |     |     |      |
| TTA | GTA | TTT | GCT | GTT | AGT | TGG | ATG | CCA | CTA | CAC | CTT | TTC | CAT | GTG | GTA | 1260 |
| Leu | Val | Phe | Ala | Val | Ser | Trp | Met | Pro | Leu | His | Leu | Phe | His | Val | Val |      |
| 385 |     |     |     |     | 390 |     |     |     |     | 395 |     |     |     |     | 400 |      |
| ACT | GAT | TTT | AAT | GAC | AAT | CTT | ATT | TCA | AAT | AGG | CAT | TTC | AAG | TTG | GTG | 1308 |
| Thr | Asp | Phe | Asn | Asp | Asn | Leu | Ile | Ser | Asn | Arg | His | Phe | Lys | Leu | Val |      |
|     |     |     |     | 405 |     |     |     |     | 410 |     |     |     |     | 415 |     |      |
| TAT | TGC | ATT | TGT | CAT | TTG | TTG | GGC | ATG | ATG | TCC | TGT | TGT | CTT | AAT | CCA | 1356 |
| Tyr | Cys | Ile | Cys | His | Leu | Leu | Gly | Met | Met | Ser | Cys | Cys | Leu | Asn | Pro |      |
|     |     |     | 420 |     |     |     |     | 425 |     |     |     |     | 430 |     |     |      |
| ATT | CTA | TAT | GGG | TTT | CTT | AAT | AAT | GGG | ATT | AAA | GCT | GAT | TTA | GTG | TCC | 1404 |
| Ile | Leu | Tyr | Gly | Phe | Leu | Asn | Asn | Gly | Ile | Lys | Ala | Asp | Leu | Val | Ser |      |
|     |     | 435 |     |     |     |     | 440 |     |     |     |     | 445 |     |     |     |      |
| CTT | ATA | CAC | TGT | CTT | CAT | ATG | TAA | TAA | TTCTCACTGT | | | TTACCAAGGA | | | | 1451 |
| Leu | Ile | His | Cys | Leu | His | Met | *   | *   |     |     |     |     |     |     |     |      |
|     | 450 |     |     |     |     | 455 |     |     |     |     |     |     |     |     |     |      |
| AAGAAC | | | | | | | | | | | | | | | | 1457 |

( 2 ) INFORMATION FOR SEQ ID NO:4:

( i ) SEQUENCE CHARACTERISTICS:
        ( A ) LENGTH: 455 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Ser | Phe | Tyr | Ser | Lys | Gln | Asp | Tyr | Asn | Met | Asp | Leu | Glu | Leu | Asp |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Glu | Tyr | Tyr | Asn | Lys | Thr | Leu | Ala | Thr | Glu | Asn | Asn | Thr | Ala | Ala | Thr |
|     |     |     | 20  |     |     |     |     | 25  |     |     |     |     | 30  |     |     |
| Arg | Asn | Ser | Asp | Phe | Pro | Val | Trp | Asp | Asp | Tyr | Lys | Ser | Ser | Val | Asp |
|     |     | 35  |     |     |     |     | 40  |     |     |     |     | 45  |     |     |     |
| Asp | Leu | Gln | Tyr | Phe | Leu | Ile | Gly | Leu | Tyr | Thr | Phe | Val | Ser | Leu | Leu |
|     | 50  |     |     |     |     | 55  |     |     |     |     | 60  |     |     |     |     |
| Gly | Phe | Met | Gly | Asn | Leu | Leu | Ile | Leu | Met | Ala | Leu | Met | Lys | Lys | Arg |
| 65  |     |     |     |     | 70  |     |     |     |     | 75  |     |     |     |     | 80  |
| Asn | Gln | Lys | Thr | Thr | Val | Asn | Phe | Leu | Ile | Gly | Asn | Leu | Ala | Phe | Ser |
|     |     |     |     | 85  |     |     |     |     | 90  |     |     |     |     | 95  |     |
| Asp | Ile | Leu | Val | Val | Leu | Phe | Cys | Ser | Pro | Phe | Thr | Leu | Thr | Ser | Val |
|     |     |     | 100 |     |     |     |     | 105 |     |     |     |     | 110 |     |     |
| Leu | Leu | Asp | Gln | Trp | Met | Phe | Gly | Lys | Val | Met | Cys | His | Ile | Met | Pro |
|     |     | 115 |     |     |     |     | 120 |     |     |     |     | 125 |     |     |     |
| Phe | Leu | Gln | Cys | Val | Ser | Val | Leu | Val | Ser | Thr | Leu | Ile | Leu | Ile | Ser |
|     | 130 |     |     |     |     | 135 |     |     |     |     | 140 |     |     |     |     |
| Ile | Ala | Ile | Val | Arg | Tyr | His | Met | Ile | Lys | His | Pro | Ile | Ser | Asn | Asn |
| 145 |     |     |     |     | 150 |     |     |     |     | 155 |     |     |     |     | 160 |
| Leu | Thr | Ala | Asn | His | Gly | Tyr | Phe | Leu | Ile | Ala | Thr | Val | Trp | Thr | Leu |
|     |     |     |     | 165 |     |     |     |     | 170 |     |     |     |     | 175 |     |
| Gly | Phe | Ala | Ile | Cys | Ser | Pro | Leu | Pro | Val | Phe | His | Ser | Leu | Val | Glu |
|     |     |     | 180 |     |     |     |     | 185 |     |     |     |     | 190 |     |     |
| Leu | Gln | Glu | Thr | Phe | Gly | Ser | Ala | Leu | Leu | Ser | Ser | Arg | Tyr | Leu | Cys |
|     |     | 195 |     |     |     |     | 200 |     |     |     |     | 205 |     |     |     |
| Val | Glu | Ser | Trp | Pro | Ser | Asp | Ser | Tyr | Arg | Ile | Ala | Phe | Thr | Ile | Ser |

```
         210                           215                           220

Leu  Leu  Leu  Val  Gln  Tyr  Ile  Leu  Pro  Leu  Val  Cys  Leu  Thr  Val  Ser
225                      230                      235                     240

His  Thr  Ser  Val  Cys  Arg  Ser  Ile  Ser  Cys  Gly  Leu  Ser  Asn  Lys  Glu
                    245                      250                     255

Asn  Arg  Leu  Glu  Glu  Asn  Glu  Met  Ile  Asn  Leu  Thr  Leu  His  Pro  Ser
               260                      265                     270

Lys  Lys  Ser  Gly  Pro  Gln  Val  Lys  Leu  Ser  Gly  Ser  His  Lys  Trp  Ser
          275                      280                     285

Tyr  Ser  Phe  Ile  Lys  Lys  His  Arg  Arg  Arg  Tyr  Ser  Lys  Lys  Thr  Ala
     290                      295                     300

Cys  Val  Leu  Pro  Ala  Pro  Glu  Arg  Pro  Ser  Gln  Glu  Asn  His  Ser  Arg
305                      310                      315                     320

Ile  Leu  Pro  Glu  Asn  Phe  Gly  Ser  Val  Arg  Ser  Gln  Leu  Ser  Ser  Ser
                    325                      330                     335

Ser  Lys  Phe  Ile  Pro  Gly  Val  Pro  Thr  Cys  Phe  Glu  Ile  Lys  Pro  Glu
               340                      345                     350

Glu  Asn  Ser  Asp  Val  His  Glu  Leu  Arg  Val  Lys  Arg  Ser  Val  Thr  Arg
          355                      360                     365

Ile  Lys  Lys  Arg  Ser  Arg  Ser  Val  Phe  Tyr  Arg  Leu  Thr  Ile  Leu  Ile
     370                      375                     380

Leu  Val  Phe  Ala  Val  Ser  Trp  Met  Pro  Leu  His  Leu  Phe  His  Val  Val
385                      390                      395                     400

Thr  Asp  Phe  Asn  Asp  Asn  Leu  Ile  Ser  Asn  Arg  His  Phe  Lys  Leu  Val
                    405                      410                     415

Tyr  Cys  Ile  Cys  His  Leu  Leu  Gly  Met  Met  Ser  Cys  Cys  Leu  Asn  Pro
               420                      425                     430

Ile  Leu  Tyr  Gly  Phe  Leu  Asn  Asn  Gly  Ile  Lys  Ala  Asp  Leu  Val  Ser
          435                      440                     445

Leu  Ile  His  Cys  Leu  His  Met
450                      455
```